(12) United States Patent
Freeman et al.

(10) Patent No.: US 11,890,461 B2
(45) Date of Patent: Feb. 6, 2024

(54) ADHESIVELY COUPLED WEARABLE MEDICAL DEVICE

(71) Applicant: ZOLL Medical Corporation, Chelmsford, MA (US)

(72) Inventors: Gary A Freeman, Waltham, MA (US); James A Patterson, III, Claridge, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 936 days.

(21) Appl. No.: 16/585,344

(22) Filed: Sep. 27, 2019

(65) Prior Publication Data

US 2020/0101278 A1 Apr. 2, 2020

Related U.S. Application Data

(60) Provisional application No. 62/738,113, filed on Sep. 28, 2018.

(51) Int. Cl.
*A61B 5/28* (2021.01)
*A61N 1/04* (2006.01)
(Continued)

(52) U.S. Cl.
CPC .............. *A61N 1/0484* (2013.01); *A61B 5/28* (2021.01); *A61B 5/361* (2021.01); *A61B 5/6805* (2013.01);
(Continued)

(58) Field of Classification Search
CPC .... A61N 1/0484; A61N 1/046; A61N 1/3925; A61N 1/365; A61N 1/3904;
(Continued)

(56) References Cited

U.S. PATENT DOCUMENTS

| 4,094,310 A | 6/1978 | McEachern et al. |
| 4,432,368 A | 2/1984 | Russek |

(Continued)

FOREIGN PATENT DOCUMENTS

| CN | 101031334 A | 9/2007 |
| CN | 101657229 A | 2/2010 |

(Continued)

OTHER PUBLICATIONS

Harnett, P.R. et al., "A Survey and Comparison of Laboratory Test Methods for Measuring Wicking", Textile Research Journal, Jul. 1984.

(Continued)

*Primary Examiner* — Rex R Holmes
(74) *Attorney, Agent, or Firm* — ZOLL Medical Corporation

(57) ABSTRACT

A patient-worn arrhythmia monitoring and treatment device weight between 250 grams and 2,500 grams includes at least one contoured pad configured to be adhesively coupled to a patient's torso, a plurality of therapy electrodes, at least one of which is integrated with the at least one contoured pad, and a plurality of ECG sensing electrodes, at least one of which is integrated with the at least one contoured pad. At least one housing configured to form a watertight seal with the at least one contoured pad extends no more than 5 cm from the contoured pad. A processor disposed within the housing is coupled to a therapy delivery circuit and configured to detect one or more treatable arrhythmias based on at least one ECG signal and cause a therapy delivery circuit to deliver at least one defibrillation pulse on detecting the one or more treatable arrhythmias.

19 Claims, 18 Drawing Sheets

(51) Int. Cl.
  *A61B 5/00* (2006.01)
  *A61N 1/39* (2006.01)
  *A61B 5/361* (2021.01)

(52) U.S. Cl.
  CPC ............ *A61B 5/6833* (2013.01); *A61N 1/046* (2013.01); *A61N 1/3925* (2013.01)

(58) Field of Classification Search
  CPC .. A61N 1/3968; A61N 1/3625; A61N 1/3621; A61N 1/36592; A61B 5/259; A61B 5/361; A61B 5/6805; A61B 5/6833; A61B 5/0205; A61B 5/02438; A61B 5/6802; A61B 5/6804; A61B 5/6831; A61B 5/318
  See application file for complete search history.

(56) References Cited

U.S. PATENT DOCUMENTS

| | | |
|---|---|---|
| 4,632,122 A | 12/1986 | Johansson et al. |
| 4,698,848 A | 10/1987 | Buckley |
| 4,928,690 A | 5/1990 | Heilman et al. |
| 4,978,926 A | 12/1990 | Zerod et al. |
| 5,062,834 A | 11/1991 | Gross et al. |
| 5,078,134 A | 1/1992 | Heilman et al. |
| 5,176,380 A | 1/1993 | Evans et al. |
| 5,330,505 A | 7/1994 | Cohen |
| 5,348,008 A | 9/1994 | Born et al. |
| 5,353,793 A | 10/1994 | Bornn |
| 5,357,696 A | 10/1994 | Gray et al. |
| 5,365,932 A | 11/1994 | Greenhut |
| 5,564,429 A | 10/1996 | Bornn et al. |
| 5,662,689 A | 9/1997 | Elsberry et al. |
| 5,718,242 A | 2/1998 | McClure et al. |
| 5,738,102 A | 4/1998 | Lemelson |
| 5,741,306 A | 4/1998 | Glegyak et al. |
| 5,758,443 A | 6/1998 | Pedrazzini |
| 5,792,190 A | 8/1998 | Olson et al. |
| 5,929,601 A | 7/1999 | Kaib et al. |
| 5,944,669 A | 8/1999 | Kaib |
| 6,016,445 A | 1/2000 | Baura |
| 6,045,503 A | 4/2000 | Grabner et al. |
| 6,065,154 A | 5/2000 | Hulings et al. |
| 6,097,982 A | 8/2000 | Glegyak et al. |
| 6,097,987 A | 8/2000 | Milani |
| 6,148,233 A | 11/2000 | Owen et al. |
| 6,169,387 B1 | 1/2001 | Kaib |
| 6,169,397 B1 | 1/2001 | Steinbach et al. |
| 6,253,099 B1 | 6/2001 | Oskin et al. |
| 6,280,461 B1 | 8/2001 | Glegyak et al. |
| 6,390,996 B1 | 5/2002 | Halperin et al. |
| 6,406,426 B1 | 6/2002 | Reuss et al. |
| 6,666,830 B1 | 12/2003 | Lehrman et al. |
| 6,681,003 B2 | 1/2004 | Linder et al. |
| 6,690,969 B2 | 2/2004 | Bystrom et al. |
| 6,790,178 B1 | 9/2004 | Mault et al. |
| 6,804,554 B2 | 10/2004 | Ujhelyi et al. |
| 6,827,695 B2 | 12/2004 | Palazzolo et al. |
| 6,865,413 B2 | 3/2005 | Halperin et al. |
| 6,908,437 B2 | 6/2005 | Bardy |
| 6,990,373 B2 | 1/2006 | Jayne et al. |
| 7,074,199 B2 | 7/2006 | Halperin et al. |
| 7,108,665 B2 | 9/2006 | Halperin et al. |
| 7,118,542 B2 | 10/2006 | Palazzolo et al. |
| 7,122,014 B2 | 10/2006 | Palazzolo et al. |
| 7,149,579 B1 | 12/2006 | Koh et al. |
| 7,177,684 B1 | 2/2007 | Kroll et al. |
| 7,220,235 B2 | 5/2007 | Geheb et al. |
| 7,277,752 B2 | 10/2007 | Matos |
| 7,295,871 B2 | 11/2007 | Halperin et al. |
| 7,340,296 B2 | 3/2008 | Stahmann et al. |
| 7,427,921 B2 | 9/2008 | Van Woudenberg |
| 7,453,354 B2 | 11/2008 | Reiter et al. |
| 7,476,206 B2 | 1/2009 | Palazzolo et al. |
| 7,488,293 B2 | 2/2009 | Marcovecchio et al. |
| 7,702,390 B1 | 4/2010 | Min |
| 7,810,172 B2 | 10/2010 | Williams |
| 7,831,303 B2 | 11/2010 | Rueter et al. |
| 7,974,689 B2 | 7/2011 | Volpe et al. |
| 8,121,683 B2 | 2/2012 | Bucher et al. |
| 8,140,154 B2 | 3/2012 | Donnelly et al. |
| 8,271,082 B2 | 9/2012 | Donnelly et al. |
| 8,369,944 B2 | 2/2013 | Macho et al. |
| 8,600,486 B2 | 12/2013 | Kaib et al. |
| 8,649,861 B2 | 2/2014 | Donnelly et al. |
| 8,706,215 B2 | 4/2014 | Kaib et al. |
| 8,904,214 B2 | 12/2014 | Volpe et al. |
| 8,909,335 B2 | 12/2014 | Radzelovage |
| 9,008,801 B2 | 4/2015 | Kaib et al. |
| 9,135,398 B2 | 9/2015 | Kaib et al. |
| 9,398,859 B2 | 7/2016 | Volpe et al. |
| 2002/0107435 A1 | 8/2002 | Swetlik et al. |
| 2003/0004547 A1 | 1/2003 | Owen et al. |
| 2003/0023277 A1 | 1/2003 | Owen et al. |
| 2003/0032988 A1 | 2/2003 | Fincke |
| 2003/0095648 A1 | 5/2003 | Kaib et al. |
| 2003/0149462 A1 | 8/2003 | White et al. |
| 2003/0158593 A1 | 8/2003 | Heilman et al. |
| 2003/0174049 A1 | 9/2003 | Beigel et al. |
| 2003/0195567 A1 | 10/2003 | Jayne et al. |
| 2003/0212311 A1 | 11/2003 | Nova et al. |
| 2003/0233129 A1 | 12/2003 | Matos |
| 2004/0007970 A1 | 1/2004 | Ma et al. |
| 2004/0049233 A1 | 3/2004 | Edwards |
| 2004/0143297 A1 | 7/2004 | Ramsey |
| 2005/0049515 A1 | 3/2005 | Misczynski et al. |
| 2005/0131465 A1 | 6/2005 | Freeman et al. |
| 2006/0036292 A1 | 2/2006 | Smith et al. |
| 2006/0085049 A1 | 4/2006 | Cory et al. |
| 2006/0129067 A1 | 6/2006 | Grajales et al. |
| 2006/0178706 A1 | 8/2006 | Lisogurski et al. |
| 2006/0220809 A1 | 10/2006 | Stigall et al. |
| 2006/0264776 A1 | 11/2006 | Stahmann et al. |
| 2006/0270952 A1 | 11/2006 | Freeman et al. |
| 2007/0073120 A1 | 3/2007 | Li et al. |
| 2007/0118056 A1 | 5/2007 | Wang et al. |
| 2007/0129769 A1 | 6/2007 | Bourget et al. |
| 2007/0161913 A1 | 7/2007 | Farrell et al. |
| 2007/0169364 A1 | 7/2007 | Townsend et al. |
| 2007/0239220 A1 | 10/2007 | Greenhut et al. |
| 2007/0265671 A1 | 11/2007 | Roberts et al. |
| 2007/0299474 A1 | 12/2007 | Brink |
| 2008/0004536 A1 | 1/2008 | Baxi et al. |
| 2008/0015454 A1 | 1/2008 | Gal |
| 2008/0030656 A1 | 2/2008 | Watson et al. |
| 2008/0031270 A1 | 2/2008 | Tran et al. |
| 2008/0033495 A1 | 2/2008 | Kumar |
| 2008/0045815 A1 | 2/2008 | Derchak et al. |
| 2008/0046015 A1 | 2/2008 | Freeman et al. |
| 2008/0058884 A1 | 3/2008 | Matos |
| 2008/0221631 A1 | 9/2008 | Dupelle |
| 2008/0249591 A1 | 10/2008 | Gaw et al. |
| 2008/0287770 A1 | 11/2008 | Kurzweil et al. |
| 2008/0306562 A1 | 12/2008 | Donnelly et al. |
| 2008/0312520 A1 | 12/2008 | Rowlandson et al. |
| 2008/0312709 A1 | 12/2008 | Volpe et al. |
| 2009/0073991 A1 | 3/2009 | Landrum et al. |
| 2009/0076336 A1 | 3/2009 | Mazar et al. |
| 2009/0076340 A1 | 3/2009 | Libbus et al. |
| 2009/0076341 A1 | 3/2009 | James et al. |
| 2009/0076342 A1 | 3/2009 | Amurthur et al. |
| 2009/0076343 A1 | 3/2009 | James et al. |
| 2009/0076344 A1 | 3/2009 | Libbus et al. |
| 2009/0076345 A1 | 3/2009 | Manicka et al. |
| 2009/0076346 A1 | 3/2009 | James et al. |
| 2009/0076348 A1 | 3/2009 | Manicka et al. |
| 2009/0076349 A1 | 3/2009 | Libbus et al. |
| 2009/0076350 A1 | 3/2009 | Bly et al. |
| 2009/0076363 A1 | 3/2009 | Bly et al. |
| 2009/0076364 A1 | 3/2009 | Libbus et al. |
| 2009/0076397 A1 | 3/2009 | Libbus et al. |
| 2009/0076405 A1 | 3/2009 | Amurthur et al. |
| 2009/0076410 A1 | 3/2009 | Libbus et al. |
| 2009/0076559 A1 | 3/2009 | Libbus et al. |
| 2009/0082691 A1 | 3/2009 | Denison et al. |

(56) References Cited

U.S. PATENT DOCUMENTS

| | | |
|---|---|---|
| 2009/0093687 A1 | 4/2009 | Telfort et al. |
| 2009/0138059 A1 | 5/2009 | Ouwerkerk |
| 2009/0177100 A1 | 7/2009 | Ternes |
| 2009/0234410 A1 | 9/2009 | Ibbus et al. |
| 2009/0264792 A1 | 10/2009 | Mazar |
| 2009/0275848 A1 | 11/2009 | Brockway et al. |
| 2009/0287120 A1 | 11/2009 | Ferren et al. |
| 2009/0292194 A1 | 11/2009 | Libbus et al. |
| 2010/0056881 A1 | 3/2010 | Libbus et al. |
| 2010/0069735 A1 | 3/2010 | Berkner |
| 2010/0076513 A1 | 3/2010 | Narren et al. |
| 2010/0076533 A1 | 3/2010 | Dar et al. |
| 2010/0083968 A1 | 4/2010 | Wondka et al. |
| 2010/0179438 A1 | 7/2010 | Heneghan et al. |
| 2010/0234715 A1 | 9/2010 | Shin et al. |
| 2010/0234716 A1 | 9/2010 | Engel |
| 2010/0295674 A1 | 11/2010 | Hsieh et al. |
| 2010/0298899 A1 | 11/2010 | Donnelly et al. |
| 2010/0312297 A1 | 12/2010 | Volpe et al. |
| 2011/0077728 A1 | 3/2011 | Li et al. |
| 2011/0196220 A1 | 8/2011 | Storm |
| 2011/0288604 A1 | 11/2011 | Kaib et al. |
| 2011/0288605 A1 | 11/2011 | Kaib et al. |
| 2012/0011382 A1 | 1/2012 | Volpe et al. |
| 2012/0112903 A1 | 5/2012 | Kaib et al. |
| 2012/0144551 A1 | 6/2012 | Guldalian |
| 2012/0146797 A1 | 6/2012 | Oskin et al. |
| 2012/0158074 A1 | 6/2012 | Hall |
| 2012/0158075 A1 | 6/2012 | Kaib et al. |
| 2013/0325078 A1 | 12/2013 | Whiting et al. |
| 2013/0325096 A1 | 12/2013 | Dupelle et al. |
| 2014/0163334 A1 | 6/2014 | Volpe et al. |
| 2014/0371806 A1 | 12/2014 | Raymond et al. |
| 2015/0005588 A1 | 1/2015 | Herken et al. |
| 2015/0039053 A1* | 2/2015 | Kaib ............... A61N 1/3993 607/63 |
| 2015/0217121 A1 | 8/2015 | Subramanian et al. |
| 2015/0231403 A1 | 8/2015 | Kaib et al. |
| 2016/0135706 A1 | 5/2016 | Sullivan et al. |
| 2016/0143585 A1 | 5/2016 | Donnelly et al. |
| 2017/0056682 A1* | 3/2017 | Kumar ............... G16H 50/20 |
| 2017/0224990 A1* | 8/2017 | Goldwasser ......... A61N 1/0476 |
| 2019/0022400 A1 | 1/2019 | Kumar et al. |

FOREIGN PATENT DOCUMENTS

| | | |
|---|---|---|
| CN | 101848677 A | 9/2010 |
| DE | 2644236 C3 | 4/1981 |
| EP | 0295497 B1 | 9/1993 |
| EP | 0335356 B1 | 3/1996 |
| EP | 1642616 A2 | 4/2006 |
| EP | 1455640 B1 | 1/2008 |
| EP | 1720446 B1 | 7/2010 |
| EP | 2308557 | 4/2011 |
| EP | 3121225 A1 | 1/2017 |
| EP | 3110503 B1 | 3/2019 |
| JP | S6368135 A | 3/1988 |
| JP | 5115450 A | 5/1993 |
| JP | H07541 A | 1/1995 |
| JP | H10-28679 A | 2/1998 |
| JP | H11319119 A | 11/1999 |
| JP | 2002-102361 A | 4/2002 |
| JP | 2002-514107 A | 5/2002 |
| JP | 2002200059 A | 7/2002 |
| JP | 2002534231 A | 10/2002 |
| JP | 2003235997 A | 8/2003 |
| JP | 2004538066 A | 12/2004 |
| JP | 2005275606 A | 10/2005 |
| JP | 2007531592 A | 11/2007 |
| JP | 2008302228 A | 12/2008 |
| JP | 2009510276 A | 3/2009 |
| JP | 2009518057 A | 5/2009 |
| JP | 2009528909 A | 8/2009 |
| JP | 2010-508128 A | 3/2010 |
| JP | 2010530114 A | 9/2010 |
| WO | 200002484 A1 | 1/2000 |
| WO | 2001042384 A2 | 6/2001 |
| WO | 2004054656 A1 | 7/2004 |
| WO | 2004067083 A2 | 8/2004 |
| WO | 2005082454 A1 | 9/2005 |
| WO | 2006050235 A1 | 5/2006 |
| WO | 2007019325 A2 | 2/2007 |
| WO | 20070057169 A1 | 5/2007 |
| WO | 2007077997 A1 | 7/2007 |
| WO | 2008137286 A1 | 11/2008 |
| WO | 2009034506 A1 | 3/2009 |
| WO | 2010014497 A1 | 2/2010 |
| WO | 2010025432 A1 | 3/2010 |
| WO | 20130106038 | 7/2013 |
| WO | 2015127466 A2 | 8/2015 |
| WO | 2017035502 A1 | 3/2017 |

OTHER PUBLICATIONS

Tebrake, Maggie G., "Selecting the right medical adhesive tape—Challenges facing the medical devise designer", 3M Medical OEM, www.3M.co.uk/medicaloem, 2014, 16 pages.

MDPI Open Access Publishing, Coatings | Special Issue : Fabric Coatings, http://www.mdpi.com/journal/coating/special_issues/fabric-coatings, Jul. 3, 2018, 7 pages.

PCT Search Report and Written Opinion for PCT Application No. PCT/US2019/053441, dated Feb. 24, 2020, 9 pages.

* cited by examiner

ADHESIVELY COUPLED WEARABLE MEDICAL DEVICE

CROSS-REFERENCE TO RELATED APPLICATIONS

This application claims priority under 35 U.S.C. § 119(e) to U.S. Provisional Patent Application Ser. No. 62/738,113 filed Sep. 28, 2018, titled "Adhesively Coupled Wearable Medical Device," the entirety of which is hereby incorporated by reference.

BACKGROUND

The present disclosure is directed to wearable cardiac monitoring and treatment devices.

A patient suffering from heart failure experiences symptoms caused by a weak or damaged heart contracting inefficiently and failing to pump effectively to circulate oxygenated blood through the body. A heart may be weakened by, for example, abnormal heart rhythms (e.g., heart arrhythmias), high blood pressure, coronary artery disease, myocardial infarction, and myocarditis.

Left untreated, heart failure could lead to certain life-threatening arrhythmias. Both atrial and ventricular arrhythmias are common in patients with heart failure. One of the deadliest cardiac arrhythmias is ventricular fibrillation, which occurs when normal, regular electrical impulses are replaced by irregular and rapid impulses, causing the heart muscle to stop normal contractions. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia.

Cardiac arrest can occur when various arrhythmias of the heart, such as ventricular fibrillation, ventricular tachycardia, pulseless electrical activity (PEA), and asystole (heart stops all electrical activity), result in the heart providing insufficient levels of blood flow to the brain and other vital organs for supporting life. It is generally useful to monitor heart failure patients in order to assess heart failure symptoms early and provide interventional therapies as soon as possible.

Wearable cardiac monitoring and treatment devices are provided to monitor for such arrhythmias and provide a treatment when a life-threatening arrhythmia is detected. Such devices are worn by the patient continuously to provide constant protection. As such, the devices need to be designed to be comfortable and easy to use.

SUMMARY

In one example, a patient-worn arrhythmia monitoring and treatment device includes at least one contoured pad configured to be adhesively coupled to a torso of a patient, a plurality of therapy electrodes, at least one of which is integrated with the contoured pad; and a plurality of ECG sensing electrodes, at least one of which is integrated with the contoured pad. At least one housing is configured to form a watertight seal with the contoured pad, the at least one housing extending no more than 5 cm from a surface of the contoured pad. An ECG acquisition and conditioning circuit can be disposed within the at least one housing and electrically coupled to the plurality of ECG sensing electrodes to provide at least one ECG signal of the patient, and a therapy delivery circuit can be disposed within the at least one housing. The therapy delivery circuit can be configured to deliver one or more therapeutic pulses to the patient through the plurality of therapy electrodes. In examples, a processor is disposed within the at least one housing and coupled to the therapy delivery circuit and is configured to analyze the at least one ECG signal of the patient and detect one or more treatable arrhythmias based on the at least one ECG signal and cause the therapy delivery circuit to deliver at least one defibrillation pulse to the patient on detecting the one or more treatable arrhythmias. In examples, the patient-worn monitoring and treatment device has a weight between 250 grams and 2,500 grams.

Implementations of the device may include one or more of the following features.

In examples, the at least one housing is configured to extend between 1 cm and 5 cm from the surface of the at least one contoured pad.

In examples, the at least one housing is configured to extend between 1 cm and 4 cm from the surface of the at least one contoured pad.

In examples, the at least one housing is configured to extend between 1 cm and 3 cm from the surface of the at least one contoured pad.

In examples, the delivery of the at least one defibrillation pulse includes a delivery of no more than one defibrillation pulse.

In examples, the plurality of ECG sensing electrodes are dry ECG electrodes configured to contact a skin of the patient. In examples, the plurality of ECG sensing electrodes are conductive electrodes. In examples, the plurality of ECG sensing electrodes are non-polarizable electrodes configured to contact the skin of the patient.

In examples, the one or more treatable arrhythmias include shockable ventricular tachycardia and ventricular fibrillation, and the therapy delivery circuit is further configured to deliver one or more pacing pulses. In examples, the one or more treatable arrhythmias include tachycardia and bradycardia.

In examples, the contoured pad is configured to be adhesively coupled to the patient for a short-term duration. In examples, the short-term duration is a duration up to at least one of around 24 hours, around 48 hours, around 4 days, around 1 week, and around 2 weeks. In examples, the weight of the patient-worn monitoring and treatment device is between at least one of 250 grams and 1,250 grams, 500 grams and 1,000 grams, and 750 grams and 900 grams. In examples, the weight of the patient-worn monitoring and treatment device is between 250 grams and 1,250 grams. In examples, the weight of the patient-worn monitoring and treatment device is between 500 grams and 1,000 grams. In examples, the weight of the patient-worn monitoring and treatment device is between 750 grams and 900 grams.

In examples, the contoured pad includes a flexible material configured to conform the contoured pad to a curvature of a region of the torso. In examples, the contoured pad includes a plurality of segments separated by a flexible material to conform the contoured pad to a curvature of a region of the torso. In examples, the at least one housing includes a plurality of housings, wherein each one of the plurality of housings is disposed on a corresponding one of the plurality of segments. The plurality of housings can be each configured to house one or more of the therapy delivery circuit, the ECG acquisition and conditioning circuit, the processor, at least one capacitor, and at least one power source.

In examples, electronics are disposed within the at least one housing. The electronics can include one or more of the therapy delivery circuit, the ECG acquisition and conditioning circuit, the processor, at least one capacitor, and at least one power source. The one or more of the therapy delivery circuit, the ECG acquisition and conditioning circuit, the processor, the at least one capacitor, and the at least one power source can be each within a separate enclosure.

In examples, the contoured pad, the at least one housing, and the electronics are assembled into an assembly such that a center of mass of the assembly is below a volumetric center of the assembly when the device is mounted on the patient.

In examples, a ratio of a distance between the center of mass and an inferior margin line of the at least one housing divided by the distance between the volumetric center and the inferior margin line is in a range of between at least one of 1% to 90%, 5% to 80%, and 10% to 70%. In examples, a ratio of a distance between the center of mass and an inferior margin line of the at least one housing divided by the distance between the volumetric center and the inferior margin line is in a range of between 1% to 90%. In examples, a ratio of a distance between the center of mass and an inferior margin line of the at least one housing divided by the distance between the volumetric center and the inferior margin line is in a range of between 5% to 80%. In examples, a ratio of a distance between the center of mass and an inferior margin line of the at least one housing divided by the distance between the volumetric center and the inferior margin line is in a range of between 10% to 70%. In examples, a ratio of a lateral distance between the center of mass and a patient-facing surface of the at least one contoured pad divided by a lateral distance between the volumetric center and the patient-facing surface of the at least one contoured pad is in a range of between at least one of 1% to 90%, 5% to 80%, and 10% to 70%. In examples, a ratio of a lateral distance between the center of mass and a patient-facing surface of the contoured pad divided by a lateral distance between the volumetric center and the patient-facing surface of the contoured pad is in a range of between 1% to 90%. In examples, a ratio of a lateral distance between the center of mass and a patient-facing surface of the contoured pad divided by a lateral distance between the volumetric center and the patient-facing surface of the contoured pad is in a range of between 5% to 80%. In examples, a ratio of a lateral distance between the center of mass and a patient-facing surface of the contoured pad divided by a lateral distance between the volumetric center and the patient-facing surface of the contoured pad is in a range of between 10% to 70%.

In examples, rotational torque at the center of mass of the assembly is in a range of between 0.15-1.0 lbf ft.

In examples, the at least one capacitor included in the electronics is a film capacitor. The at least one capacitor can have an envelope volume ranging from about 10 $cm^2$ to 15 $cm^2$. The at least one capacitor has a 140 microfarad capacity and a voltage rating of at least 1600V.

In examples, the at least one power source included in the electronics includes one or more batteries having a combined envelope volume not to exceed one quarter of the volume of the at least one housing and having a capacity of 1200 mAh to 8000 mAh. In examples, the at least one power source includes at least one Lithium ion battery. The one or more batteries can be flat packed lithium polymer batteries. In examples, the one or more batteries can have a combined volume ranging from about 1 $cm^2$ to 7 $cm^2$.

In examples, the device includes an active heat management system disposed within the at least one housing. The active heat management system can includes a thermoelectric cooling device. The active heat management system can include a low-profile fan.

In examples, the device includes a passive heat management system disposed within the at least one housing. The passive heat system can include a removably inserted cool pack. The passive heat management system can include a metallic heat sink layer disposed on one or more of the plurality of ECG sensing electrodes and/or the plurality of therapy electrodes. The passive heat management system can include one or more through holes extending between an interface between the contoured pad and the torso of the patient and an outer surface of the at least one housing.

In examples, the at least one contoured pad includes a second pad configured to be adhesively coupled to the torso of the patient. In examples, the second pad is configured to be contoured. A wireless transceiver can be integrated with the second pad configured to communicate with the therapy delivery circuit, and a second one of the plurality of therapy electrodes can be integrated with the second pad and in wireless communication with the therapy delivery circuit.

In examples, the at least one contoured pad includes a second pad configured to be adhesively coupled to the torso of the patient. In examples, the second pad is configured to be contoured. A second one of the plurality of therapy electrodes can be integrated with the second pad and in wired communication with the therapy delivery circuit.

In examples, the at least one contoured pad includes a third pad configured to be adhesively coupled to the torso of the patient. In examples, the third pad is configured to be contoured. The third pad can include a transceiver integrated with the third pad configured to communicate with the therapy delivery circuit. A third one of the plurality of therapy electrodes can be integrated with the third pad and in wired communication with the therapy delivery circuit. In examples, the third pad is configured to be adhesively coupled to the torso adjacent the atria.

In examples, the at least one contoured pad has an area footprint of about 200 square centimeters to about 300 square centimeters.

In examples, a ratio of the weight of the patient-worn monitoring and treatment device to the area footprint of the at least one contoured pad ranges from about 10 $kg/m^2$ to 100 $kg/m^2$.

In examples, the device includes a breathable anisotropic conductive gel disposed between the at least one contoured pad and the torso and configured for placement along at least one of the plurality of therapy electrodes. In examples, a ratio of an area footprint of the breathable anisotropic conductive gel to an area footprint of the at least one contoured pad ranges from about 0.30-0.75. A breathable adhesive can be disposed between the at least one contoured pad and the torso, wherein a ratio of the area footprint of the breathable adhesive to the area footprint of the at least one contoured pad ranges from about 0.05-0.25.

In examples, the at least one contoured pad includes one or more receptacles for receiving the at least one housing in a watertight mating. The one or more receptacles can include a sealing lip. The sealing lip can include an elastomeric waterproof material and engage a top surface of the at least one housing. The at least one housing can include a peripheral flange and the sealing lip receives the peripheral flange.

In one example, a patient-worn arrhythmia monitoring and treatment device includes at least one contoured pad configured to be adhesively coupled to a torso of a patient, a plurality of therapy electrodes, at least one of which is integrated with the contoured pad; and a plurality of ECG sensing electrodes, at least one of which is integrated with the contoured pad. At least one housing is configured to form a watertight seal with the contoured pad, the at least one housing extending between around 1 cm and 5 cm from a surface of the contoured pad. An ECG acquisition and conditioning circuit can be disposed within the at least one housing and electrically coupled to the plurality of ECG sensing electrodes to provide at least one ECG signal of the patient, and a therapy delivery circuit can be disposed within the at least one housing. The therapy delivery circuit can be configured to deliver one or more therapeutic pulses to the patient through the plurality of therapy electrodes. In examples, a processor is disposed within the at least one housing and coupled to the therapy delivery circuit and is configured to analyze the at least one ECG signal of the patient and detect one or more treatable arrhythmias based on the at least one ECG signal and cause the therapy delivery circuit to deliver at least one defibrillation pulse to the patient on detecting the one or more treatable arrhythmias. In examples, the patient-worn monitoring and treatment device has a weight between 250 grams and 2,500 grams.

Implementations of the device may include one or more of the following features.

In examples, the delivery of the at least one defibrillation pulse includes a delivery of one defibrillation pulse.

In examples, the plurality of ECG sensing electrodes are dry ECG electrodes configured to contact a skin of the patient. In examples, the plurality of ECG sensing electrodes are conductive electrodes. In examples, the plurality of ECG sensing electrodes are non-polarizable electrodes configured to contact the skin of the patient.

In examples, the one or more treatable arrhythmias include shockable ventricular tachycardia and ventricular fibrillation, and the therapy delivery circuit is further configured to deliver one or more pacing pulses. In examples, the one or more treatable arrhythmias include tachycardia and bradycardia.

In examples, the contoured pad is configured to be adhesively coupled to the patient for a short-term duration. In examples, the short-term duration is a duration up to at least one of around 24 hours, around 48 hours, around 4 days, around 1 week, and around 2 weeks. In examples, the weight of the patient-worn monitoring and treatment device is between 250 grams and 1,250 grams. In examples, the weight of the patient-worn monitoring and treatment device is between 500 grams and 1,000 grams. In examples, the weight of the patient-worn monitoring and treatment device is between 750 grams and 900 grams.

In examples, the contoured pad includes a flexible material configured to conform the contoured pad to a curvature of a region of the torso. In examples, the contoured pad includes a plurality of segments separated by a flexible material to conform the contoured pad to a curvature of a region of the torso. In examples, the at least one housing includes a plurality of housings, wherein each one of the plurality of housings is disposed on a corresponding one of the plurality of segments. The plurality of housings can be each configured to house one or more of the therapy delivery circuit, the ECG acquisition and conditioning circuit, the processor, at least one capacitor, and at least one power source.

In examples, electronics are disposed within the at least one housing. The electronics can include one or more of the therapy delivery circuit, the ECG acquisition and conditioning circuit, the processor, at least one capacitor, and at least one power source. The one or more of the therapy delivery circuit, the ECG acquisition and conditioning circuit, the processor, the at least one capacitor, and the at least one power source can be each within a separate enclosure.

In examples, the contoured pad, the at least one housing, and the electronics are assembled into an assembly such that a center of mass of the assembly is below a volumetric center of the assembly when the device is mounted on the patient.

in examples, a ratio of a distance between the center of mass and an inferior margin line of the at least one housing divided by the distance between the volumetric center and the inferior margin line is in a range of between 1% to 90%. In examples, a ratio of a distance between the center of mass and an inferior margin line of the at least one housing divided by the distance between the volumetric center and the inferior margin line is in a range of between 5% to 80%. In examples, a ratio of a distance between the center of mass and an inferior margin line of the at least one housing divided by the distance between the volumetric center and the inferior margin line is in a range of between 10% to 70%. In examples, a ratio of a lateral distance between the center of mass and a patient-facing surface of the contoured pad divided by a lateral distance between the volumetric center and the patient-facing surface of the contoured pad is in a range of between 1% to 90%. In examples, a ratio of a lateral distance between the center of mass and a patient-facing surface of the contoured pad divided by a lateral distance between the volumetric center and the patient-facing surface of the contoured pad is in a range of between 5% to 80%. In examples, a ratio of a lateral distance between the center of mass and a patient-facing surface of the contoured pad divided by a lateral distance between the volumetric center and the patient-facing surface of the contoured pad is in a range of between 10% to 70%.

In examples, rotational torque at the center of mass of the assembly is in a range of between 0.15-1.0 lbf ft.

In examples, the at least one capacitor included in the electronics is a film capacitor. The at least one capacitor can have an envelope volume ranging from about 10 $cm^2$ to 15 $cm^2$. The at least one capacitor has a 140 microfarad capacity and a voltage rating of at least 1600V.

In examples, the at least one power source included in the electronics includes one or more batteries having a combined envelope volume not to exceed one quarter of the volume of the at least one housing and having a capacity of 1200 mAh to 8000 mAh. In examples, the at least one power source includes at least one Lithium ion battery. The one or more batteries can be flat packed lithium polymer batteries. In examples, the one or more batteries can have a combined volume ranging from about 1 $cm^2$ to 7 $cm^2$.

In examples, the device includes an active heat management system disposed within the at least one housing. The active heat management system can includes a thermoelectric cooling device. The active heat management system can include a low-profile fan.

In examples, the device includes a passive heat management system disposed within the at least one housing. The passive heat system can include a removably inserted cool pack. The passive heat management system can include a metallic heat sink layer disposed on one or more of the plurality of ECG sensing electrodes and/or the plurality of therapy electrodes. The passive heat management system can include one or more through holes extending between an interface between the contoured pad and the torso of the patient and an outer surface of the at least one housing.

In examples, the at least one contoured pad includes a second contoured pad configured to be adhesively coupled to the torso of the patient. A wireless transceiver can be integrated with the second contoured pad configured to communicate with the therapy delivery circuit, and a second one of the plurality of therapy electrodes can be integrated with the second contoured pad and in wireless communication with the therapy delivery circuit.

In examples, the at least one contoured pad includes a second contoured pad configured to be adhesively coupled to the torso of the patient. A second one of the plurality of therapy electrodes can be integrated with the second contoured pad and in wired communication with the therapy delivery circuit.

In examples, the at least one contoured pad includes a third contoured pad configured to be adhesively coupled to the torso of the patient. The third contoured pad can include a transceiver integrated with the third contoured pad configured to communicate with the therapy delivery circuit. A third one of the plurality of therapy electrodes can be integrated with the third contoured pad and in wired communication with the therapy delivery circuit. In examples, the third contoured pad is configured to be adhesively coupled to the torso adjacent the atria.

In examples, the at least one contoured pad has an area footprint of about 200 square centimeters to about 300 square centimeters.

In examples, a ratio of the weight of the patient-worn monitoring and treatment device to the area footprint of the at least one contoured pad ranges from about 10 kg/m² to 100 kg/m².

In examples, the device includes a breathable anisotropic conductive gel disposed between the at least one contoured pad and the torso and configured for placement along at least one of the plurality of therapy electrodes. In examples, a ratio of an area footprint of the breathable anisotropic conductive gel to an area footprint of the at least one contoured pad ranges from about 0.30-0.75. A breathable adhesive can be disposed between the at least one contoured pad and the torso, wherein a ratio of the area footprint of the breathable adhesive to the area footprint of the at least one contoured pad ranges from about 0.05-0.25.

In examples, the at least one contoured pad includes one or more receptacles for receiving the at least one housing in a watertight mating. The one or more receptacles can include a sealing lip. The sealing lip can include an elastomeric waterproof material and engage a top surface of the at least one housing. The at least one housing can include a peripheral flange and the sealing lip receives the peripheral flange.

In one example, a patient-worn arrhythmia monitoring and treatment device, includes an anterior adhesively coupled pad configured for adhesion in an upper anterior region of a torso of a patient, wherein the anterior adhesively coupled pad has a weight in a range of 0.05-1.0 kg, and a posterior adhesively coupled pad in electrical connection with the anterior adhesively coupled pad. The posterior adhesively coupled pad can be configured for adhesion in a posterior region of the torso, wherein the posterior adhesively coupled pad has a weight in a range of 0.05-1.0 kg. The device includes a wearable support integrated with the anterior and posterior adhesively coupled pads and at least in part tracing a path from the upper anterior region of the torso, over a shoulder of the patient, and terminating at the posterior region of the torso. The wearable support can be configured to bear at least a portion of the weight of at least one of the anterior adhesively coupled pad and the posterior adhesively coupled pad. The device includes a pair of therapy electrodes configured to contact the torso of the patient and deliver one or more therapeutic pulses. One of the pair of therapy electrodes can be integrated within the anterior adhesively coupled pad and the other of the pair of therapy electrodes can be integrated within the posterior adhesively coupled pad. A plurality of ECG sensing electrodes can be integrated with the anterior and posterior adhesively coupled pads and configured to contact the torso of the patient. A first housing can be configured to form a watertight seal with the anterior adhesively coupled pad, and a second housing can be configured to form a watertight seal with the posterior adhesively coupled pad. An ECG acquisition and conditioning circuit can be disposed within the first or second housing and electrically coupled to the plurality of ECG sensing electrodes to provide at least one ECG signal of the patient, and a therapy delivery circuit can be disposed within the first or second housing and configured to deliver the one or more therapeutic pulses to the patient through an electrical connection to the pair of therapy electrodes. A processor can be disposed within the first or second housing and coupled to the therapy delivery circuit. In examples, the processor is configure to analyze the at least one ECG signal of the patient and detect one or more treatable arrhythmias based on the at least one ECG signal. The processor can be configured to cause the therapy delivery circuit to deliver up to five therapeutic pulses to the patient on detecting the one or more treatable arrhythmias. In examples, at least one power source is disposed within the first or second housing and coupled to the therapy delivery circuit and the pair of therapy electrodes.

Implementations of the device may include one or more of the following features.

In examples, a breathable adhesive is disposed between at least a portion of the wearable support and the shoulder of the patient.

In examples, the wearable support is a garment. In examples, the wearable support is at least one of a vest, a shirt, a sash, a strap, a belt, and a shoulder harness. The shoulder harness can be made of a non-adhesive stretchable fabric. In examples, the non-adhesive stretchable fabric includes conductive thread in communication with the anterior adhesively coupled pad and the posterior adhesively coupled pad. In examples, the shoulder harness has a tensile strength greater than at least 10% of a load exerted by at least one of the anterior adhesively coupled pad and the posterior adhesively coupled pad and not exceeding 10 times the load exerted by at least one of the anterior adhesively coupled pad and the posterior adhesively coupled pad. In examples, the shoulder harness has a percent elongation of between about 10% and 200%. In examples, the shoulder harness has an elasticity along a long-axis of the shoulder harness that is relatively lower that the elasticity along a short axis of the shoulder harness.

In examples, the shoulder harness has a curvature accommodating contours of a body of the patient. The shoulder harness can be at least one of molded, 3D printed, and knitted to a shape matching contours of the body of the patient.

In examples, the shoulder harness and at least one of the anterior adhesively coupled pad and posterior adhesively coupled pad are formed monolithically. The shoulder harness can be at least one of molded, 3D printed, and knitted to a shape matching contours of receiving portions of a body of the patient.

In examples, the shoulder harness has a greater tensile strength and lower stiffness coefficient than either of the an anterior adhesively couple pad and the posterior adhesively coupled pad.

In examples, the shoulder harness further includes at least one length adjuster configured to tension the shoulder harness. The at least one length adjuster can be at least one of a drawstring, a cinch strap, a lockable bungee pull, a pull cord and spring-loaded toggle stop, a ratchet strap, an adjustable buckle, an extendable and moveable hook and loop fastener strip, a tie, a snap, and a button.

In examples, the shoulder harness supports at least 1.0 lbf ft of torque at least at one end.

In examples, the shoulder harness stretches no more than 1 inch with the application of 22 lbf of force.

In examples, the shoulder harness stretches no more than 2 inches with the application of 30 lbf of force.

In examples, the shoulder harness stretches between 0.5-3 inches with the application of 30 lbf of force.

In examples, the shoulder harness has a higher MVTR than either or both of the anterior adhesively coupled pad and the posterior adhesively coupled pad. The shoulder harness can have an MVTR in a range of at least about 1200-2500 g/m2/24 hours and the anterior adhesively coupled pad and the posterior adhesively coupled pad have MVTRs in a range of about 50-1000 g/m2/24 hour.

In examples, the anterior adhesively coupled pad and posterior adhesively coupled pad are configured for adhering to the torso for a long-term duration. A long-term duration can be a duration including and up to at least one of around 2 weeks, around 1 month, around 6 weeks, around 8 weeks, and around 2 months. In examples, a long-term duration is including and up to at least one of around 6 months, around 1 year, and around 2 years.

In examples, 50-75% of an area footprint of the anterior adhesively coupled pad has an MVTR in a range of about 500-1200 g/m2/day and 25-50% of the area footprint of the anterior adhesively coupled pad has an MVTR in a range of about 250-500 g/m2/day.

In examples, 50-75% of an area footprint of the posterior adhesively coupled pad has an MVTR in a range of about 500-1200 g/m2/day and 25-50% of the area footprint of the posterior adhesively coupled pad has an MVTR in a range of about 250-500 g/m2/day.

In examples, a water vapor permeability of the device is 100 g/m2/24 hours.

In examples, a ratio of a weight of the device to an area footprint of the device ranges from about 0.008-0.030 lb/in$^2$.

In examples, the device includes a breathable anisotropic conductive gel disposed between the posterior adhesively coupled pad and the torso. In examples, a ratio of an area footprint of breathable anisotropic gel to an area footprint of the posterior adhesively coupled pad ranges from about 0.30-0.75. In examples, a ratio of an area footprint of adhesive to the area footprint of the posterior adhesively coupled pad ranges from about 0.05-0.25.

In one examples, a patient-worn arrhythmia monitoring and treatment device includes a contoured pad configured to be adhesively coupled to a torso of a patient, a plurality of therapy electrodes, at least one of which is integrated with the contoured pad, and a plurality of ECG sensing electrodes, at least one of which is integrated with the contoured pad. The plurality of ECG sensing electrodes are configured to contact a skin of the patient. In examples, the device includes at least one housing configured to form a watertight seal with the contoured pad. In examples, the device includes an ECG acquisition and conditioning circuit disposed within the at least one housing and electrically coupled to the plurality of ECG sensing electrodes to provide at least one ECG signal of the patient, and a therapy delivery circuit disposed within the at least one housing and configured to deliver one or more therapeutic pulses to the patient through the plurality of therapy electrodes. In examples, a processor is disposed within the at least one housing and is coupled to the therapy delivery circuit. In examples, the processor is configured to analyze the at least one ECG signal of the patient and detect one or more treatable arrhythmias based on the at least one ECG signal, and cause the therapy delivery circuit to deliver a treatment to the patient on detecting the one or more treatable arrhythmias.

Implementations of the device may include one or more of the following features.

In examples, the at least one housing extends between around 1 cm and 5 cm from a surface of the contoured pad.

In examples, the device has a weight between 500 g and 2,500 g.

In examples, the treatment includes a delivery of up to two defibrillation pulses. The treatment can include a delivery of no more than one defibrillation pulse.

In examples, the plurality of ECG sensing electrodes are dry electrodes configured to contact the skin of the patient. The plurality of ECG sensing electrodes can be conductive electrodes. The plurality of ECG sensing electrodes can be non-polarizable electrodes configured to contact the skin of the patient.

In examples, the contoured pad is configured to be adhesively coupled to the patient for a short-term duration. The short-term duration can be a duration up to at least one of around 24 hours, around 48 hours, around 4 days, around 1 week, and around 2 weeks.

In one example, a patient-worn arrhythmia monitoring and treatment device includes a first contoured pad configured to be adhesively coupled to a torso of a patient for supporting a first assembly, a second contoured pad coupled to the first contoured pad, the second contoured pad configured to be adhesively coupled to the torso of the patient for supporting a second assembly, and a wearable support integrated with at least one of the first and second adhesively coupled pads, wherein the wearable support is configured to bear at least a portion of the weight of at least one of the first assembly and the second assembly. In examples, the first assembly includes, a plurality of therapy electrodes, at least one of which is integrated with the contoured pad, a plurality of ECG sensing electrodes, at least one of which is integrated with the contoured pad, at least one housing configured to form a watertight seal with the contoured pad, the at least one housing extending between around 1 cm and 5 cm from a surface of the contoured pad, an ECG acquisition and conditioning circuit disposed within the at least one housing and electrically coupled to the plurality of ECG sensing electrodes to provide at least one ECG signal of the patient, a therapy delivery circuit disposed within the at least one housing and configured to deliver one or more therapeutic pulses to the patient through the plurality of therapy electrodes, and a processor disposed within the at least one housing and coupled to the therapy delivery circuit. In examples, the processor is configured to analyze the at least one ECG signal of the patient and detect one or more treatable arrhythmias based on the at least one ECG signal, and cause the therapy delivery circuit to deliver at least one defibrillation pulse to the patient on detecting the one or more treatable arrhythmias.

Implementations of the device may include one or more of the following features.

In examples, the weight of the patient-worn monitoring and treatment device is between 500 grams and 10 kilograms. The weight of the patient-worn monitoring and treatment device can be between 1000 grams and 8,000 grams. The weight of the patient-worn monitoring and treatment device can be between 2500 grams and 6000 grams.

DETAILED DESCRIPTION

This disclosure relates to a patient-worn adhesively coupled cardiac monitoring and treatment device that detects one or more treatable arrhythmias based on physiological signals from a patient. The treatable arrhythmias include those that may be treated by defibrillation pulses, such as ventricular fibrillation (VF) and shockable ventricular tachycardia (VT), or by one or more pacing pulses, such as bradycardia, tachycardia, and asystole. A wearable medical device as disclosed herein is adhesively coupled to a patient and monitors the patient's physiological conditions, e.g., cardiac signals, respiratory parameters, and patient activity, and delivers potentially life-saving treatment to the patient. Embodiments of patient-worn adhesively coupled cardiac monitoring and treatment devices can include garments or wearable supports for supporting one or more components on a patient's torso, components adhesively coupled to the torso of a patient, or some combination of garments or wearable supports and adhesively coupled components.

Figure 1:
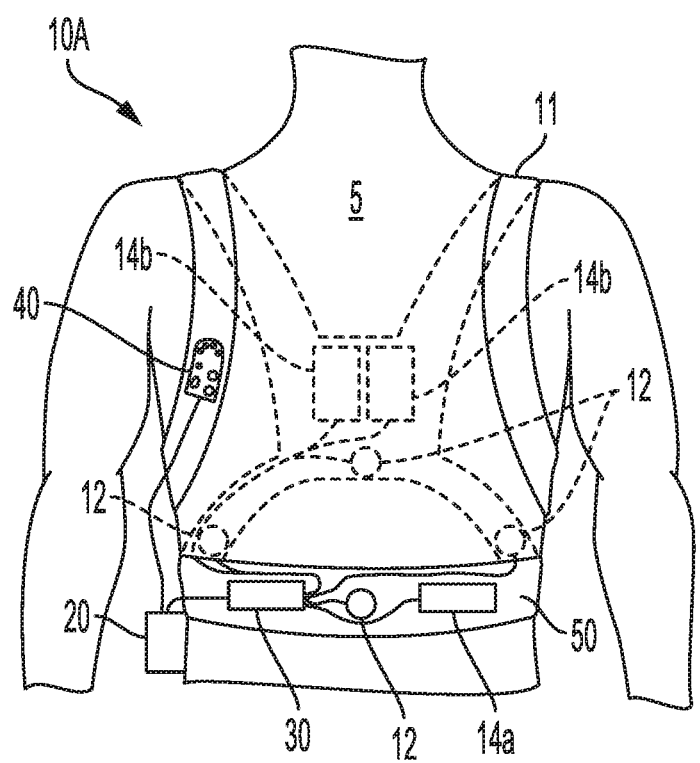
FIG. 1 depicts a schematic of an example wearable cardiac monitoring and treatment device including a wearable support.

As described in U.S. Pat. No. 8,983,597, titled "MEDICAL MONITORING AND TREATMENT DEVICE WITH EXTERNAL PACING," issued on Mar. 17, 2015 (hereinafter the "'597 Patent"), which is hereby incorporated herein by reference in its entirety, an example patient worn cardiac monitoring and treatment device can be, for example, an ambulatory medical device that is capable of and designed for moving with the patient as the patient goes about his or her daily routine. For example, as shown in FIG. 1, the ambulatory medical device 10A can be a wearable cardioverter defibrillator (WCD) and can include one or more of the following: a garment 11, one or more physiological sensors 12 (e.g., ECG electrodes, heart rate sensors, vibrational sensors, and/or other physiological sensors), one or more therapy electrodes 14a and 14b (collectively referred to herein as therapy electrodes 14), a medical device controller 20, a connection pod 30, a patient interface pod 40, a belt 50 about the patient's torso to support one or more components, or any combination of these. In some examples, at least some of the components of the medical device 10A can be configured to be affixed to the garment 11 (or in some examples, permanently integrated into the garment 11), which can be worn about the patient's torso 5.

The medical device controller 20 can be operatively coupled to the physiological sensors 12 which can be affixed to the garment 11, e.g., assembled into the garment 11 or removably attached to the garment 11, e.g., using hook and loop fasteners. In some implementations, the physiological sensors 12 can be permanently integrated into the garment 11. The medical device controller 20 can be operatively coupled to the therapy electrodes 14. For example, the therapy electrodes 14 can also be assembled into the garment 11, or, in some implementations, the therapy electrodes 14 can be permanently integrated into the garment 11.

In embodiments according to this disclosure, such as that of FIGS. 2-4D, one or more portions of the garment 11 of the device 10A of FIG. 1 can be eliminated, such as such as a holster portion, and the remaining portions combined with other attachment mechanisms. In embodiments, eliminating one or more portions of the garment 11 results in leaving a wearable support configured with relatively less surface area. Such a wearable support can be, for example, a shoulder strap, a vest, a belt, a harness, a bandeau, and/or a sash. In implementations, the wearable support can be fitted to the body as a lightweight stretchable support garment, or other structure for supporting heavier components of the device 10B-G. In one example, the wearable support may be a belt 50 or sash 53, as shown in FIGS. 2 through 4D. The belt 50 or sash 53 is configured to support heavy components of the device 10B-10G while other components, such as therapy electrodes 14 and sensors 12 (e.g., ECG sensors), can be adhesively attached to the torso 5 of the patient.

Figure 2:
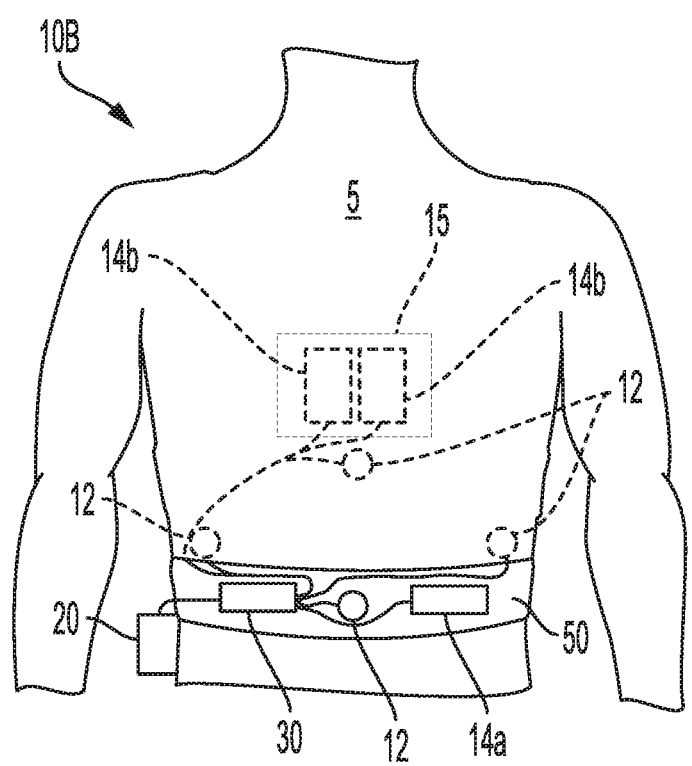
FIG. 2 depicts a schematic of an example wearable cardiac monitoring and treatment device including a wearable support and adhesively coupled portions.

In one example, as shown in FIG. 2, posterior placed therapy electrodes 14b can be integrated into and/or adhered to the patient's skin by an adhesive patch 15 surrounding some or all of the therapy electrodes 14b. The patch can provide an adhesive border for attaching the covered and/or integrated one or more therapy electrodes 14b to the torso 5 of the patient. Heavier components disposed on the wearable support, a belt 50, can include a medical device controller 20 including high voltage components such as one or more batteries, one or more capacitors, one or more circuit boards, one or more controllers, and one or more user interfaces. In this example, an anterior placed therapy electrode 14a may also be integrated into or attached to the belt 50. By providing support in the form of a belt 50, for example, the device 10B can retain the heavier components on the lower torso of the patient in an bodily region more capable of supporting additional weight without disrupting a patient's balance or causing musculature soreness of the upper torso. In distributing weight in this way, the device 10B thereby encourages patient compliance with prescribed wear durations by avoiding weight-related discomfort.

Figure 3A:
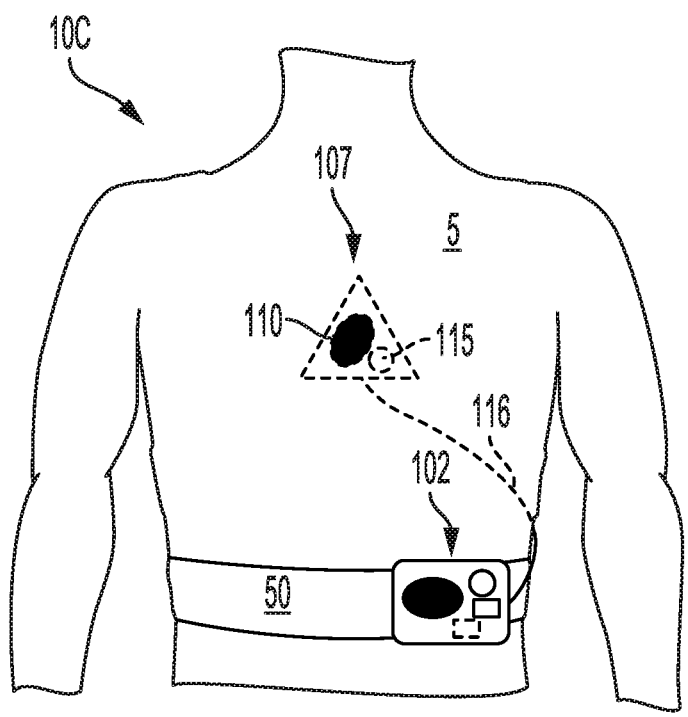
FIG. 3A depicts a schematic of an example wearable cardiac monitoring and treatment device including a wearable support and adhesively coupled portions.
Figure 3B:
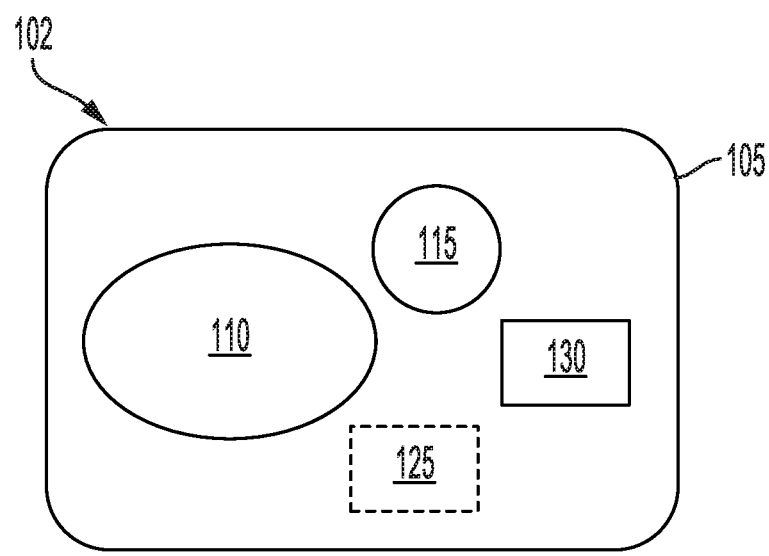
FIG. 3B depicts a plan view schematic of a portion of the example wearable cardiac monitoring and treatment device of FIG. 3A.
Figure 3C:
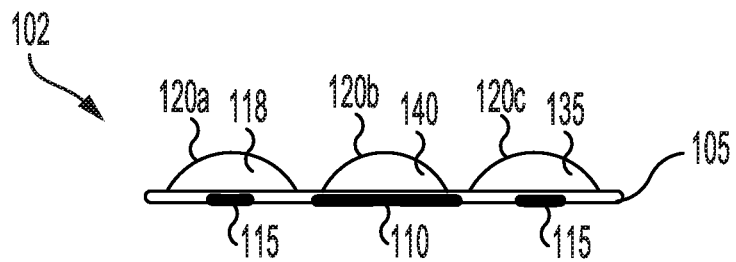
FIG. 3C depicts a side cross-section view of a portion of the example wearable cardiac monitoring and treatment device of FIG. 3B.

Such compliance can be further encouraged by minimizing volume and weight of one or more components to minimize or eliminate any skin irritation associated with surface area contact and/or weight-based forces. For example, as shown in FIGS. 3A through 3C, in embodiments, the device 10C includes a first assembly 102 secured by a belt 50 to a lower left anterior position on the torso 5 and a second assembly 107 in wired connection with the first assembly 102. The second assembly 107 can adhesively secure to an upper posterior torso position, generally between the shoulder blades of the patient. As shown in FIGS. 3B and 3C, the first assembly can include a first contoured pad 105 and one or more therapy electrodes 110 and/or a plurality of ECG sensing electrodes 115 integrated with the contoured pad 105. The first assembly can include a plurality of housings 120a, 120b, 120c, collectively referred to as housings 120. Each housing 120 is configured to form a watertight seal with the contoured pad 105. In certain implementations, the housings 120 can extend between around 1 cm and 5 cm from a surface of the contoured pad 105. The housings 120 can include at least an ECG acquisition and conditioning circuit, a therapy delivery circuit, a processor 118, one or more capacitors 135 and one or more batteries 140. In implementations, the second assembly 107 can include only relatively lighter components (e.g., the second assembly weighing around 10-500 grams) such as one or more therapy electrodes 110 and/or one or more ECG sensing electrodes 115 when compared to the first assembly 102.

Figure 4A:
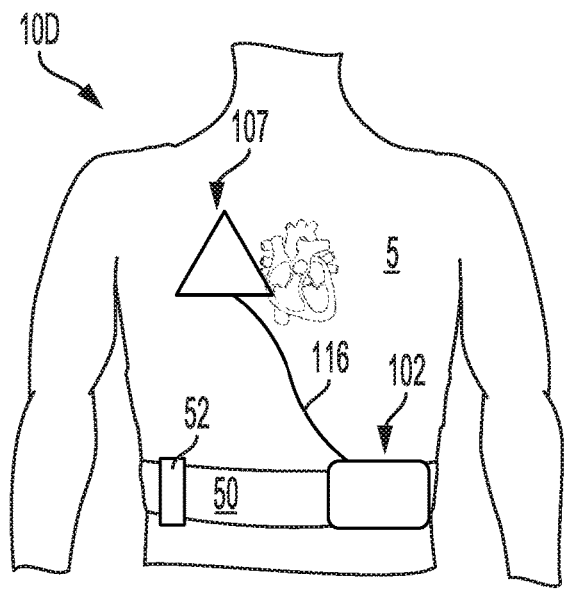
FIG. 4A depicts a schematic of an example wearable cardiac monitoring and treatment device including a wearable support and adhesively coupled portions in wired communication.
Figure 4B:
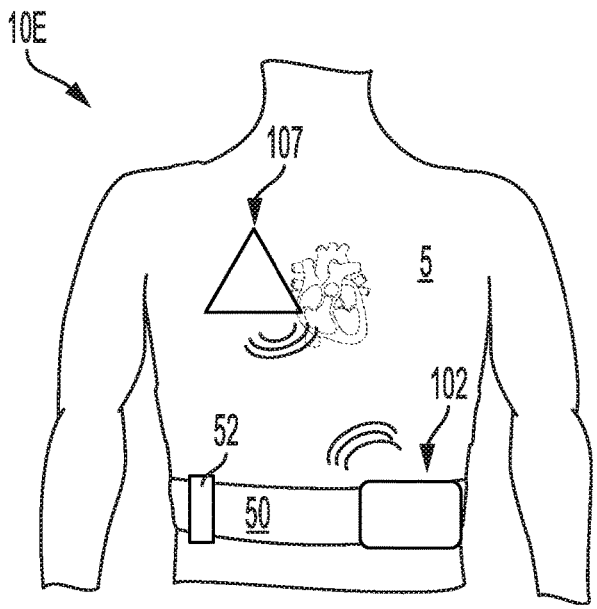
FIG. 4B depicts a schematic of an example wearable cardiac monitoring and treatment device including a wearable support and adhesively coupled portions in wireless communication.
Figure 4C:
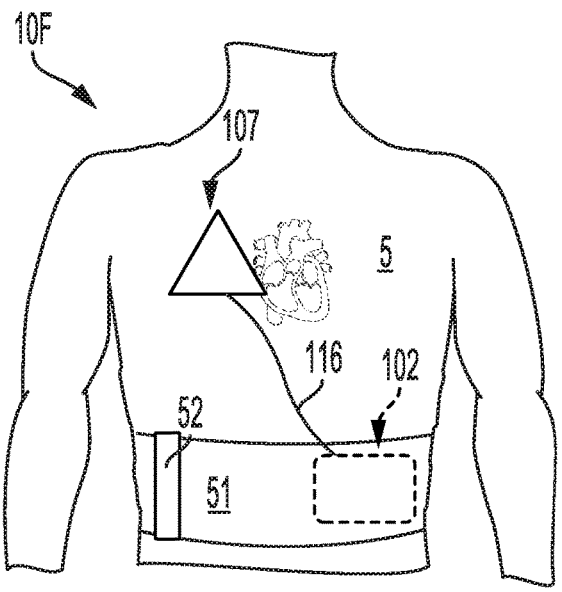
FIG. 4C depicts a schematic of an example wearable cardiac monitoring and treatment device including a wearable support and at least one adhesively coupled portion disposed between the wearable support and a torso of the patient.
Figure 4D:
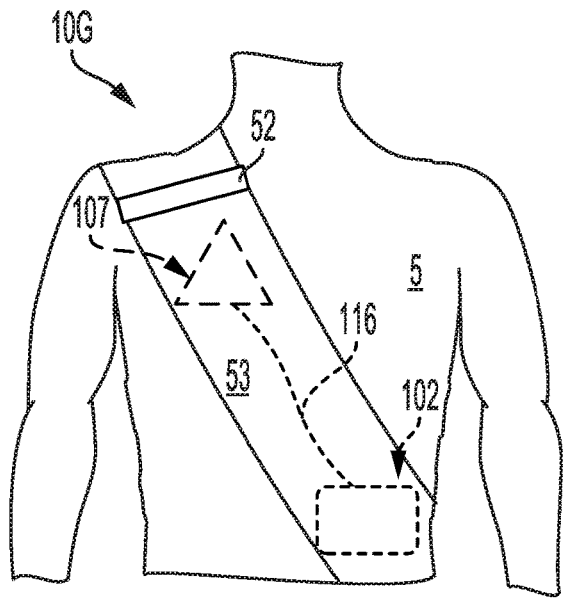
FIG. 4D depicts a schematic of an example wearable cardiac monitoring and treatment device including a wearable support and adhesively coupled portions disposed between the wearable support and a torso of the patient.

In embodiments, such as those of FIGS. 4A-D, the first and second assembly can both be placed on an anterior portion of the torso 5. The second assembly 107 of the device 10D can be placed on the torso 5 above the patient's right nipple and the first assembly 102 is placed on the left lateral side of the patient's torso 5 opposite placement of the second assembly 107. As shown in FIGS. 4A, 4C, and 4D, in embodiments the device 10D includes a first assembly 102 and second assembly 107 in wired connection. Alternatively, as shown in FIG. 4B, in embodiments the device 10D, 10F, 10G includes a first assembly 102 and a second assembly 107 in wireless communication, for example when the device is used for monitoring for a cardiac condition. In some examples, the wire 116 can be detachable and the device 10E can prompt the patient to attach the wire 116 to the first and second assemblies 102, 107 when the device 10E detects a cardiac condition requiring treatment.

In the embodiments of FIGS. 4A-B a wearable support can be a belt 50, or waistband, configured for supporting the first assembly 102 and relatively heavier components included therein (e.g., the first assembly weighing around 500 grams-10 kgs). In implementations, the belt 50 can include a tensioner 52 for tightening and/or loosening the belt 50 about the torso 5 of the patient. In implementations, the tensioner 52 can also fasten the belt 50 about the torso 5 of the patient, such a hook and loop fastener system or a ratchet strap and buckle assembly. In embodiments, the first assembly 102 can be disposed on the wearable support or integrated with the wearable support. For example, in FIGS. 4A-B, the first assembly 102 can form a linking portion of the belt 50 so that the sensors integrated with the contoured pad 105 contact the skin of the patient. In some embodiments, the first assembly 102 and/or second assembly 107 can be covered by the wearable support. For example, as indicated by the broken lines in FIGS. 4C-D, the support garment can be a belt 51 positioned on a lower torso region or a sash 53 extending diagonally across the torso 5 and covering the first assembly 102 and/or second assembly 107. In embodiments, the belt 51 and sash 53 can include a tensioner 52 configured for tightening the wearable support about the torso 5, adding compression force to the first assembly 102 and/or second assembly 107 and assisting with maintain contact of the first and second assemblies 102, 107 with the torso 5.

As described previously, in some examples, the second assembly 107 can include only relatively lighter components such as one or more therapy electrodes 110 and/or one or more ECG sensing electrodes 115. In alternative implementations, the second assembly 107 can include one or more of the heavier components (e.g., the second assembly weighing around 500 grams-10 kgs), such as one or more capacitors, batteries, and/or the therapeutic circuitry when compared to the first assembly 102. Providing additional wearable support, such as a sash 53 as shown in FIG. 4D, for example, can assist with retaining the relatively heavier second assembly 107 that includes heavier components, against an upper region of the torso 5. Providing such additional wearable support assists with preventing the second assembly 107 from pulling on the skin of the patient while adhesively attached.

In examples which will be subsequently described in further detail with regard to FIGS. 5A through 5C, the device 100 can include an adhesively attached first assembly 102 and an adhesively attached second assembly 107 without requiring wearable supports and/or garment-based support.

The adhesively coupled devices described herein may be configured for short term or long-term use. For example, a patient may be prescribed a short term device for the duration spanning between discharge from a hospital or an out-patient clinical visit and a follow-up medical appointment. In this regard, short-term wear durations may include periods of less than an hour (e.g., 10 minutes to about 60 minutes while in a medical office waiting room), or periods of 1 hour to about 24 hours, 1 hour to about 48 hours, 1 hour to about 72 hours, 1 hour to about 4 days, 1 hour to about a week, and 1 hour to about two weeks. In examples, short-term wear durations may include, for example, durations up to and including around 14 days, or durations up to and including around 30 days.

In another example scenario, a patient may be prescribed a long-term device following a medical appointment to protect the patient from life-threatening arrhythmias, while also collecting diagnostic information for additional, potentially more invasive procedures. In this scenario, such devices can be designed to be used by the patient for an extended period of time that may be greater than the short term duration described above. For example, long-term wear durations can include periods of around 1 month to around 3 months, or around 3 months to around 6 months. Accordingly, advantages of the configurations herein include providing physicians and caregivers with additional diagnostic and therapeutic options for treating patients in their care.

Because these devices require continuous operation and wear by patients to which they are prescribed, advantages of the implementations herein include use of comfortable, non-irritating, biocompatible adhesive and construction materials, and features designed to enhance patient compliance. Such compliance-inducing design features include, for example, device ergonomics, weight of the components and/or distribution of the weight, overall device shape, and inconspicuous appearance when worn under output garments, among others.

The example devices described herein are prescribed to be worn continuously and typically for a prescribed duration of time. For example, the prescribed duration can be a duration for which a patient is instructed by a caregiver to wear the device in compliance with device use instructions. As noted above, the prescribed duration may be for a short period of time until a follow up medical appointment (e.g., 1 hour to about 24 hours, 1 day to about 14 days, or 14 days to about one month), or a longer period of time (e.g., 1 month to about 3 months) during which diagnostics information about the patient is being collected even as the patient is being protected against cardiac arrhythmias. The prescribed use can be uninterrupted until a physician or other caregiver provides a specific prescription to the patient to stop using the wearable medical device. For example, the wearable medical device can be prescribed for use by a patient for a period of at least one week. In an example, the wearable medical device can be prescribed for use by a patient for a period of at least 30 days. In an example, the wearable medical device can be prescribed for use by a patient for a period of at least one month. In an example, the wearable medical device can be prescribed for use by a patient for a period of at least two months. In an example, the wearable medical device can be prescribed for use by a patient for a period of at least three months. In an example, the wearable medical device can be prescribed for use by a patient for a period of at least six months. In an example, the wearable medical device can be prescribed for use by a patient for an extended period of at least one year.

A sudden cardiac arrest or other arrhythmia condition can strike at any time and with little warning. Every patient is encouraged to comply with the device use guidelines, including wearing the device at all times during a prescribed duration, including while showering or sleeping. To improve patient compliance with these guidelines, the devices described herein are lightweight, comfortable, and compact so that they may be concealed under the patient's clothing. Moreover, the devices are configured to allow for uncomplicated application and adherence to the skin of the body of the patient. In some implementations described herein, the devices include various features that promote comfort while continuing to protect the patient from adverse cardiac events. These features can be tailored in accordance with patient comfort preference and can include durable adherence, ease of application and removal, and inconspicuous appearance.

The devices herein are configured to be adhesively coupled to a torso of a patient for short term and long-term durations. The devices include biocompatible adhesives, such as pressure-sensitive adhesives having tack, adhesion, and cohesion properties suitable for use with a medical device applied to skin for short term and long-term durations. These pressure sensitive adhesives can include polymers such as acrylics, rubbers, silicones, and polyurethanes having a high initial tack for adhering to skin. These pressure sensitive adhesives also maintain adhesion during showering or while a patient is perspiring. The adhesives also enable removal without leaving behind uncomfortable residue. For example, such an adhesive can be a rubber blended with a tackifier.

In any of the previously presented or foregoing examples, the devices herein include low skin-irritation adhesives. In embodiments, the device may be worn continuously by a patient for a long-term duration (e.g., duration of at least one week, at least 30 days, at least one month, at least two months, at least three months, at least six months, and at least one year) without the patient experiencing significant skin irritation. For example, a measure of skin irritation can be based on skin irritation grading of one or more as set forth in Table C.1 of Annex C of American National Standard ANSI/AAMI/ISO 10993-10:2010, reproduced here in the entirety:

TABLE C.1

Human Skin irritation test, grading scale

| Description of response | Grading |
|---|---|
| No reaction | 0 |
| Weakly positive reaction (usually characterized by mild erythema and/or dryness across most of the treatment site) | 1 |
| Moderately positive reaction (usually distinct erythema or dryness, possibly spreading beyond the treatment site) | 2 |
| Strongly positive reaction (strong and often spreading erythema with oedema and/or eschar formation) | 3 |

Table 1.

The skin irritation grading of one represents a weakly positive reaction usually characterized by mild erythema and/or dryness across most of the treatment site. In one implementation, a measure of skin irritation can be determined by testing on human subjects in accordance with the method set forth in American National Standard ANSI/AAMI/ISO 10993-10:2010, by applying sample patches of the adhesive device to treatment sites for up to four hours, and, in the absence of skin irritation, subsequently applying sample patches to treatment sites for up to 24 hours. The treatment sites are examined for signs of skin irritation, and the responses are scored immediately after patch removal and at time intervals of $(1\pm0.1)$ h to $(2\pm1)$ h, $(24\pm2)$ h, $(48\pm2)$ h and $(72\pm2)$ h after patch removal. In another implementation, a patient may wear the adhesive device as instructed for a duration of $(24\pm2)$ hours, and if the patient's skin shows no reaction at the end of this duration, the adhesive device is rated as a skin irritation grading of zero.

In addition to biocompatible adhesives, such short term and long-term wear devices include a plurality of sensing electrodes that are disposed on the patient's body and configured to monitor cardiac signals such as electrocardiogram (ECG) signals. The devices, therefore, determine an appropriate treatment for the patient based on the detected cardiac signals and/or other physiological parameters prior to delivering a therapy to the patient. The devices then cause one or more therapeutic shocks, for example, defibrillating and/or pacing shocks, to be delivered to the body of the patient. The wearable medical device includes a plurality of therapy electrodes, at least one of which is integrated with a contoured pad as described in detail herein. The plurality of therapy electrodes are disposed on the patient's body and configured to deliver the therapeutic shocks. In some implementations, the devices can also be configured to allow a patient to report his/her symptoms including one or more skipped beat(s), shortness of breath, light headedness, racing heart, fatigue, fainting, and chest discomfort. Device implementations and example features are disclosed herein to improve the ergonomics of such a wearable medical device.

In implementations, the devices include one or more contoured pads configured to be adhesively secured to the torso of the patient. One or more energy storage units are operably connected to a therapy delivery circuit. The energy storage units as well as a therapy delivery circuit are housed within at least one housing configured to form a watertight seal with the contoured pad. In some implementations, a plurality of housings can be disposed on a plurality of segments of the contoured pad. Each of the plurality of housings can include different portions of the device circuitry, such as, ECG acquisition and conditioning circuit(s), therapy delivery circuit(s), energy storage unit(s), processor(s), power source(s) and the like. The energy storage units are configured to store energy for at least one therapeutic pulse (e.g., a defibrillation pulse). The therapy delivery circuit is configured to cause the delivery of the at least one therapeutic pulse via the plurality of therapy electrodes. In implementations, the energy storage units are electrically coupled to the plurality of therapy electrodes (e.g., by a printed circuit board trace, a flex circuit, or a direct contact connection).

As described above, implementations of the wearable medical device described herein are capable of continuous use by patients during either the short term or long-term wear duration. Such continuous use can be substantially continuous or nearly continuous in nature. During substantially continuous or nearly continuous use, the wearable medical device may be continuously used except for sporadic periods during which the use temporarily ceases (e.g., while the patient is refit with a new and/or a different device, while the battery is charged and/or changed, etc.). Such substantially continuous or nearly continuous use as described herein may nonetheless qualify as continuous use. For example, the continuous use can include continuous wear or attachment of the wearable medical device to the patient. In implementations, one or more of the electrodes are continuously attached to the patient as described herein during both periods of monitoring and periods when the device may not be monitoring the patient but is otherwise still worn by or otherwise attached to the patient. Continuous use can include continuously monitoring the patient while the patient is wearing the device for cardiac-related information (e.g., electrocardiogram (ECG) information, including arrhythmia information, cardiac vibrations, etc.) and/or non-cardiac information (e.g., blood oxygen, the patient's temperature, glucose levels, tissue fluid levels, and/or pulmonary vibrations). For example, the wearable medical device can carry out its continuous monitoring and/or recording in periodic or aperiodic time intervals or times (e.g., every few minutes, every few hours, once a day, once a week, or other interval set by a technician or prescribed by a caregiver). Alternatively or additionally, the monitoring and/or recording during intervals or times can be triggered by a user action or another event.

As noted above, the wearable medical device can be configured to monitor other physiologic parameters of the patient in addition to cardiac related parameters. For example, the wearable medical device can be configured to monitor, for example, pulmonary vibrations (e.g., using microphones and/or accelerometers), breath vibrations, sleep related parameters (e.g., snoring, sleep apnea), and tissue fluids (e.g., using radio-frequency transmitters and sensors), among others.

Figure 5A:
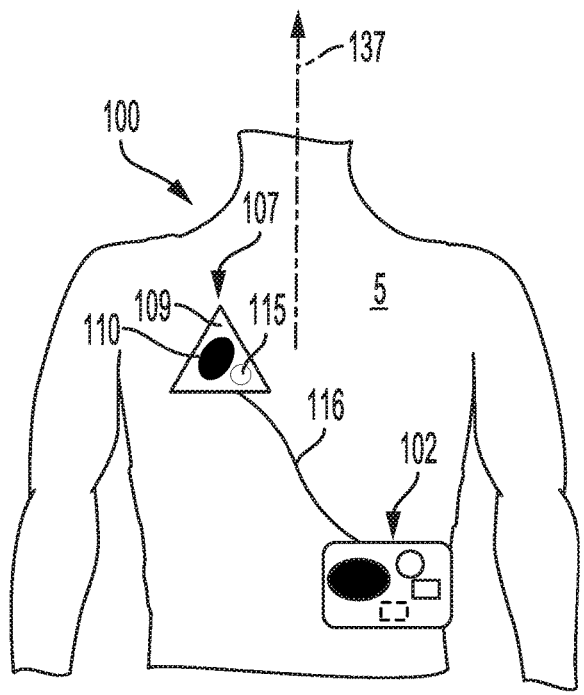
FIG. 5A depicts a schematic of an example adhesively coupled wearable cardiac monitoring and treatment device including anterior mounted first and second assemblies.
Figure 5B:
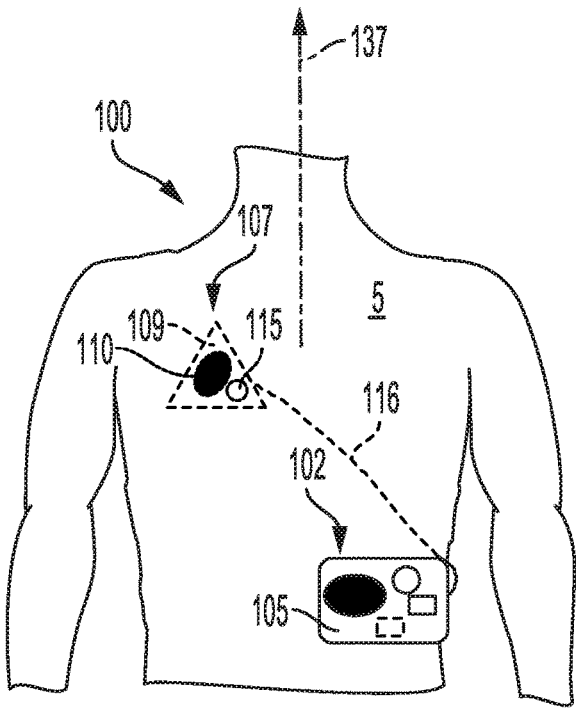
FIG. 5B depicts a schematic of an example adhesively coupled wearable cardiac monitoring and treatment device including one posterior mounted first assembly and an anterior mounted second assembly.
Figure 5C:
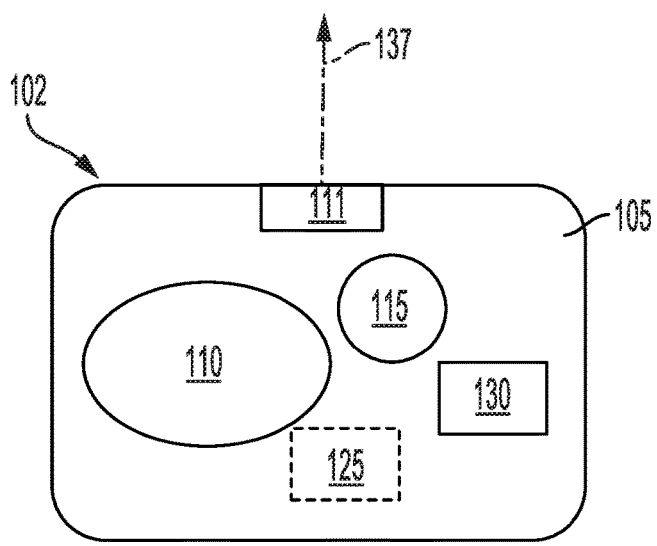
FIG. 5C depicts a schematic of an example of a portion of the adhesively coupled wearable cardiac monitoring and treatment device of FIGS. 5A and 5B.

As will be described in detail below, FIGS. 5A-C depict an example monitoring and treatment device 100 held on a patient's torso only by an adhesive coupling, and FIGS. 4A-D, 12A-B, 13A-C, and 14 relate to adhesively coupled monitoring and treatment devices 10D-G, 800A-D, 1000 including one or more wearable supports.

Figure 6:
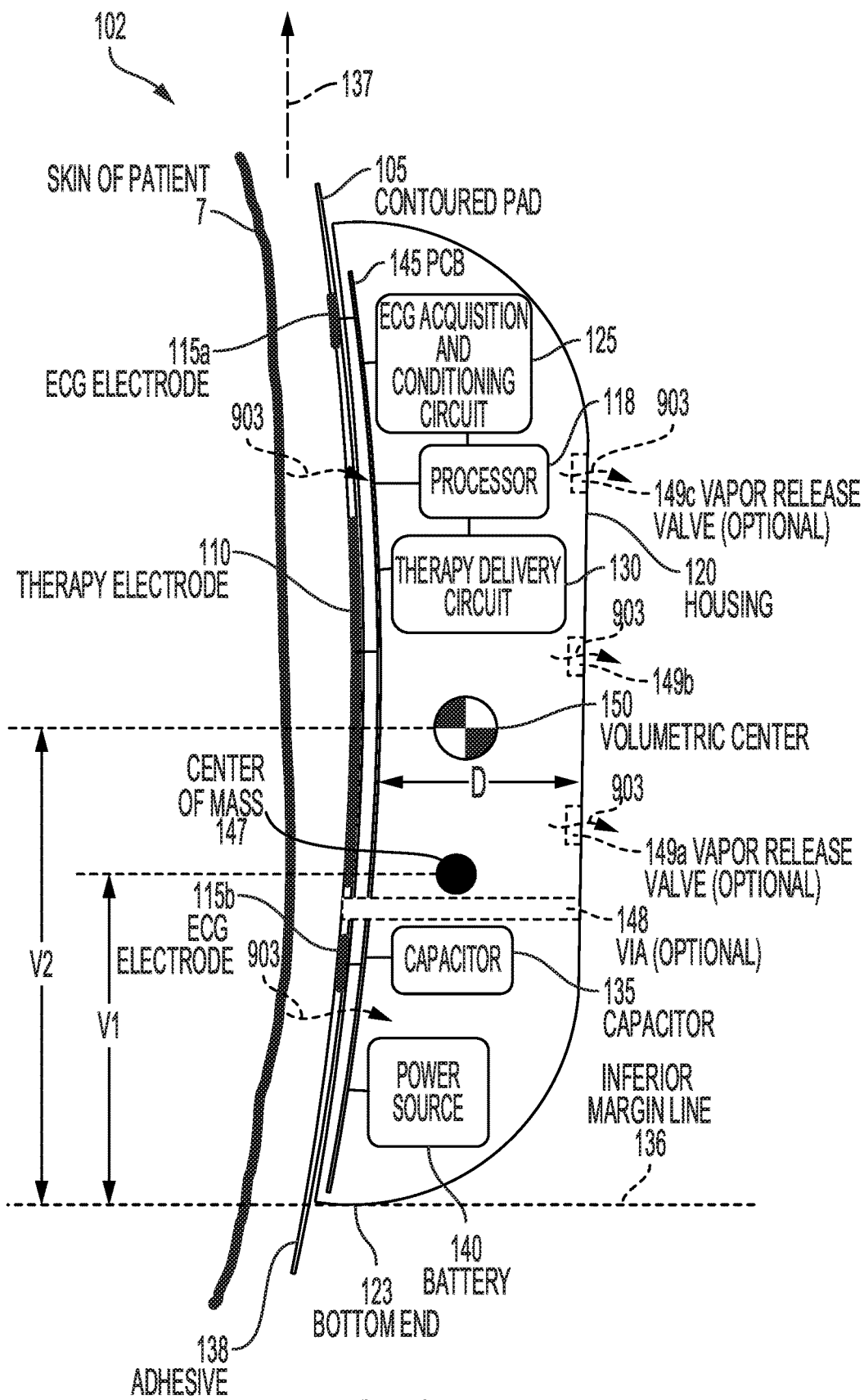
FIG. 6 depicts a side cross-section schematic of an example wearable cardiac monitoring and treatment device.

An example adhesively coupled monitoring and treatment device 100 is shown in FIGS. 5A-B. As shown, the device 100 is external, ambulatory, and adhesively coupled to a patient. The medical device 100 is an external or non-invasive medical device, which, for example, is located external to the body of the patient and configured to provide transcutaneous therapy to the body. The device 100 is an ambulatory medical device, which, for example, is capable of and designed for moving with the patient as the patient goes about his or her daily routine. The device 100 includes a first assembly 102 that includes a contoured pad 105 configured to be adhesively coupled to a torso 5 of a patient. In implementations, a plurality of therapy electrodes and/or a plurality of ECG sensing electrodes can be integrated with the contoured pad. Further, as shown in FIG. 6 the device 100 can include a housing 120 configured to form a watertight seal with the contoured pad 105. In certain implementations, the housing 120 can extend between around 1 cm and 5 cm from a surface of the contoured pad. The housing can include at least an ECG acquisition and conditioning circuit, a therapy delivery circuit, and a processor. For example, the processor can analyze the ECG signal of the patient received and conditioned via the ECG acquisition and conditioning circuit and detect one or more treatable arrhythmias. The processor can cause the therapy delivery circuit to deliver at least one defibrillation pulse to the patient on detecting the one or more treatable arrhythmias. As described in further detail below, the device 100 includes components with particular physical dimensions, weights, and functional properties that in combination cause the overall weight of the device 100 to be in a range of 250 grams to 2,500 grams while enabling the device 100 to function as a monitoring and treatment device.

In examples, the first assembly 102 can be coupled to a second assembly 107 that includes a second, different contoured pad 109 as shown in FIGS. 5A-B, and as will be subsequently described in further detail. For example, the second assembly 107 can be configured to be located at an upper right anterior position of the patient's torso 5 as shown in FIG. 5A. In other examples, the second assembly 107 can be configured to be located at an upper posterior position of the patient's torso 5, such as the upper right posterior position, as shown in FIG. 5B. Although the implementations of FIGS. 5A and 5B depict a substantially rectangular shaped first assembly 102 and a triangle shaped second assembly, the shapes of the first and second assemblies can be any shape including, for example, a polygon, a square, a circle, an oval, an octagon, a trefoil, a trapezoid, a polygon, or a non-polygon shape custom-tailored to a patient's contours and/or preferences. In implementations, the second assembly 107 can include one or more of the components and/or materials described with regard to implementations of the first assembly 102, such as the components and materials described with regard to the implementations of FIGS. 6-8.

The contoured pad 105 is configured to be adhesively coupled to a torso 5 of a patient. The contoured pad 105 is formed from a flexible material and is configured to conform to a unique curvature of a region of the torso 5 of the patient. Additionally or alternatively, as shown schematically in FIG. 3C, the contoured pad 105 can include a plurality of segments separated by a flexible material to conform the contoured pad 105 to the curvature of a region of the torso 5 to which it is applied. The contoured pad 105 can be configured to conform with a curvature of a portion of the patient's torso 5, such as lower portion of the torso, an upper anterior portion of the torso, upper posterior portion of the torso, or one or more lateral portions of the torso. In implementations including a contoured pad 105 formed from a conforming material and/or segments, the contoured pad could accommodate various body shapes and sizes and also shape changes associated with movement of the patient's body. For example, the contoured pad 105 could accommodate stretching, expansion, and contraction of a lower region of the torso 5 while a patient stands, walks, sits, or lies prone.

In implementations, the contoured pad 105 can be a sized to accommodate various body sizes. In some implementations, the contoured pad 105 can be manufactured in various sizes accommodating a range of body sizes. The particular shape and size of the contoured pad 105 can be pre-configured or uniquely customized for the patient. For example, various body size measurements and/or contoured mappings may be obtained from the patient, and a uniquely tailored contoured pad 105 may be 3D printed from, for example, any suitable thermoplastic (e.g., ABS plastic). The contoured pad 105 therefore accommodates variable patient sizes and/or contours, and/or some or all portions of the contoured pad can be customized to fit to a patient's particular body size and contour.

In examples, the patient may apply the contoured pad 105 in a uniquely preferred orientation and location. Enabling a patient, in consultation with their caregiver, to place the device 100 in a comfortable location and orientation encourages patient compliance with continuous wear throughout the prescribed duration of wear. For example, the pad 105 can be positioned by a caregiver or physician on the torso 5 of the patient in a first location at the start of the prescribed duration of wear. At least one of the patient, caregiver, and physician may relocate the contoured pad 105 to a second location overlapping with, tangential to, adjacent to, or apart from the first location but within a prescribed region of the torso. For example, the first assembly 102 can be placed initially on a lower anterior region of the torso, along the line of the bottom of a patient's rib cage for comfort and to minimize the appearance of any bulges in clothing worn over the device 100. A patient, caregiver, or physician may remove and re-adhere the contoured pad 105 one inch, for example, in any lateral and/or rotational direction. This provides the patient's skin with an opportunity to breath and regenerate (e.g., slough) and reduces the effects of skin irritation that may be caused by adhesives. By keeping the contoured pad in the region of initial application, the first assembly 102 of the device 100 continues to function in conjunction with the second assembly 107, which is positioned relative to the first assembly and with particular attention to the shock vector traveling between the assemblies 102, 107 and through the heart.

In embodiments, the contoured pad 105 is designed to be durable, flexible, and breathable so as to allow perspiration to evaporate. In embodiments, the contoured pad 105 is non-irritating when contacting skin as described above with regard to skin irritation grading as set forth in Table C.1 of Annex C of American National Standard ANSI/AAMI/ISO 10993-10:2010, as previously presented. In examples, the contoured pad 105 is generally non-conductive, flexible, water vapor-permeable, and substantially liquid-impermeable or waterproof. The non-conductive flexible, water-vapor permeable contoured pad 105 may comprise or consist of polyurethane, such as TEGADERM polyurethane film (available from 3M), OPSITE polyurethane film (available from Smith & Nephew, London, United Kingdom), or HYDROFILM polyurethane film (available from Hartman USA, Rock Hill, SC). In other examples, the contoured pad 105 can comprise or consist of at least one of neoprene, thermoformed plastic, or injection molded rubber or plastic, such as silicone or other biocompatible synthetic rubber. In examples, the contoured pad 105 is a laminated pad including a waterproof or water resistant layer applied to a relatively more rigid plastic or rubber layer configured to provide structural support for a housing and electronic components disposed therein. In examples the contoured pad 105 is perforated to aid in moisture evaporation from the skin.

In embodiments, the device 100 can include a conductive adhesive layer 138, as indicated in FIG. 6. As described in U.S. Pat. No. 9,867,976, titled "LONG-TERM WEAR ELECTRODE," issued on Jan. 16, 2018 (hereinafter the "'976 Patent"), which is hereby incorporated herein by reference in its entirety, a water-vapor permeable conductive adhesive material can be, for example, the flexible, water vapor-permeable, conductive adhesive material can comprise a material selected from the group consisting of an electro-spun polyurethane adhesive, a polymerized microemulsion pressure sensitive adhesive, an organic conductive polymer, an organic semi-conductive conductive polymer, an organic conductive compound and a semi-conductive conductive compound, and combinations thereof. In an example, a thickness of the flexible, water vapor-permeable, conductive adhesive material can be between 0.25 and 100 mils. In another example, the water vapor-permeable, conductive adhesive material can comprise conductive particles. In implementations, the conductive particles may be microscopic or nano-scale particles or fibers of materials, including but not limited to, one or more of carbon black, silver, nickel, graphene, graphite, carbon nanotubes, and/or other conductive biocompatible metals such as aluminum, copper, gold, and/or platinum.

FIG. 6 depicts the first assembly 102, which is a portion of the device 100. The device 100 includes a contoured pad 105 and a housing 120 configured to form a watertight seal with the contoured pad 105. Referring now to FIG. 6, the device 100 includes at least one of a plurality of therapy electrodes 110 integrated with the contoured pad 105. Example therapy electrodes 110 include, for example, conductive metal electrodes, such as those made of stainless steel, tin or aluminum, a conductive ink, or a conductive polymer. The device 100 can also include at least one of a plurality of ECG sensors 115 integrated with the contoured pad 105. In the implementation of FIG. 6, two ECG sensors 115a and 115b are shown to be integrated with the contoured pad 105. In examples, the ECG sensors 115 monitor a patient's ECG information. As described in detail in subsequent examples, the ECG sensors 115 can be non-polarizable ECG electrodes (e.g., clinical grade Ag/AgCl electrodes) or polarizable electrodes (e.g., electrodes having a metal substrate with an oxide layer, such as a $Ta_2O_5$ coating) configured to measure changes in a patient's electrophysiology to measure the patient's ECG information. Example ECG sensors 115 include tantalum pentoxide electrodes, as described in, for example, U.S. Pat. No. 6,253,099 entitled, "Cardiac Monitoring Electrode Apparatus and Method," the entire content of which is incorporated herein by reference. In implementations, the ECG sensors 115 may be made of a core plastic or metal substrate element that is coated with a thick-film polymeric compound filled with a conductive Ag/Ag/Cl metallic filler.

In some examples, as indicated FIG. 6, at least one therapy electrode 110 and one or more ECG sensors 115 are formed within the contoured pad 105 such that a skin contact surface of each component is coplanar with or protrudes from the patient contact face of the contoured pad 105. In examples, the therapy electrode 110 and the ECG sensors 115 are disposed on the patient contact face of the contoured pad 105. In some implementations, the therapy electrode 114 and ECG sensors 115 are metallic plates (e.g. stainless steel) or substrates that are formed as permanent portions of the device 100. A metallic plate or substrate can be adhered to the contoured pad 105, for example, by a polyurethane adhesive or a polymer dispersion adhesive such as a polyvinyl acetate (PVAc) based adhesive, or other such adhesive. In examples, the plurality of ECG sensors 115 are a plurality of dry ECG sensing electrodes. In examples, the ECG sensors 115 are flexible, dry surface electrodes such as, for example, conductive polymer-coated nano-particle loaded polysiloxane electrodes mounted to the contoured pad 105. In some examples, the ECG sensors 115 are flexible, dry surface electrodes such as, for example silver coated conductive polymer foam soft electrodes mounted to the contoured pad 105. In examples, the ECG sensors 115 are screen printed onto the contoured pad 105 with a metallic ink, such as a silver-based ink. In implementations, each of the therapy electrodes 110 has a conductive surface adapted for placement adjacent the patient's skin. In some implementations, the therapy electrodes 110 can include an impedance reducing material and/or mechanism as subsequently described.

In implementations, the at least one therapy electrode 110 and at least one ECG sensor 115 are manufactured as integral components of the contoured pad 105. For example, the therapy electrode 110 and/or the ECG sensor 115 can be formed of the warp and weft of a fabric forming at least a layer of the contoured pad 105. In implementations, the therapy electrode 110 and/or the ECG sensors 115 are formed from conductive fibers that are interwoven with non-conductive fibers of the fabric.

The device 100 includes an ECG acquisition and conditioning circuit 125 disposed within the at least one housing 120 and electrically coupled to the plurality of ECG sensors 115 to provide at least one ECG signal of the patient. In examples, the ECG acquisition and conditioning circuit 125 includes a signal processor configured to amplify, filter, and digitize the cardiac signals prior to transmitting the cardiac signals to a processor 118 of the device 100. The ECG sensors 115, therefore, can transmit information descriptive of the ECG signals to a sensor interface via the ECG acquisition and conditioning circuit 125 for subsequent analysis.

In examples, as shown in FIG. 6, a therapy delivery circuit 130 is disposed within the at least one housing 120 and configured to deliver one or more therapeutic pulses to the patient through the plurality of therapy electrodes 110 of the device 100. In examples, the processor 118 is disposed within the at least one housing 120 and is coupled to the therapy delivery circuit 130. The processor 118 is configured to analyze the ECG signal of the patient and detect one or more treatable arrhythmias based on the at least one ECG signal. The processor 118 is configured to cause the therapy delivery circuit 130 to deliver at least one defibrillation pulse to the patient on detecting the one or more treatable arrhythmias.

In examples, one or more printed circuit boards 145 connect various circuitry and hardware components (e.g., processor 118, therapy delivery circuit 130, therapy electrodes 110, ECG acquisition and conditioning circuit 125, ECG sensing electrodes 115, etc.) of the first assembly 102.

Figure 7:
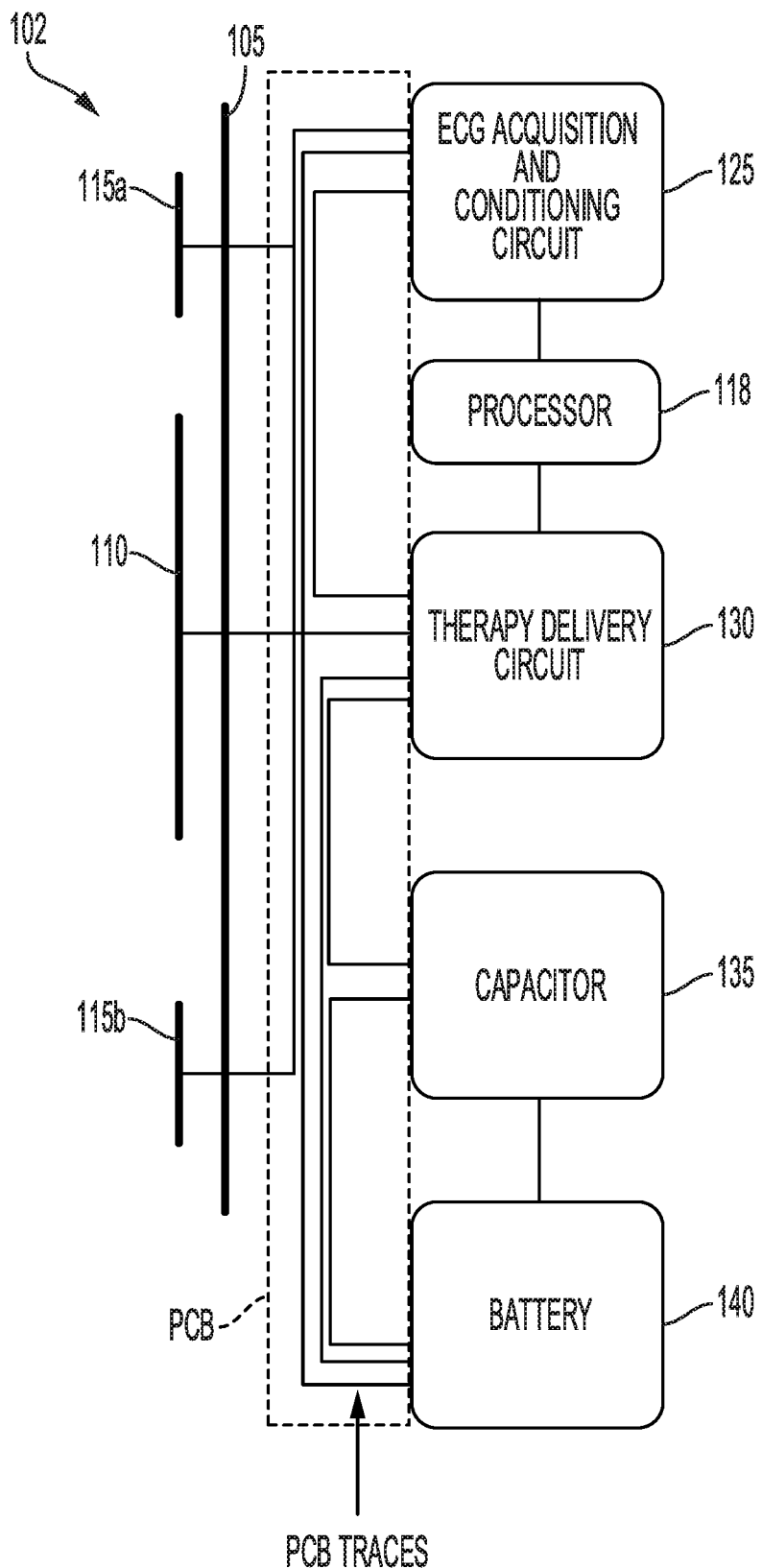
FIG. 7 depicts an example schematic of electrically connected components of wearable cardiac monitoring and treatment device.

For example, as shown in the schematic of FIG. 7, the printed circuit board 145 can route signals between the therapy delivery circuit 130 and the therapy electrodes 110 and the ECG acquisition and conditioning circuit 125 and the ECG sensing electrodes 115. In implementations of the contoured pad 105 comprising a plurality of segments separated by a flexible material, the one or more circuit boards 145 can be apportioned among some or all of the plurality of segments and, in examples, may be be electrically interconnected by one or more wires and/or flexible traces or cables.

Continuing with the description of the implementations of the device 100 of FIGS. 5-6, in implementations, the therapy delivery circuit 130 is operatively connected to one or more capacitors 135. In implementations the one or more capacitors 135 is a plurality of capacitors (e.g., three, four or more capacitors) that can be switched into a series connection during discharge for a defibrillation pulse. For example, four capacitors of approximately 650 g can be used. In one implementation, the capacitors can have between 200 to 2500 volt surge rating and can be charged in approximately 5 to 30 seconds from a battery 140 depending on the amount of energy to be delivered to the patient. Additional implementations of capacitor properties and arrangement within the device 100 are provided herein in subsequent sections.

For example, each defibrillation pulse can deliver between 60 to 400 joules (J) of energy. In some implementations, the defibrillating pulse can be a biphasic truncated exponential waveform, whereby the signal can switch between a positive and a negative portion (e.g., charge directions). An amplitude and a width of the two phases of the energy waveform can be automatically adjusted to deliver a predetermined energy amount.

In implementations, the therapy delivery circuit 130 includes, or is operably connected to, circuitry components that are configured to generate and provide the therapeutic shock. As will be described in detail subsequently with regard to implementations of the device 100, the circuitry components include, for example, resistors, one or more capacitors 135, relays and/or switches, an electrical bridge such as an H-bridge (e.g., an H-bridge circuit including a plurality of switches, (e.g. insulated gate bipolar transistors or IGBTs, silicon carbide field effect transistors (SiC FETs), metal-oxide semiconductor field effect transistors (MOSFETS), silicon-controlled rectifiers (SCRs), or other high current switching devices)), voltage and/or current measuring components, and other similar circuitry components arranged and connected such that the circuitry components work in concert with the therapy delivery circuit 130 and under control of one or more processors (e.g., processor 118) to provide, for example, one or more pacing or defibrillation therapeutic pulses.

As introduced previously, at least one housing 120 forms a watertight seal with the contoured pad 105. In examples, such as that of FIG. 6, various circuitry and hardware components (e.g., processor 118, therapy delivery circuit 130, therapy electrodes 110, ECG acquisition and conditioning circuit 125, ECG sensing electrodes 115, PCB 145, etc.) are within a compartment defined by the at least one housing 120 and the contoured pad 105. The housing 120 protects the components thereunder from external environmental impact, for example damage associated with water ingress. Preventing such ingress protects the electronic components of the device 100 from short-circuiting or corrosion of moisture-sensitive electronics, for example, when a patient wears the device while showering. Such features may also protect from other liquid and solid particle ingress.

Figure 9A:
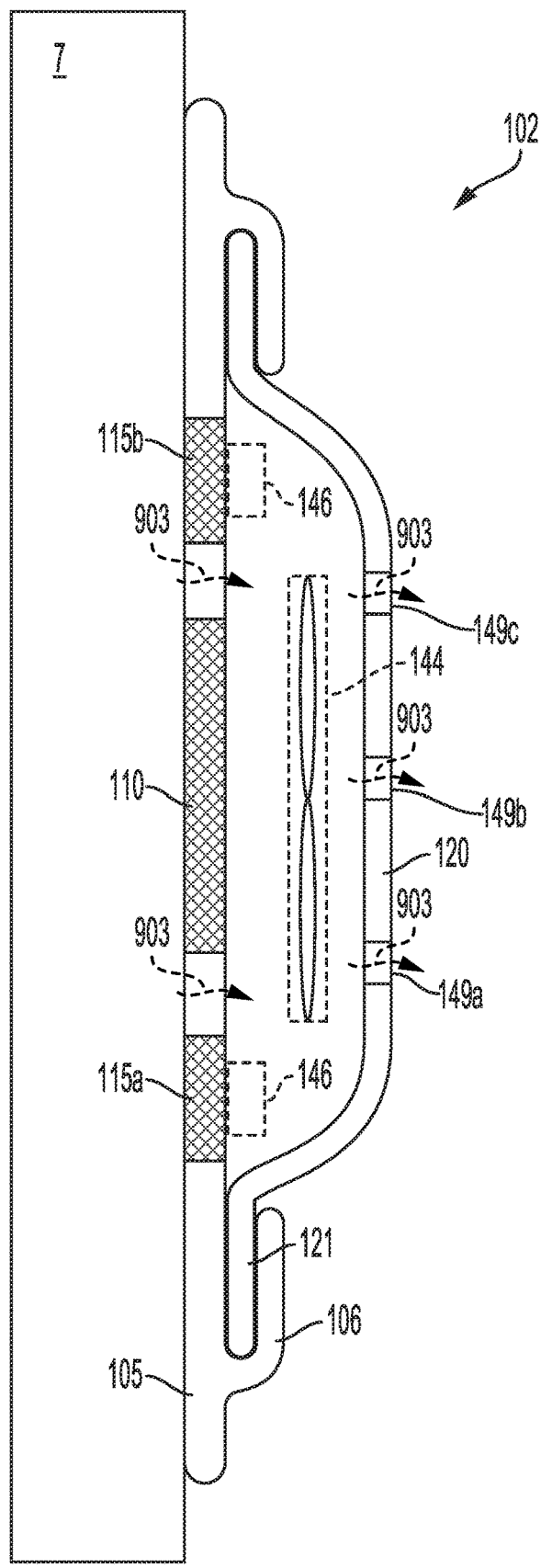
FIG. 9A depicts a side cross-section schematic of an example adhesive pad assembly of an example wearable cardiac monitoring and treatment device.

In examples, the contoured pad 105 includes one or more receptacles for receiving the at least one housing 120 in a watertight mating. In examples, such as that of FIG. 9A, the one or more receptacles comprise a sealing lip 106, and the sealing lip 106 can engage a top surface of the at least one housing 120. In implementations, the sealing lip 106 comprises an elastomeric waterproof material. For example, the one or more receptacles can include a rubber or silicone sealing lip 106 formed integrally with the contoured pad 105 for receiving a flange of the housing in a compression fit seal. For example, the sealing lip 106 and contoured pad 105 can be injection molded as a monolithic structure. In examples, the at least one housing 120 can further include a peripheral flange 121, and the sealing lip 106 securely receives the peripheral flange 121 in a watertight mated configuration. In examples, the housing 120 or one or more of a plurality of housings are removable and/or replaceable. The sealing lip 106 stretches when the housing 120 is pulled away from the contoured pad 105, allowing the housing 120 to be pulled free of the sealing lip 106. Because the sealing lip 106 is elastomeric, the deformation is not permanent, and the sealing lip 106 retracts to a resting state for again receiving the housing 120 and/or plurality of housings in a sealed configuration. In other implementations, housing 120 can be heat welded to the contoured pad 105. In other implementations, the housing 120 can be locked onto the contoured pad 105 and held in compression with a spring loaded clamp. In some or all implementations, the housing and/or contoured pad can included therebetween a deformable waterproof grommet, such as a resilient silicone seal around the perimeter of the interface between the housing and the contoured pad 105.

In addition to forming a watertight seal with the contoured pad, in some examples, the at least one housing 120 is water-resistant and/or coated with a water-resistant coating (e.g., an epoxy coating). Thereby, the device 100 can be worn in the shower without damaging the electrical components disposed within the housing 120. Additionally or alternatively, in implementations at least one of the plurality of ECG sensors 115, the plurality of therapy electrodes 110, and one or more electrical components of the device (e.g. capacitors 135, therapy delivery circuit 130, processor 118) are housed in one or more water resistant housings 120, or enclosures.

Example implementations of water-resistant housings 120 protect against liquid ingress in accordance with one or more scenarios as set forth in Table 2:

TABLE 2

| Protection Against | Effective Against (e.g. shall not impact normal operation of the medical device as described herein) |
|---|---|
| Dripping water | Falling drops of dripping water on the medical device housing, e.g., water dripping on the housing at a rate 1 mm per minute for a period of around 10 minutes. |
| Spraying water | Spray of water falling on the medical device housing at any angle up to 60 degrees from vertical. |

TABLE 2-continued

| Protection Against | Effective Against (e.g. shall not impact normal operation of the medical device as described herein) |
|---|---|
| Splashing of water | Water splashing against the housing from any direction. |
| Water jets | Water projected by a nozzle (e.g., a nozzle of 6.3 mm diameter) against the housing from any direction |
| Powerful water Jets | Water projected in powerful jets (e.g., a nozzle of 12.5 mm diameter spraying water at a pressure of 100 kPa at a distance of 3 m) against the housing from any direction |
| Immersion, up to 1 m depth | The housing is immersed in water at a depth of up to 1 meter. |
| Immersion, 1 m or more depth | The housing is immersed in water at a depth of 1 meter or more. |
| Powerful high temperature water jets | The housing is sprayed with a high pressure (e.g. 8-10 MPa), high temperature (e.g. 80 degrees Celsius) spray at close range. |

In some implementations, the at least one housing 120 is water-resistant and has a predetermined ingress protection rating complying with one or more of the rating levels set forth in IEC standard 60529. The liquid Ingress Protection rating can be one or more of any level (e.g., levels 3 to 9) in which rating compliance tests are specified in the standard. For example, to have a liquid ingress protection rating level of six, the at least one housing 120 the device 100 shall protect against ingress of water provided by a powerful water jet. The powerful water jet test requires that the housing 120 is sprayed from all practicable directions with a stream of water from a test nozzle having a 12.5 mm diameter. Water sprays for 1 minute per square meter for a minimum of three minutes at a volume of 100 liters per minute (+/−5 percent) so that a core of the stream of water is a circle of approximately 120 mmm in diameter at a distance of 2.5 meters from the nozzle. For example, to have a rating level of 7, ingress of water shall not be possible when the housing 120 is completely immersed in water at a depth between 0.15 m and 1 m so that the lowest point of the housing 120 with a height less than 850 mm is located 1000 mm below the surface of the water and the highest point of a housing with a height less than 850 mm is located 150 mm below the surface of the water. The housing 120 is immersed for a duration 30 minutes, and the water temperature does not differ from that of the housing by more than 5K. Table 3 provides the rating levels and tests for liquid Ingress Protection in accordance with IEC standard 60529:

TABLE 3

| Rating Level | Degree of Protection | | Test conditions, see |
|---|---|---|---|
| | Brief Description | Definition | IEC 60529 section |
| 0 | Non-protected | — | — |
| 1 | Protected against vertically falling water drops | Vertically falling drops shall have no harmful effects | 14.2.1 |
| 2 | Protected against vertically falling water drops when housing tilted up to 15 degrees | Vertically falling drops shall have no harmful effects when the housing is tilted at any angle up to 15 degrees on either side of the vertical | 14.2.2 |
| 3 | Protected against spraying water | Water sprayed at an angle up to 60 degrees on either side of the vertical shall have no harmful effects | 14.2.3, including, for example, spraying water on the housing at 60 degrees from vertical at a water flow rate of 10 liters/min for at least 5 minutes |
| 4 | Protected against splashing water | Water splashed against the housing from any direction shall have no harmful effects | 14.2.4, including, for example, spraying water on the housing at 180 degrees from vertical at a water flow rate of 10 liters/min for at least 5 minutes |
| 5 | Protected against water jets | Water projected in jets against the housing from any direction shall have no harmful effects | 14.2.5, including, for example, spraying water from a 6.3 mm diameter nozzle at a distance of 2.5-3 m from the housing at a water flow rate of 12.5 liters/min for at least 3 minutes |

TABLE 3-continued

| Rating Level | Degree of Protection | | Test conditions, see IEC 60529 section |
|---|---|---|---|
| | Brief Description | Definition | |
| 6 | Protected against powerful water jets | Water projected in powerful jets against the housing from any direction shall have no harmful effects | 14.2.6, including, for example, spraying water from a 12.5 mm diameter nozzle at a distance of 2.5-3 m from the housing at a water flow rate of 100 liters/min for at least 3 minutes |
| 7 | Protected against the effects of temporary immersion in water | Ingress of water in quantities causing harmful effects shall not be possible when the housing is temporarily immersed in water under standardized conditions of pressure and time | 14.2.7, including, for example, immersion for 30 min in a water tank such that the bottom of the housing is 1 m below the surface of the water and the top of the housing is 0.15 m below the surface of the water |
| 8 | Protected against the effects of continuous immersion in water | Ingress of water in quantities causing harmful effects shall not be possible when the housing is continuously immersed in water under conditions which shall be agreed between manufacturer and user but which are more severe than for numeral 7 | 14.2.8, including, for example, immersion in a water tank such that the bottom of the housing is greater than 1 m below the surface of the water and the top of the housing is greater than 0.15 m below the surface of the water |
| 9 | Protected against high pressure and temperature water jets | Water projected at high pressure and high temperature against the housing from any direction shall not have harmful effects | 14.2.9, including, for example, spraying water on the housing from all practical directions from a fan jet nozzle at a distance of 175 +/− 25 mm from the housing and spraying water at a flow rate of 15 liters/min for at least 3 min |

For example, the housing 120 can be constructed to be water-resistant and tested for such in accordance with the IEC 60529 standard for Ingress Protection. For instance, the one or more housings 120 of the device may be configured to have a rating of level 7, protecting against immersion in water, up to one meter for thirty minutes. This enables a patient to wear the device 100 in the bathtub or shower for uninterrupted, continuous use. In implementations, the one or more housings 120 of the device 100 may be multiple coded, including two or more levels. For example, the a housing 120 of the device 100 can maintain a liquid Ingress Protection level of 7, protecting against temporary immersion, and a liquid Ingress Protection level of 5, protecting against water jets.

As described previously, the at least one housing 120 shields one or more of the therapy delivery circuit, the ECG acquisition and conditioning circuit 125, the processor 118, at least one capacitor 135, and at least one power source (e.g., battery 140) from environmental impact. The housing 120 covers and/or surrounds the hardware components therein, protecting them from wear and tear and protecting the patient from contacting high voltage components. The housing 120 protects the components from liquid ingress while the patient is showering, for example.

As described previously with regard to the contoured pad 105, the housing 120 is non-conductive, water vapor-permeable, and substantially liquid-impermeable or waterproof. The housing 120 may comprise or consist of polyurethane, such as TEGADERM polyurethane film (available from 3M), OPSITE polyurethane film (available from Smith & Nephew), or HYDROFILM polyurethane film (available from Hartman USA). In other examples, the contoured pad 105 can comprise or consist of at least one of neoprene, thermoformed plastic, or injection molded rubber or plastic, such as silicone or other biocompatible synthetic rubber. In examples, the housing 120 can include a non-woven laminate material such as at least one spandex, nylon-spandex, and nylon-LYCRA. In examples, the housing 120 can included a thermoformed layer coated with a waterproof or water repellant layer, such as a layer of a non-woven polyurethane fabric material. One or more vapor release valves or through holes can be formed into or disposed through the housing for venting perspiration out of the housing 120. In other examples, the housing 120 can comprise or consist of a fabric having a biocompatible surface treatment rendering the fabric water resistant and/or waterproof. For example, the fabric can be enhanced by dipping in a bath of fluorocarbon, such as Teflon or fluorinated-decyl polyhedral oligomeric silsesquioxane (F-POSS).

In addition to waterproof and/or water resistant characteristics, the adhesively coupled device 100 is volumetrically sized for patient comfort. In examples, the patient-worn monitoring and treatment device 100 has a weight between 250 grams and 2,500 grams. For example, the device 100 can have a weight in a range of at least one of 250 grams and 1,250 grams, 500 grams and 1,000 grams, and 750 grams and 900 grams. Maintaining the weight within such example ranges improves patient comfort. Because the device 100 adheres to the skin of the torso 5 of the patient, examples of the device 100 include weight distribution and adhesive features for encouraging patient compliance by improving comfort and sustaining attachment throughout the prescribed duration.

In implementations in which the contoured pad 105 includes a plurality of segments, the housing 120 can comprise a plurality of housings, and one or more of the therapy delivery circuit 130, the ECG acquisition and conditioning circuit 125, the processor 118, at least one capacitor 135, and at least one power source (e.g., battery 140) can be each within a separate housing disposed on a corresponding one of the plurality of segments. By apportioning the components within separate housings, the device 100 can be modular in implementations. This modularity allows for removal of one or more components for servicing or replacement. For example, a housing for the battery may be releasably sealed around a rechargeable battery so that a patient or caregiver can recharge and replace the battery 140 regularly during the prescribed duration of wear. As previously described, in examples, the contoured pad 105 can include a sealing lip formed of an elastomeric material that stretches when the housing 120, or one of the plurality of housings 120, is pulled away from the contoured pad 105, allowing the housing or one or more of the plurality of housings 120 to be pulled free of the sealing lip. Because the sealing lip is elastomeric, the deformation is not permanent and the sealing lip retracts to a resting state for again receiving the housing 120 or one or more of the plurality of housings 120 in a sealed configuration.

Whether the at least one housing is a single enclosure or a plurality of housings, the components of the device 100 can be distributed for patient comfort. In examples, such as that of FIG. 8, the contoured pad 105, the housing 120, and the electronics (e.g., EGC acquisition and conditioning circuit 125, processor 118, therapy delivery circuit 130, capacitor 135, battery 140 and PCB 145) are assembled into an assembly such that a center of mass 147 of the assembly is below a volumetric center 150 (e.g. centroid of volume) of the assembly when the first assembly 102 is mounted on the torso 5 of the patient. As described previously, in examples, the first and second assemblies 102, 107 of the device 100 are adhesively coupled to the torso 5 of the patient.

Referring to FIGS. 5A, 5B, and 6, a vertical axis 137 of the first and second assemblies 102, 107 is antiparallel to the force of gravity when the patient is standing or sitting and when the adhesively coupled assemblies are affixed to the patient per the medical instructions for application and use.

There are a number of forces exerted on an adhesive joint that may cause it to fail prematurely. These include one or more of the following forces:

1) Tensile force is pull exerted equally over the entire joint. With tensile force on an adhesive bond, the pull direction is normal to the adhesive bond;
2) Shear force on an adhesive bond is pull directed across the adhesive, parallel to the adhesive bond, forcing the substrates to slide over each other;
3) Cleavage force is pull concentrated at one edge of the adhesive joint, exerting a prying force on the bond. The other edge of the joint is theoretically under zero stress; and/or
4) Peel force is concentrated along a thin line at the edge of the bond where one substrate is flexible. The line is the exact point where an adhesive would separate if the flexible surface were peeled away from its mating surface. Once peeling has begun, the stress line remains in front of the advancing bond separation.

The leverage effect of cleavage and peel forces concentrate stress at smaller areas of the bond causing failure at lower force levels than those observed in tension and shear. By exploiting the relative component density inhomogeneities such as by placement of the components within the housing, and distributing the electronic components such that the center of mass or center of gravity 147 for the housing 120 is below the volumetric center 150 of the housing 120 in their positions along the vertical axis 137, the delamination forces, such as the cleavage and peel, can be minimized. This assists with securing the first assembly 102 to the patient while minimizing any undesired partial or full separation of the device 100 from the skin of the patient during the prescribed duration of wear. If the contoured pad 105 pulls away from the skin of the patient, the therapy electrodes 110 and ECG sensors 115 can lose contact with the skin, preventing proper monitoring of the patient.

In implementations, as shown in FIG. 6, the center of mass or center of gravity 147 for the housing 120 is below the volumetric center 150 of the housing 120 relative to the vertical axis 137 such that the ratio of the distance V1 between the center of mass or center of gravity 147 and the inferior margin line 136 of the housing 120 divided by the distance V2 between the volumetric center 150 and the inferior margin line 136 is less than 90%. As shown in the example of FIG. 6, the inferior margin line 136 is the line (or plane) tangential to a bottom end 123 of the housing 120. In other implementations, the ratio of the distances V1/V2 may be less than 80%. In other implementations, the ratio of the distances V1/V2 can be less than 75%. In other implementations, the ratio of the distances V1/V2 can be less than 70%. In other implementations, the ratio of the distances V1/V2 can be less than 50%. In other implementations, the ratio of the distances V1/V2 can be less than 30%. In other implementations, the ratio of the distances V1/V2 can be less than 20%. In implementations, the ratio of the distances V1/V2 can be in a range of between 1% to 90%. In implementations, the ratio of the distances V1/V2 can be in a range of between 5% to 80% In implementations, the ratio of the distances V1/V2 can be in a range of between 10% to 70%

Figure 8:
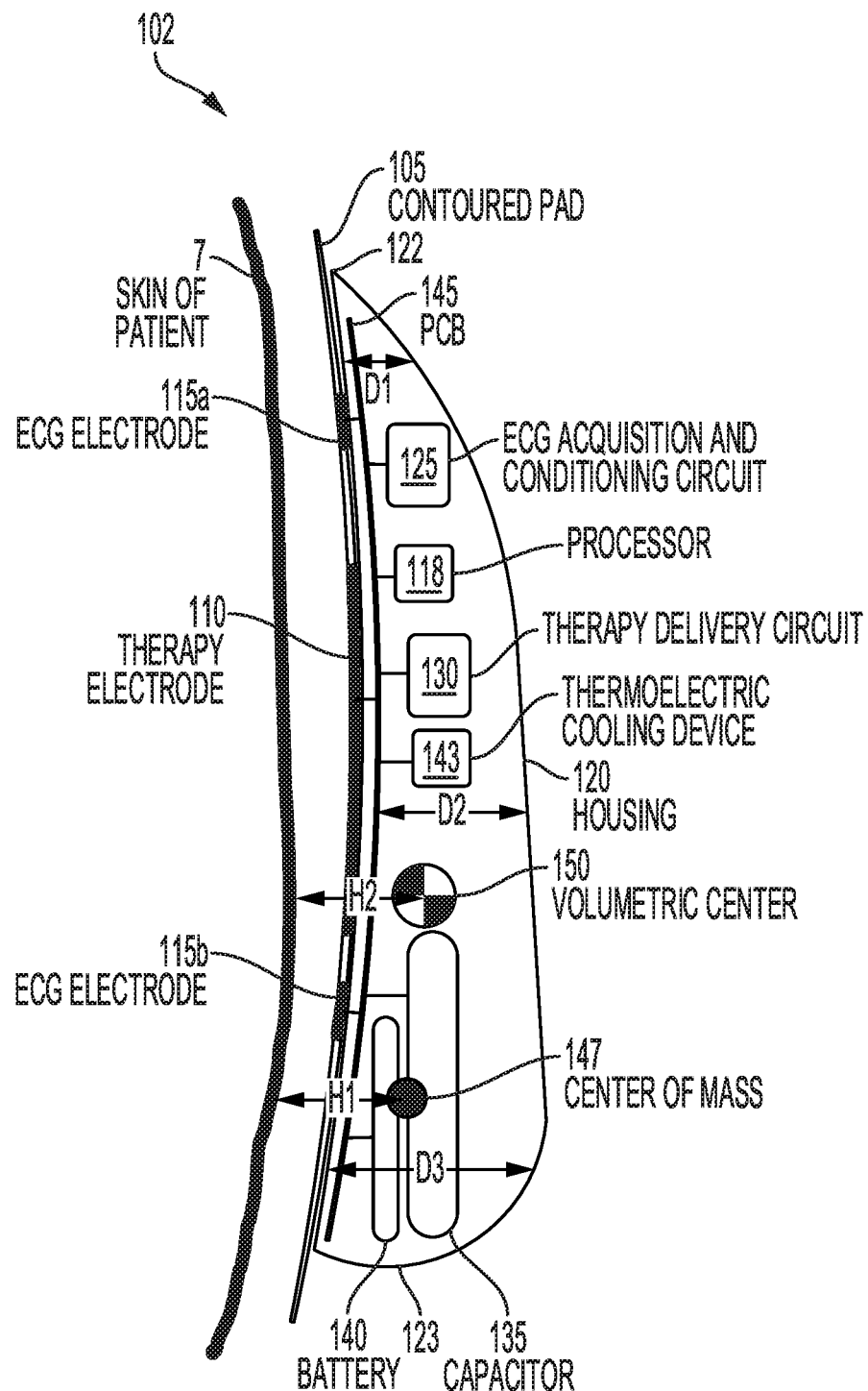
FIG. 8 depicts a side cross-section schematic of an example wearable cardiac monitoring and treatment device.

In other implementations, as that shown in FIG. 8, a second axis may be chosen to determine distance ratios, such as for instance a lateral axis H that measures proximity to the patient's skin. In these implementations, the ratio of the lateral distance H1 between the center of mass or center of gravity 147 and the patient-facing surface of the contoured pad 105 divided by the lateral distance H2 between the volumetric center 150 and the patient-facing surface of the contoured pad 105 is less than 90%. In other implementations, the ratio of the lateral distances H1/H2 may be less than 80%. In other implementations, the ratio of the lateral distances may be less than 70%. In other implementations, the ratio of the lateral distances H1/H2 may be less than 50%. In other implementations, the ratio of the lateral distances H1/H2 may be less than 30%. In other implementations, the ratio of the lateral distances H1/H2 may be less than 20%. In implementations, the ratio of the lateral distances H1/H2 can be in a range of between 1% to 90%. In implementations, the ratio of the lateral distances H1/H2 can be in a range of between 5% to 80% In implementations, the ratio of the lateral distances H1/H2 can be in a range of between 10% to 70%.

In some implementations, there may be more than one vertical axis 137 defined, e.g. a vertical axis oriented based on the patient awake and standing, and a second vertical axis based on the patient asleep on their backs. In order to meet the above criteria for the ratio of distances for both orientations, the center of gravity of center of mass 147 is located in the lower, rear quadrant of the housing 120.

In examples, the heaviest electrical components (e.g., the at least one capacitor 135 and battery 140) are disposed below the volumetric center 150 of the first assembly 102. Alternatively or additionally, the heaviest electrical components are positioned close to the contoured pad 105. For example, as shown in FIG. 8, the capacitor 135 and battery 140 both have flat geometries enabling their being layered at an end of the first assembly 102 below the volumetric center 150. The relatively more lightweight electrical components, such as integrated circuits or systems on a chip (SoCs), such as the therapy delivery circuit 130 and ECG acquisition and conditioning circuit 125, are disposed within the housing 120, above the volumetric center 150. Because the center of mass 147 of the first assembly 102 is below the volumetric center 150, the contoured pad 105 is less likely to peel away from the torso 5 of the patient under gravitational forces and other forces acting on the device as the patient moves.

Additionally or alternatively, in examples, such as that of FIG. 8, the first assembly 102 of the device 100 has an ergonomic profile. In implementations, the housing 120 extends a distance D of between around 1 cm and 5 cm from a surface of the contoured pad 105. In the example of FIG. 8, in which the center of mass 147 is below the volumetric center 150 and the heavier and/or larger components are below the volumetric center 150, the housing 120 can be shaped ergonomically to follow the general contour of the components housed therein. For example, the distance D at which the housing 120 extends from the surface of the contoured pad 105 can vary from a top end 122 to a bottom end 123 (e.g., the top end being oriented closer to a head of the patient than the bottom end). In one example, the side profile has the appearance of a right triangle with rounded surfaces and edges, or an approximately teardrop shape. In the example of FIG. 8, the distance D1 at the top end 122 of the first assembly 102 is shorter than the distance D2 at the middle, and the distance D2 at the middle is shorter than the distance D3 at the bottom end 123. The example profile of the housing 120 of FIG. 8 provides a comfortable weight distribution that reduces pulling on the skin under gravitational forces attempting to rotate the top end 122 away from the torso 5. The teardrop shaped cross-section of the first assembly, therefore, offsets the peel force tending to pull the contoured pad 105 away from the torso. Additionally, the streamlined profile shape follows the contours of a lower anterior region of the torso 5 compactly such that the device 100 is unnoticeable or protrudes very little when worn beneath a garment of clothing. Such a comfortable, compact configuration encourages patient compliance by maintaining a patient's privacy during the prescribed duration of wear.

As described previously with regard to the examples of FIGS. 3A through 4D, implementations of adhesively coupled wearable device 100 can include additional wearable supports and/or support garments for offsetting one or more forces such as peel forces, shear forces, cleavage forces, and tensile forces and retaining the wearable device 100 in contact with the torso 5 of the patient. In such implementations, the wearable supports and/or support garments assist with preventing the device 100 from pulling on the skin of the patient and therefore increase and/or ensure patient comfort throughout the duration of wear. Ensuring patient comfort removes an impediment to patient compliance with wearing the device throughout the prescribed durations. Such wearable supports and/or support garments can be especially beneficial during long-term durations of prescribed wear.

As described previously and as shown in the examples of FIGS. 10A-D, the device 100 can further comprise a breathable anisotropic conductive gel 660 disposed between the contoured pad 105 and the torso 5 and configured for placement along at least one of the plurality of therapy electrodes 110. In examples, the ratio of an area footprint (e.g., surface area bounded by the perimeter) of breathable anisotropic conductive gel 660 to an area footprint of the contoured pad 105 ranges from about 0.30-0.75. In examples, the ratio of the area footprint of the breathable adhesive 665 to an area footprint of the contoured pad 105 ranges from about 0.05-0.25.

By limiting the area footprint of the adhesive 665 to only what is necessary for supporting the weight of the device 100 for the prescribed duration, the surface area of skin contacted by adhesive is limited to only a portion of the area footprint of the contoured pad 105. This limits the potential for skin irritation by adhesives and assists with moisture evaporation from areas of the skin not contacted by the adhesive. In some implementations, such as that of FIG. 10C, the adhesive 665 is disposed on only part of the perimeter of the contoured pad 105, providing one or more outlets 670 facilitating moisture evaporation. Additionally or alternatively, in some examples, such as that of FIG. 10D, the gel 660 includes a plurality of perforations 662 for facilitating evaporation of perspiration at the device-skin interface.

Returning now to FIG. 8, as described previously, in implementations, the housing extends a distance D of between around 1 cm and 5 cm from a surface of the contoured pad. For example, the housing can extend 1 cm, 1.5 cm, 2 cm, 2.5 cm, 3 cm, 3.5 cm, 4 cm, 4.5 cm and 5 cm from the contoured pad. In addition to maintaining a center of mass 147 below the volumetric center 150, the device 100 maintains a low profile and is inconspicuously worn under a patient's clothing. The device does not protrude so far from the skin of the patient so as to cause one or more noticeable bulges beneath clothing and therefore more seamlessly integrates with a patient's lifestyle. Patients who feel less disrupted by wearing the device 100 are more likely to comply with wearing the device for the prescribed duration. In examples, the volume under the housing 120, and therefore the distance of the housing from the surface of the contoured pad, depends upon a combination of component sizes, shapes, and relatively placements.

In examples, the at least one power source of the device 100 includes one or more batteries 140 having a combined envelope volume not to exceed one quarter of the volume of the at least one housing 120 and having a capacity of no less than 1200 mAh. In examples, the at least one power source includes one or more batteries having a combined envelope volume not to exceed one quarter of the volume of the at least one housing and having a capacity of 1200 mAh to 8000 mAh. In examples, the at least one battery 140 is configured to provide power to one or more components, such as the one or more capacitors 135. In examples, the battery 140 can include a rechargeable battery or multi-cell battery pack. In examples, the battery 140 can include a non-rechargeable, replaceable battery. In one example implementation, the battery 140 can include three or more 2200 mAh lithium ion cells that provide electrical power to the other components within the device 100. In implementations, the at least one power source comprises at least one 1470 mAh, 3V Lithium ion battery. In examples, the battery 140 can include a plurality of coin cell batteries. In examples, the one or more batteries are flat packed lithium polymer batteries. In examples, the battery 140 can be a flat packed (e.g., prismatic) battery, such as, for example, a lithium ion battery having dimensions ranging between, for example, 12 mm×4 mm×1 mm and 35 mm×50 mm×2 mm. In examples, the at least one power source comprises one or more batteries 140 having a combined volume ranging from about 1 $cm^2$ to 7 $cm^2$ and weighing between about 1 g to 70 g (e.g., 1 g, 5 g, 10 g, 15 g, 20 g, 25 g, 30 g, 40 g, 50 g, 55 g, 60 g, 65 g, 70 g). In examples, the one or more batteries 140 are rechargeable and can provide power output in a range of between 20 mA to 3000 mA and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the device 100 (e.g., defibrillation, pacing, etc.).

It is appreciated that a capacitor 135 of the device 100 may be constructed in a variety of form factors. For example, the capacitor 135 may include an encapsulating rigid enclosure. In implementations, the rigid enclosure can be contoured to conform to the curvature of the torso 5 of the patient thereby resulting in a comfortable, mated fit when worn. For example, the enclosure may be constructed from a rigid plastic including, for example, acrylonitrile butadiene styrene (ABS) plastic with a contoured surface that conforms to the silhouette of a patient. For example, the contoured surface can be configured to conform with a curvature of a portion of the patient's torso, such as lower portion of the torso, an upper anterior portion of the torso, upper posterior portion of the torso, one or more lateral portions of the torso. The particular shape of the contoured surface may be pre-configured or uniquely designed for the patient. For example, various body size measurements may be obtained from the patient and a uniquely tailored enclosure may be 3D printed from, for example, any suitable thermoplastic (e.g., ABS plastic).

In some implementations, the capacitor 135 may be compact film capacitor such as a small film capacitor with a maximum thickness of between 1 mm and 40 mm, a capacitance under 700 μF, and a breakdown voltage rating between 500 and 2500 volts. In examples, the capacitor 135 has an envelope volume ranging from about 10 $cm^2$ to 15 $cm^2$. In examples, the capacitor 135 has a 140 microfarad capacity and a voltage rating of at least 1600V. The film capacitor 135 can be manufactured of tightly wound dielectric layers that are compressed and molded to match the silhouette of a patient. For example, the plurality of capacitors can be configured to conform with a curvature of a portion of the patient's torso 5, such as lower portion of the torso, an upper anterior portion of the torso, upper posterior portion of the torso, or one or more lateral portions of the torso. Shaping one or more film capacitors 135 to accommodate one or more contoured regions of a patient's torso 5 increases patient comfort and minimizes bulkiness associated with cylindrical or stacked capacitors. The device 100 therefore can protrude less from the surface of the patients skin that it would if the capacitor had a larger volume and/or less accommodating profile. Table 4 provides examples of weights of various components of implementations of the device 100:

TABLE 4

| Component | Implementation #1 Weight (g) | Implementation #2 Weight (g) |
|---|---|---|
| PCB | 150 | 200 |
| Capacitor | 118 | 400 |
| Response Button(s) | 2 | 3 |
| Contoured Pad | 25 | 150 |
| Speaker | 7 | 8 |
| Housing | 112 | 150 |
| Assembly Components/Mounts | 10 | 15 |
| Battery | 35.5 | 570 |
| Electrodes (e.g., 2 sensing, 2 therapy) | 0.1 | 10 |
| Hydrogel | 0.1 | 0.5 |
| Adhesive | 0.1 | 0.5 |

The weights of various components can be selected for comfort, size and performance characteristics. For example, as described previously, the one or more batteries 140 can be rechargeable, non-rechargeable, cylindrical, prismatic, and sized for providing energy for one or more defibrillation or pacing charges. Tables 5 and 6 provide example Lithium Ion Prismatic Batteries and Lithium Ion Cylindrical Batteries for use in one or more implementations of short term and long-term wear embodiments of the adhesively coupled device 10, 100, 800:

Lithium Ion Prismatic Battery Examples:

TABLE 5

| Mfgr | Dimensions (mm) | Weight (g) | Nominal Capacity (mAh) | Volume w/ Packing Eff 2 Cells (mL) | Weight 2 Cells (g) | Specific Energy Density 2 Cells (Ah/gL) | Volume w/ Packing Eff 3 Cells (mL) | Weight 3 Cells (g) | Specific Energy Density 3 Cells (Ah/gL) |
|---|---|---|---|---|---|---|---|---|---|
| E-One Moli | 10.8 × 33.9 × 50.2 | 46.5 | 1800 | 38.96395 | 93 | 0.496737 | 58.44593 | 139.5 | 0.220772 |
| E-One Moli | 11.5 × 34 × 50 | 41.5 | 2000 | 41.446 | 83 | 0.581392 | 62.169 | 124.5 | 0.258397 |
| E-One Moli | 11.5 × 34 × 50 | 43 | 2200 | 41.446 | 86 | 0.617222 | 62.169 | 129 | 0.274321 |
| E-One Moli | 10.8 × 34 × 50 | 42 | 2000 | 39.07889 | 84 | 0.609268 | 58.61834 | 126 | 0.270786 |
| Panasonic | 10.5 × 33.8 × 48.5 | 38.3 | 2350 | 36.49082 | 76.6 | 0.840728 | 54.73623 | 114.9 | 0.373657 |
| Panasonic | 10.5 × 33.8 × 48.8 | 38.5 | 2000 | 36.71653 | 77 | 0.70742 | 55.0748 | 115.5 | 0.314409 |

Lithium Ion Cylindrical Battery Examples

TABLE 6

| Mfgr | Dimensions (mm) | Weight (g) | Nominal Capacity (mAh) | Volume w/ Packing Eff 2 Cells (mL) | Weight 2 Cells (g) | Specific Energy Density 2 Cells (Ah/gL) | Volume w/ Packing Eff 3 Cells (mL) | Weight 3 Cells (g) | Specific Energy Density 3 Cells (Ah/gL) |
|---|---|---|---|---|---|---|---|---|---|
| E-One Moli | 18.6 × 65.2 | 46 | 3000 | 40.27 | 92 | 0.810 | 61.32 | 138 | 0.355 |
| E-One Moli | 20.8 × 70.2 | 60 | 3000 | 54.22 | 120 | 0.461 | 82.56 | 180 | 0.202 |
| E-One Moli | 18.4 × 65.2 | 48 | 2400 | 39.41 | 96 | 0.634 | 60.01 | 144 | 0.278 |
| E-One Moli | 18.6 × 65.2 | 50 | 2600 | 40.27 | 100 | 0.646 | 61.32 | 150 | 0.283 |
| E-One Moli | 18.6 × 65.2 | 50 | 2800 | 40.27 | 100 | 0.695 | 61.32 | 150 | 0.304 |
| E-One Moli | 18.4 × 65.2 | 47.5 | 2250 | 39.41 | 95 | 0.601 | 60.01 | 142.5 | 0.263 |
| E-One Moli | 18.6 × 65.2 | 47 | 2000 | 40.27 | 94 | 0.528 | 61.32 | 141 | 0.231 |
| E-One Moli | 18.6 × 65.2 | 47 | 2500 | 40.27 | 94 | 0.660 | 61.32 | 141 | 0.289 |
| Panasonic | 18.5 × 65.3 | 48.5 | 3350 | 39.90 | 97 | 0.866 | 60.75 | 145.5 | 0.379 |
| Panasonic | 18.5 × 65.3 | 48.5 | 3350 | 39.90 | 97 | 0.866 | 60.75 | 145.5 | 0.379 |
| Panasonic | 18.5 × 65.3 | 48 | 3450 | 39.90 | 96 | 0.901 | 60.75 | 144 | 0.394 |
| Panasonic | 18.5 × 65.3 | 48.5 | 2750 | 39.90 | 97 | 0.711 | 60.75 | 145.5 | 0.311 |
| Panasonic | 18.6 × 65.3 | 49 | 2150 | 40.33 | 98 | 0.544 | 61.41 | 147 | 0.238 |
| Panasonic | 18.6 × 65.3 | 49 | 2150 | 40.33 | 98 | 0.544 | 61.41 | 147 | 0.238 |
| Panasonic | 18.6 × 65.3 | 49 | 2500 | 40.33 | 98 | 0.632 | 61.41 | 147 | 0.277 |
| Panasonic | 18.6 × 65.3 | 49 | 1950 | 40.33 | 98 | 0.493 | 61.41 | 147 | 0.216 |
| Panasonic | 18.6 × 65.3 | 49 | 3000 | 40.33 | 98 | 0.759 | 61.41 | 147 | 0.332 |
| Samsung SDI | 18.4 × 65.0 | 48 | 2800 | 39.29 | 96 | 0.742 | 59.82 | 144 | 0.325 |
| Samsung SDI | 18.4 × 65.0 | 44.5 | 2200 | 39.29 | 89 | 0.629 | 59.82 | 133.5 | 0.275 |
| Samsung SDI | 18.4 × 65.0 | 47 | 2600 | 39.29 | 94 | 0.704 | 59.82 | 141 | 0.308 |
| Samsung SDI | 18.4 × 65.0 | 47 | 2600 | 39.29 | 94 | 0.704 | 59.82 | 141 | 0.308 |
| Samsung SDI | 18.40 × 65.0 | 48 | 2950 | 39.29 | 96 | 0.782 | 59.82 | 144 | 0.342 |
| Samsung SDI | 18.40 × 65.0 | 50 | 3200 | 39.29 | 100 | 0.814 | 59.82 | 150 | 0.357 |
| Samsung SDI | 18.33 × 64.85 | 45 | 2500 | 38.90 | 90 | 0.714 | 59.23 | 135 | 0.313 |

In another example, as described previously, in embodiments, the capacitor 135 can be an approximately 140 microfarad, 1600V film capacitor weighing about 118 grams. Alternatively, the capacitor 135 can be a 4 cell cylindrical electrolytic capacitor with a 140 microfarad discharge rating that weighs approximately 400 grams. Similarly, other hardware components can be sized and shaped for compact, lightweight design without impacting performance. For example, the H-Bridge can be in the of a compact, surface mounted silicon carbide FET (Sic FET) rather than a 4 part IGBT configuration. The ECG acquisition and conditioning circuitry, processor, and therapy delivery circuit can be included on one or more ASICs or one or more wire bonded, epoxy resin protected "chip on board" flip chips.

Figure 11A:
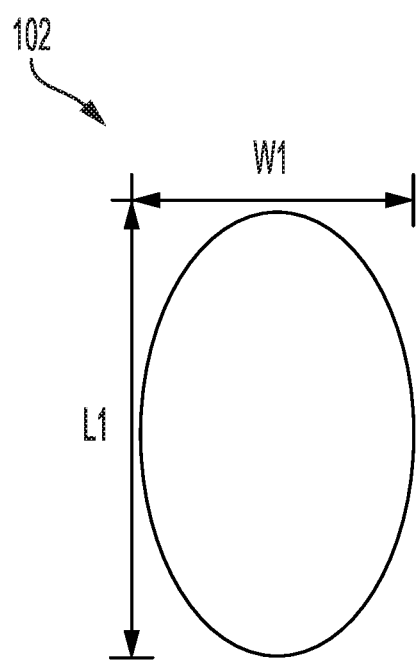
FIG. 11A depicts a plan view schematic of a first assembly of an example adhesively coupled wearable cardiac monitoring and treatment device.

Other features of the contoured pad 105 contribute to stability of the device 100 during the prescribed duration of wear. For example, the contoured pad 105 is sized to accommodate the components disposed within the housing 120 and/or integrated within the contoured pad 105 while providing sufficient adhesive surface area for securing the first assembly 102 of the device 100 to the skin of the patient for the prescribed duration. In one example, as shown in FIG. 11A, the contoured pad has a width W1 of between 2 cm and 18 cm and a length L1 of between 12 cm and 36 cm. In implementations, the contoured pad 105 circumscribes an area (e.g., an "area footprint") in a range of about 200 to 300 square centimeters. In implementations, the contoured pad 105 has an area footprint of approximately 230 square centimeters (e.g., 0.023 square meters). Components thereon and/or therein have a cumulative weight ranging from 0.25 kg to 2.25 kg. In this example, the first assembly 102 therefore has a weight to area footprint ratio of about 10 kg/m$^2$ to 100 kg/m$^2$. Table 7 provides additional examples of weight (kg) to area footprint (m$^2$) ratios for the first assembly 102. The weights shown below are examples. Other weights are possible including ranges from around 2.25 kgs to around 10 kgs depending on the selection and design of the components, as well as whether a wearable support is used.

TABLE 7

| Weight (kg) | Surface area (m$^2$) | Ratio (weight of device/area footprint) | ratio −25% | ratio +25% |
|---|---|---|---|---|
| 0.25 | 0.023 | 10.86956522 | 8.152174 | 13.58696 |
| 0.5 | 0.023 | 21.73913043 | 16.30435 | 27.17391 |
| 0.75 | 0.023 | 32.60869565 | 24.45652 | 40.76087 |
| 1 | 0.023 | 43.47826087 | 32.6087 | 54.34783 |
| 1.25 | 0.023 | 54.34782609 | 40.76087 | 67.93478 |

TABLE 7-continued

| Weight (kg) | Surface area (m$^2$) | Ratio (weight of device/area footprint) | ratio −25% | ratio +25% |
| --- | --- | --- | --- | --- |
| 1.5 | 0.023 | 65.2173913 | 48.91304 | 81.52174 |
| 2 | 0.023 | 86.95652174 | 65.21739 | 108.6957 |
| 2.25 | 0.023 | 97.82608696 | 73.36957 | 122.2826 |

As described previously with regard to the examples of FIGS. 5A and B, the device 100 includes a first assembly 102 and a separate second assembly 107 coupled to the first assembly 102 and configured to be adhesively coupled to the torso 5 of the patient. The second assembly 107 can be coupled to the first assembly 102 with one or more conductive threads or wires configured for delivering current for an electrical pulse, such as a, for example, a 360 J defibrillation pulse.

Figure 11B:
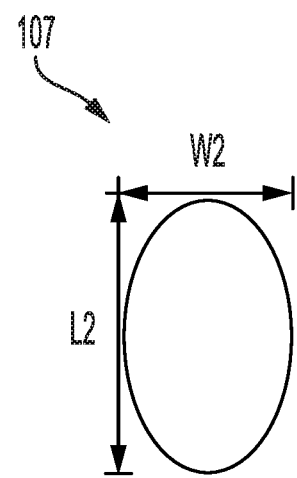
FIG. 11B depicts a plan view schematic of a second assembly of an example adhesively coupled wearable cardiac monitoring and treatment device.

The second assembly 107 can include breathable and non-irritating materials and adhesives as described above with regard to the first assembly 102 and contoured pad 105. In examples, the second assembly 107 includes a second one of the plurality of therapy electrodes 110 integrated with a pad 109 of the second assembly 107 and in wired communication with the therapy delivery circuit 130. In examples, the second assembly 107 includes an ECG sensor 115. Because the first assembly 102 contains the therapy delivery circuit, and various other electrical components, the second assembly 107 can be more compact than the first assembly. For example, the second assembly can be a low profile adhesive pad including a therapy electrode 110 and an ECG electrode 115 and having a pad thickness of about 0.1 cm to 2 cm. In one example, as shown in FIG. 11B, the contoured pad 109 of the second assembly 107 has a width W2 of between 1 cm and 4 cm and a length L2 of between 2 cm and 10 cm. In one example, the contoured pad 109 circumscribes an area (e.g., an "area footprint") of the patient's skin of approximately 100 square centimeters (e.g., 0.01 square meters). Components thereon and/or therein have a cumulative weight ranging from 0.05 kg to 1.0 kg. In this examples, the second assembly has a weight to area footprint ratio of about 5 kg/m$^2$ to 100 kg/m$^2$. Table 8 provides additional examples of weight (kg) to area footprint (m$^2$) ratios for the second assembly 107. The weights shown below are examples. Other weights are possible including ranges from around 1 kg to around 10 kgs depending on the selection and design of the components, as well as whether a wearable support is used.

TABLE 8

| Weight (kg) | Surface area (m$^2$) | Ratio (weight of device/area footprint) | ratio −25% | ratio +25% |
| --- | --- | --- | --- | --- |
| 0.05 | 0.01 | 5 | 3.75 | 6.25 |
| 0.075 | 0.01 | 7.5 | 5.625 | 9.375 |
| 0.1 | 0.01 | 10 | 7.5 | 12.5 |
| 0.25 | 0.01 | 25 | 18.75 | 31.25 |
| 0.5 | 0.01 | 50 | 37.5 | 62.5 |
| 0.75 | 0.01 | 75 | 56.25 | 93.75 |
| 1 | 0.01 | 100 | 75 | 125 |

In examples, the second assembly 107 is made of water resistant and/or waterproof materials, as described previously with regard to the first assembly 102. The one or more conductive threads or wires coupling the second assembly 107 to the first assembly 102 can be encased in a waterproof layer. In examples, the one or more conductive threads or wires can be connected to or mated with the first and second assemblies 102, 107 in a waterproof and/or watertight configuration. For example, the first and second assemblies 102, 107 can further include a waterproof and/or watertight orifice or connector for receiving the one or more conductive threads or wires.

In embodiments, the contoured pad 109 of the second assembly is designed to be durable, flexible, and breathable so as to allow perspiration to evaporate. In embodiments, the contoured pad 109 is non-irritating when contacting skin as described above with regard to skin irritation grading as set forth in Table C.1 of Annex C of American National Standard ANSI/AAMI/ISO 10993-10:2010, as previously presented. In examples, the contoured pad 109 is generally non-conductive, flexible, water vapor-permeable, and substantially liquid-impermeable or waterproof. The non-conductive flexible, water-vapor permeable contoured pad 105 may comprise or consist of polyurethane, such as TEGADERM polyurethane film (available from 3M), OPSITE polyurethane film (available from Smith & Nephew), or HYDROFILM polyurethane film (available from Hartman USA). In other examples, the contoured pad 109 can comprise or consist of at least one of neoprene, thermoformed plastic, or injection molded rubber or plastic, such as silicone or other biocompatible synthetic rubber. In examples, the contoured pad 109 is a laminated pad including a waterproof or water resistant layer applied to a relatively more rigid plastic or rubber layer configured to provide structural support for a housing and electronic components disposed therein. In examples the contoured pad 109 is perforated to aid in moisture evaporation from the skin.

In embodiments, the second assembly 107 can include a conductive adhesive layer. As described in the '976 Patent, which is hereby incorporated herein by reference in its entirety, a water-vapor permeable conductive adhesive material can be, for example, a material selected from the group consisting of poly(3,4-ethylene dioxitiophene), doped with poly(styrene sulfonate), (PEDOT:PSS) poly(aniline) (PANT), poly(thiopene)s, and poly(9,9-dioctylfluorene co-bithiophen) (F8T2), and combinations thereof. Such polymers can be printed as a flexible, water vapor-permeable, conductive adhesive layer using such methods as inkjet printing, screen printing, offset printing, flexo printing, and gravure printing. In an example, a thickness of the flexible, water vapor-permeable, conductive adhesive material can be between 0.25 and 50 mils. In another example, the water vapor-permeable, conductive adhesive material can comprise conductive particles. In implementations, the conductive particles may be microscopic or nano-scale particles or fibers of materials, including but not limited to, one or more of carbon black, silver, nickel, graphene, graphite, carbon nanotubes, and/or other conductive biocompatible metals such as aluminum, copper, gold, and/or platinum.

In examples, as shown in FIGS. 3A and 5A-B, the second assembly 107 includes at least one of a plurality of therapy electrodes 110 integrated with the contoured pad 109. Example therapy electrodes 110 include, for example, conductive metal electrodes, such as those made of stainless steel, tin or aluminum, a conductive ink, or a conductive polymer. In examples, the second assembly can also include at least one of a plurality of ECG sensors 115 integrated with the contoured pad 109. As described with regard to the first assembly 102, the ECG sensors 115 of the second assembly 107 can be non-polarizable ECG electrodes (e.g., clinical grade Ag/AgCl electrodes) or polarizable electrodes (e.g., electrodes having a metal substrate with an oxide layer, such as a $Ta_2O_5$ coating) configured to measure changes in a patient's electrophysiology to measure the patient's ECG information. Example ECG sensors 115 include tantalum pentoxide electrodes, as described in, for example, U.S. Pat. No. 6,253,099 entitled "Cardiac Monitoring Electrode Apparatus and Method," the content of which is incorporated herein by reference. In implementations, the ECG sensors 115 may be made of a core plastic or metal substrate element that is coated with a thick-film polymeric compound filled with a conductive Ag/Ag/Cl metallic filler.

In some examples, at least one therapy electrode 110 and one or more ECG sensors 115 are formed within the contoured pad 109 such that a skin contact surface of each component is coplanar with or protrudes from the patient contact face of the contoured pad 105. In examples, the therapy electrode 110 and the ECG sensors 115 are disposed on the patient contact face of the contoured pad 105. In some implementations, the therapy electrode 114 and ECG sensors 115 are metallic plates (e.g. stainless steel) or substrates that are formed as permanent portions of the second assembly 107. A metallic plate or substrate can be adhered to the contoured pad 109, for example, by a polyurethane adhesive or a polymer dispersion adhesive such as a polyvinyl acetate (PVAc) based adhesive, or other such adhesive. In examples, the ECG sensors 115 are flexible, dry surface electrodes such as, for example, conductive polymer-coated nano-particle loaded polysiloxane electrodes mounted to the contoured pad 109. In some examples, the ECG sensors 115 are flexible, dry surface electrodes such as, for example silver coated conductive polymer foam soft electrodes mounted to the contoured pad 109. In examples, the ECG sensors 115 are screen printed onto the contoured pad 109 with a metallic ink, such as a silver-based ink. In implementations, each of the therapy electrodes 110 has a conductive surface adapted for placement adjacent the patient's skin. In some implementations, the therapy electrodes 110 can include an impedance reducing material and/or mechanism as subsequently described.

In implementations, the at least one therapy electrode 110 and at least one ECG sensor 115 are manufactured as integral components of the contoured pad 109. For example, the therapy electrode 110 and/or the ECG sensor 115 can be formed of the warp and weft of a fabric forming at least a layer of the contoured pad 109. In implementations, at least one of the therapy electrode 110 and the ECG sensors 115 is formed from conductive fibers that are interwoven with non-conductive fibers of the fabric.

In examples, the device 100 can include a third assembly configured to be adhesively coupled to the torso of a patient. The third pad can include one of the plurality of therapy electrodes 110 integrated with a pad of the third assembly and in wired communication with the therapy delivery circuit 130. The third assembly can have similar characteristics as those described above with regard to the second assembly 107. In examples, the third pad can be configured for adhesively attaching to a posterior portion of the torso 5 of the patient, between the shoulder blades of the patient, for example, while the first assembly 102 is positioned along the lower ridge of the rib cage and the second assembly 107 is positioned on an upper anterior portion of the torso 5 adjacent to the apex of the heart. In examples, the third assembly includes a third pad configured to be adhesively coupled to the torso of the patient adjacent the atria.

Referring now to FIGS. 4A-D, 12A-B, 13A-C, and 14, wearable supported medical devices 800, 1000 are external, ambulatory, and wearable by a patient, and configured to implement one or more configurations described herein. In implementations, the wearable supported medical device 800, 1000 is an ambulatory medical device, which, for example, is capable of and designed for moving with the patient as the patient goes about his or her daily routine.

Figure 12A:
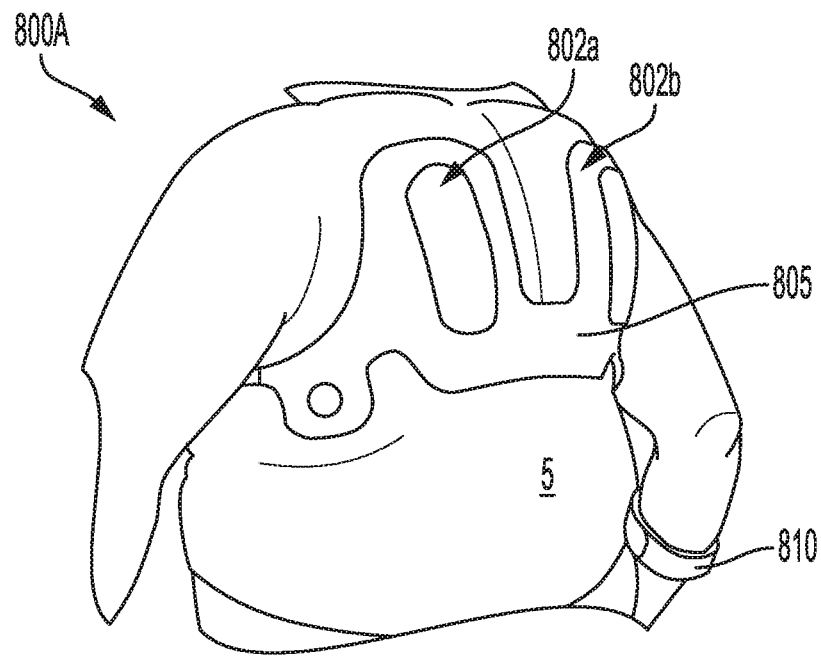
FIG. 12A depicts a rear perspective view of an example of an adhesively coupled wearable cardiac monitoring and treatment device including a wearable support.
Figure 12B:
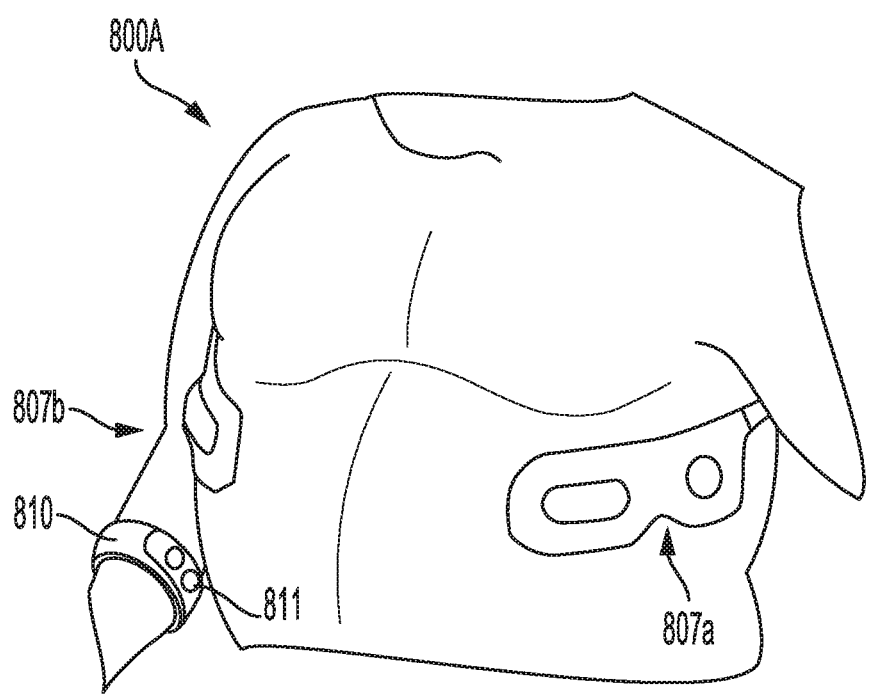
FIG. 12B depicts a front perspective view of the example adhesively coupled wearable cardiac monitoring and treatment device of FIG. 12A.

For example, as shown in FIGS. 12A and 12B, the device 800 can include one or more anterior adhesively coupled pads 807a, 807b configured for adhesion in the anterior region of the torso 5 of the patient and one or more posterior adhesively coupled pads 802a, 802b in electrical connection with the one or more anterior adhesively coupled pads 807a, 807b and configured for adhesion in the posterior region of the torso 5. In examples, such as those in FIGS. 13A-C, the posterior adhesively coupled pad 802 can be adhered to the torso 5 of the patient so that part or all of the posterior adhesively coupled pad 802 covers a side of the torso 5. This configuration provides the patient with access to the pad 802 for removal or adjustment and other device interactions. This configuration also enables concealment of the device between an arm of the patient and the torso 5. Similarly, the device 1000 of FIG. 14 is configured for concealment by connecting the posterior adhesively coupled pads 1002a, 1002b with anterior pads via a connecting portion 1005 positioned under the arm of the patient. The connection portion 1005 can be adhesively coupled to the torso 5 of the patient to assist with supporting the monitoring and treatment components of the device 1000.

Figures 13A, 13B:
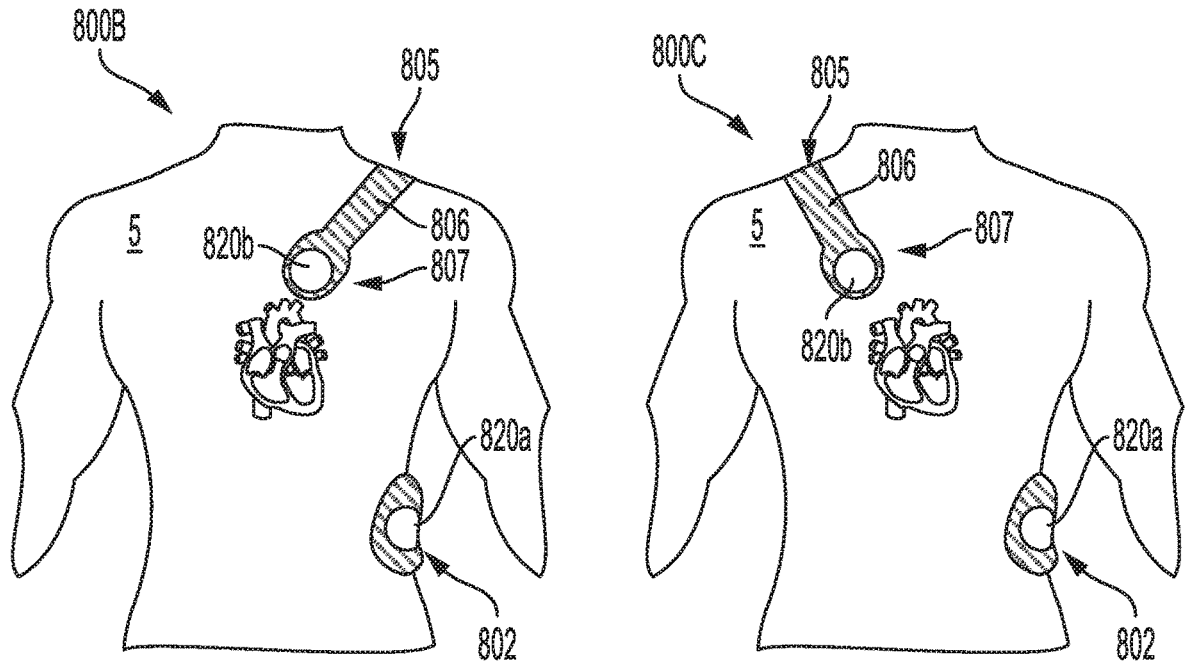
FIG. 13A depicts an example of an adhesively coupled wearable cardiac monitoring and treatment devices including a shoulder worn support that terminates at first and second adhesively coupled pads.
FIG. 13B depicts an example of an adhesively coupled wearable cardiac monitoring and treatment devices including a shoulder worn support that terminates at first and second adhesively coupled pads.
Figure 13C:
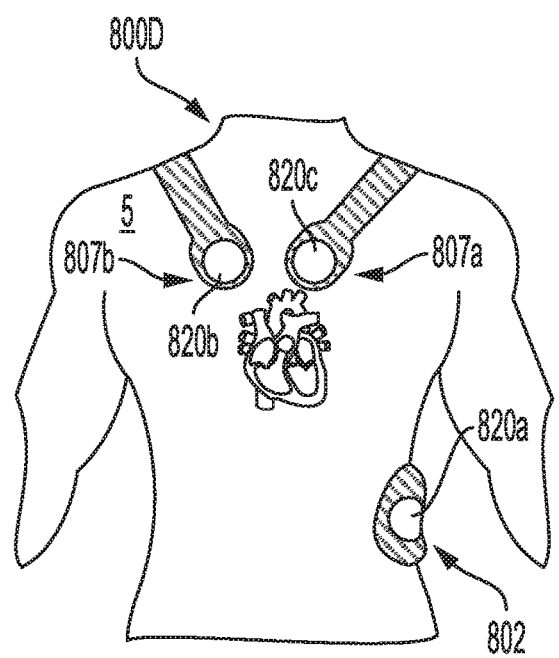
FIG. 13C depicts an example of an adhesively coupled wearable cardiac monitoring and treatment devices that includes three adhesive pads and a wearable support.
Figure 14:
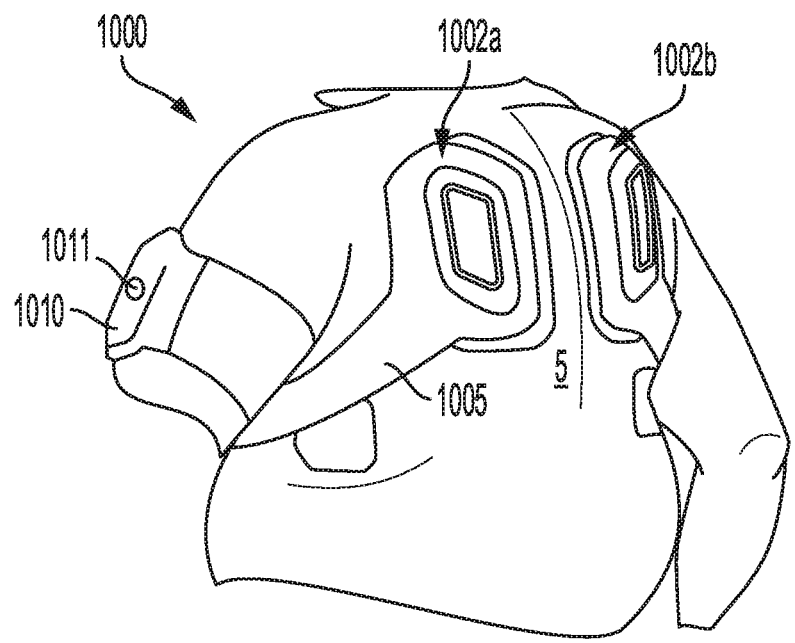
FIG. 14 depicts an example system including a user interface and an adhesively coupled wearable cardiac monitoring and treatment device.

In implementations, such as that of FIGS. 13A and 13B, a garment 805 integrated with the anterior and posterior adhesively coupled pads at least in part traces a path from the anterior adhesively coupled pad 807 coupled to an upper anterior region of the torso 5, over the shoulder of the patient, and terminates at a posterior region of the torso 5 at the posterior adhesively coupled pad 802. In examples, the garment 805 is a wearable support including a shoulder harness 806 configured to bear at least a portion of the weight of at least one of the anterior adhesively coupled pad 807 and the posterior adhesively coupled pad 802. In examples, the anterior adhesively coupled pad 807 and the posterior adhesively coupled pad 802 each weigh between 0.5 kg and 1 kg, and the shoulder harness 806 is configured to support at least a portion of the weight of both adhesively coupled pads 807, 802.

As described above with regard to FIGS. 6, 8, and 9A, for example, wearable supported device 800 includes a plurality of therapy electrodes and/or a plurality of ECG sensing electrodes integrated with the anterior adhesively coupled pad 807 and the posterior adhesively coupled pad 802. Housings 820a-c form watertight seals with each of the anterior and posterior adhesively coupled pads 807a-b, 802. For example, as shown in FIGS. 13A-B, a first housing 820b is configured to form a watertight seal with an anterior adhesively coupled pad 806 and a second housing is configured to form a watertight seal with the posterior adhesively coupled pad 802. The embodiments of FIGS. 12A-13C are water resistant and/or water repellent as described with regard to the embodiments of the device 100 of FIGS. 5-8. At least one of the housings can conceal at least an ECG acquisition and conditioning circuit, a therapy delivery circuit, and a processor. For example, the processor can analyze the ECG signal of the patient and detect one or more treatable arrhythmias, and cause the therapy delivery circuit to deliver at least one defibrillation pulse to the patient on detecting the one or more treatable arrhythmias. In implementations, the ECG sensing electrodes, ECG acquisition and conditioning circuit, therapy electrodes, therapy delivery circuit, and processor function as described above with regard to the embodiments of FIGS. 6-8.

In implementations, the processor is configured to cause the therapy delivery circuit to deliver up to five therapeutic pulses to the patient on detecting the one or more treatable arrhythmias. At least one power source is disposed within the first or second housing and coupled to the therapy delivery circuit and the pair of therapy electrodes for providing energy for the up to five therapeutic pulses.

In implementations, the capacitor 135 may be one or more capacitors disposed on one or both of the anterior adhesively coupled pad 807 and the posterior adhesively coupled pad 802. In some examples, one of the anterior adhesively coupled pad 807 and the posterior adhesively coupled pad 802 contains all of circuitry and power components. The other of the anterior adhesively coupled pad 807 and the posterior adhesively coupled pad 802 includes at least one therapy electrode and at least one ECG sensor in electrical communication with the circuitry and power components. In implementations, the wearable support 805 includes conductive thread in communication with the anterior adhesively coupled pad 807 and the posterior adhesively coupled pad 802. In implementations, the conductive thread can be integrated into the fabric of the wearable support 805. In examples, the conductive thread can be integrated in a zig zag or other doubled back pattern so as to straighten as the garment stretches. The zig zag or doubled-back pattern therefore accommodates for garment stretching and patient movement while keeping the conductive thread from contacting the skin of the patient. Integrating the conductive thread into the garment reduces and/or eliminates snagging the wire or thread on an external object. In other examples, the conductive thread can be routed on an exterior surface of the wearable support 805 so as to avoid contacting the skin of the patient and therefore avoid irritation associated with such potential contact. In implementations, the conductive thread can be routed on an exterior surface of the garment and held in place with loops, closable fabric retention tabs, or eyelets.

In embodiments, the device 800B-D further includes a breathable adhesive disposed between at least a portion of the wearable support 805 and the shoulder of the patient. The garment 805 can be at least one of a vest, a shirt, a sash, a strap, and a shoulder harness. For example, in embodiments, the garment 805 is a wearable support including a shoulder harness 806 made of a non-adhesive stretchable fabric, and an adhesive is applied along the length of the harness at least at the peripheral edges. In implementations, the fabric is a biocompatible, non-irritating, latex free fabric such as a spandex fabric, a nylon-spandex fabric, or a nylon-LYCRA fabric. The adhesive can be applied to, for example, 20-25%, 25-30%, 30-35%, 40-45%, 45%-50%, 50-60%, 60-65%, 65-70%, 70-75%, 75%-80%, 85%-90%, 95%-100% of the surface area of the garment 805. In some examples, the adhesive is applied only to the anterior adhesively coupled pad 807 and the posterior adhesively coupled pad 802, and the shoulder harness 806 stretches and remains in place on the torso 5 of the patient via compression forces. In examples, such as that of FIGS. 12A-B, the garment 805 is an entirely adhesive wearable support held in place against the torso 5 of the patient by adhesive force.

As previously described, in examples, one of the anterior adhesively coupled pad 807 and the posterior adhesively coupled pad 802 includes a therapy delivery circuit, an ECG acquisition and conditioning circuit, a processor and a PCB. The one of the anterior adhesively coupled pad 807 and the posterior adhesively coupled pad 802 including the relatively heavier collection of electronic components can be placed lower on the torso 5 than the other. The garment 805 is a wearable support configured to assist in comfortably supporting the weight of both the anterior adhesively coupled pad 807 and the posterior adhesively coupled pad 802. In examples, such as that of FIGS. 13A-B, the garment 805 is a wearable support 805 including a shoulder harness 806 tracing a path between the anterior adhesively coupled pad 807 and the posterior adhesively coupled pad 802 and over a shoulder of the patient. In implementations, the shoulder harness 806 has a tensile strength greater than at least 10% of the load exerted by the assembly 807 with no adhesive coupling and not exceeding 10 times the load exerted by the assembly 807 with no adhesive coupling. In some examples, the shoulder harness 806 has a percent elongation of between about 10% and 200%. The shoulder harness 806 therefore assists with retaining and supporting the weight of the device 800 on the torso 5 of the patient, which can be especially beneficial during long-term durations of wear. In other implementations, elasticity parameters, e.g. percent elongation, tensile strength or modulus of elasticity can be anisotropic in at least a portion of the shoulder harness 802. For instance, to better conform to the compound curvatures of the shoulder and neck region, the elasticity can be lower along the long-axis of the shoulder harness 806, compared to the short axis of the shoulder harness 806. The anisotropy allows for more stretch along the shoulder and neck area for more comfort while at the same time bearing the load of the supported housings 120.

In addition to counteracting and balancing the weight of the anterior adhesively coupled pad 807 and the posterior adhesively coupled pad 802, the garment 805 can have a curvature accommodating contours of the body of the patient. In examples, the garment 508 is a wearable support including a shoulder harness 806 that is at least one of molded, 3D printed, and knitted to a shape matching contours of the body of the patient. The device 800 therefore can be customized to fit the individual physique of the patient, thereby insuring comfort and encouraging patient compliance with wear instructions.

In some examples, the garment 805 is a wearable support including a shoulder harness 806, and at least one of the anterior adhesively coupled pad 807 and posterior adhesively coupled pad 802 are formed monolithically with the shoulder harness 806 of the wearable support garment 805. For example, the garment 805 is a wearable support that can be at least one of molded, 3D printed, die cut, and knitted to a shape matching contours of receiving portions of the torso 5 of the patient. At least one of the anterior adhesively coupled pad 807 and the posterior adhesively coupled pad 802 can be formed as part of the wearable support 805. In implementations in which the garment 805 includes a shoulder harness 806, for example, the wearable support 805 can be a die cut from a single swatch of fabric or formed substrate and can include, as terminal portions of the shoulder harness 806, the anterior adhesively coupled pad 807 and the posterior adhesively coupled pad 802. In other examples, the wearable support 805 is mated with a separately formed anterior adhesively coupled pad 807 and a separately formed posterior adhesively coupled pad 802.

In examples, each of the anterior adhesively coupled pad 807 and the posterior adhesively coupled pad 802 can include a loop or buckle configured for receiving the ends of a weight bearing strap or shoulder harness 806, for example. In such examples, the shoulder harness 806 is adjustable in length to achieve a preferential patient comfort setting. Moreover, in such examples, the shoulder harness 806 is removable for laundering without having to remove the anterior adhesively coupled pad 807 and the posterior adhesively coupled pad 802, and the removal thereby does not interfere with critical functionality of the device 800. In such examples, the anterior adhesively coupled pad 807 and the posterior adhesively coupled pad 802 can be interconnected by a wire releasably attached the shoulder harness so that the two pads continue to communicate when the shoulder harness is temporarily removed.

In other examples, each of the anterior adhesively coupled pad 807 and the posterior adhesively coupled pad 802 can include a connector for electrically connecting in a watertight configuration with a mating portion on either end of the replaceable harness. The replaceable harness can include a conductive wire or thread running therethrough or thereon and terminating at connectors at either end of the shoulder harness. In such examples, the shoulder harness can be removed, laundered, and replaced and/or discarded. Enabling a patient to launder, discard, and/or replace the shoulder harness without having to remove the anterior adhesively coupled pad 807 and the posterior adhesively coupled pad 802 assists with maintaining a clean and comfortable wearable support garment 805 throughout the prescribed duration of wear.

In examples, the garment 805 is a wearable support having a greater tensile strength and lower stiffness coefficient than either of the anterior adhesively couple pad 807 and the posterior adhesively coupled pad 802. This assists with the garment 805 being supple enough to conform to the contours of the torso 5 of the patient while also being strong enough to retain the weight of the an anterior adhesively couple pad 807 and the posterior adhesively coupled pad 802 without tearing. In examples, the garment 805 includes a shoulder harness 806 supporting at least 1.0 lbf ft of rotational torque at least at one end. In implementations, the garment 805 is a wearable support (e.g., a shoulder harness 806) that stretches no more than 1 inch with the application of 22 lbf of force. In implementations, the wearable support 805 stretches no more than 2 inches with the application of 30 lbf of force. In implementations, the wearable support 805 stretches between 0.5-3.0 inches with the application of 30 lbf of force.

In some implementations, the garment 805 is a wearable support further including at least one length adjuster configured to tension the shoulder harness 806 to a desired comfort level of the patient wearing the device 800. The length adjuster can include, for example, at least one of a drawstring, a cinch strap, a lockable bungee pull, a pull cord and spring-loaded toggle stop, a ratchet strap, an adjustable buckle, an extendable and moveable hook and loop fastener strip, a tie, a snap, and a button. By enabling a patient to adjust the length of the garment 805, the device 800 provides a mechanism for increasing or reducing tension and therefore compression forces acting on the torso 5 of the patient. The patient may prefer more or less tension while sitting, lying down, reclining, standing, walking and/or exercising, for example. In examples, the anterior adhesively coupled pad 807 and the posterior adhesively coupled pad 802 can be positioned by a caregiver or physician on the torso 5 of the patient at the start of a prescribed duration of wear, and the patient can adjust the garment 805 extending between the first and second assemblies 102, 107 throughout the duration of wear to accommodate movement, positioning, fabric stretch, and/or weight gain or loss. By limiting the garment 805 to a single supportive shoulder harness 806, for example, the device 800 covers only a portion of the torso 5, leaving the remainder of the torso uncovered by the device 800. This can assist with maintaining patient comfort during the duration of wear by minimizing the skin surface area covered on the torso 5, and therefore assisting with allowing for natural biological processes such as moisture evaporation and skin sloughing.

In examples, as with the embodiments of the device 100 shown in FIGS. 10A-10D, wearable supported device 800A-D of FIGS. 12A-13C can include a breathable anisotropic conductive gel disposed between at least one therapy electrode of the posterior adhesively coupled pad 802 and the torso 5. As with the contoured pad 105 of device 100, in some examples, the ratio of the area footprint of breathable anisotropic gel to an area footprint of the posterior adhesively coupled pad 802 ranges from about 0.30-0.75. Also as with the contoured pad 105 of device 100, the ratio of the area footprint of adhesive to an area footprint of the posterior adhesively coupled pad 802 ranges from about 0.05-0.25. In implementations, each of the anterior adhesively coupled pad 807 and the posterior adhesively coupled pad 802 includes a therapy electrode for providing a therapeutic pulse to the torso 5 of the patient. In implementations, each of the anterior adhesively coupled pad 807 and the posterior adhesively coupled pad 802 includes a breathable anisotropic conductive gel disposed between the at least one therapy electrode of each pad 802, 807 and the torso 5.

As introduced previously, in implementations, the device 100, 800 can include an impedance reducing material and/or mechanism that reduces the impedance between a therapy electrode and the patient's skin 7. In examples, the device includes a conductive hydrogel layer disposed between the therapy electrodes 110 and the skin of the patient. In implementations, the impedance reducing layer includes an anisotropic conductive gel, such as a conductive hydrogel.

In examples, the conductive gel can be a conductive adhesive layer. The conductive adhesive layer can be a water-vapor permeable conductive adhesive material. The flexible, water vapor-permeable, conductive adhesive material can comprise a material selected from the group consisting of an electro-spun polyurethane adhesive, a polymerized microemulsion pressure sensitive adhesive, an organic conductive polymer, an organic semi-conductive conductive polymer, an organic conductive compound and a semi-conductive conductive compound, and combinations thereof. In an example, a thickness of the flexible, water vapor-permeable, conductive adhesive material can be between 0.25 and 100 mils. In another example, the water vapor-permeable, conductive adhesive material can comprise conductive particles. In implementations, the conductive particles may be microscopic or nano-scale particles or fibers of materials, including but not limited to, one or more of carbon black, silver, nickel, graphene, graphite, carbon nanotubes, and/or other conductive biocompatible metals such as aluminum, copper, gold, and/or platinum.

In implementations, the device 100, 800 may include gel deployment circuitry configured to cause the delivery of conductive gel substantially proximate to a treatment site (e.g., a surface of the patient's skin in contact with the therapy electrode 114) prior to delivering therapeutic shocks to the treatment site. As described in U.S. Pat. No. 9,008, 801, titled "WEARABLE THERAPEUTIC DEVICE," issued on Apr. 14, 2015 (hereinafter the "'801 Patent"), which is hereby incorporated herein by reference in its entirety, the gel deployment circuitry may be configured to cause the delivery of conductive gel immediately before delivery of the therapeutic shocks to the treatment site, or within a short time interval, for example, within about 1 second, 5 seconds, 10 seconds, 30 seconds, or one minute before delivery of the therapeutic shocks to the treatment site. Such gel deployment circuitry may be coupled to or integrated within a therapy electrode 110 or other therapy delivery device as a single unit. When a treatable cardiac condition is detected and no patient response is received after device prompting, the gel deployment circuitry can be signaled to deploy the conductive gel. In some examples, the gel deployment circuitry may be constructed as one or more separate and independent gel deployment modules. Such modules may be configured to receive removable and/or replaceable gel cartridges (e.g., cartridges that contain one or more conductive gel reservoirs). As such, the gel deployment circuitry may be permanently disposed in the device as part of a therapy delivery circuit 130, while the cartridges may be removable and/or replaceable. Such gel deployment circuitry can be coupled to or integrated within a first assembly 102, 802, a second assembly 107, 807 and/or a third assembly of the device.

When a treatable cardiac condition is detected and no patient response is received after device prompting, the gel deployment circuitry can be signaled to deploy the conductive gel. In some examples, the gel deployment circuitry can be constructed as one or more separate and independent gel deployment modules. Such modules can be configured to receive removable and/or replaceable gel cartridges (e.g., cartridges that contain one or more conductive gel reservoirs). As such, the gel deployment circuitry can be permanently disposed in the device as part of the therapy delivery systems, while the cartridges can be removable and/or replaceable.

In some implementations, the gel deployment modules can be implemented as gel deployment packs and include at least a portion of the gel deployment circuitry along with one or more gel reservoirs within the gel deployment pack. In such implementations, the gel deployment pack, including the one or more gel reservoirs and associated gel deployment circuitry can be removable and/or replaceable. In some examples, the gel deployment pack, including the one or more gel reservoirs and associated gel deployment circuitry, and the therapy electrode can be integrated into a therapy electrode assembly that can be removed and replaced as a single unit either after use, or if damaged or broken.

In addition to including impedance reducing materials and/or mechanisms, short term and long-term wear implementations of the device 100, 800 include materials and/or mechanisms facilitating moisture vapor transmission from the skin of the patient through the device 10, 100, 800 adhered thereto.

Implementations of the device 100, 800 in accordance with the present disclosure may exhibit a moisture vapor transmission rate (MVTR) of, for example, between about 600 g/m2/day and about 1,400 g/m2/day when worn by a subject in an environment at room temperature (e.g., about 25° C.) and at a relative humidity of, for example, about 70%. Vapor permeability of the device 100, 800 is greater than 100 gram/m2/24 hours, as measured by such vapor transmission standards of ASTM E-96-80 (Version E96/E96M-13), using either the "in contact with water vapor" ("dry") or "in contact with liquid" ("wet") methods. Such test methods are described in the '976 patent, the disclosure of which is incorporated by reference herein in its entirety.

In implementations, the wearable support device 800 has a water vapor permeability of 100 g/m$^2$/24 hours. In implementations, the device 800 includes a shoulder harness 806 having a higher MVTR than either or both of the anterior adhesively coupled pad 807 and the posterior adhesively coupled pad 802. In implementations, the shoulder harness 806 has an MVTR in a range of at least about 1200-2500 g/m$^2$/24 hours and the anterior adhesively coupled pad 807 and the posterior adhesively coupled pad 802 have MVTRs in a range of about 50-1000 g/m$^2$/24 hour. In implementations of the device 100, 800, 50-75% of an area footprint of the anterior adhesively coupled pad 807 has an MVTR in a range of about 500-1200 g/m$^2$/day and 25-50% of an area footprint of the anterior adhesively coupled pad 807 has an MVTR in a range of about 250-500 g/m$^2$/day. In implementations 50-75% of an area footprint of the posterior adhesively coupled pad 802 has an MVTR in a range of about 500-1200 g/m$^2$/day and 25-50% of an area footprint of the posterior adhesively coupled pad 802 has an MVTR in a range of about 250-500 g/m$^2$/day. In implementations, the portion of the area footprint of either the anterior adhesively coupled pad 807 or the posterior adhesively coupled pad 802 having a lower MVTR is the portion having one or more breathable adhesives and/or breathable conductive hydrogels applied thereto.

In addition to having one or more breathable adhesives and/or breathable conductive hydrogels disposed between the contoured pad and the skin of the patient, implementations of the device 100, 800 include one or more moisture and heat management systems. In implementations, as previously described, the device 100, 800 includes one or more vapor permeable housings. As described previously, the housing 120, 820 is non-conductive, water vapor-permeable, and substantially liquid-impermeable or waterproof. The housing 120, 820 may comprise or consist of polyurethane, such as TEGADERM polyurethane film (available from 3M), OPSITE polyurethane film (available from Smith & Nephew), or HYDROFILM polyurethane film (available from Hartman USA). In examples, the housing 120, 820 can include a non-woven laminate material such as at least one spandex, nylon-spandex, and nylon-LYCRA. In examples, the housing 120 can included a thermoformed layer coated with a waterproof or water repellant layer, such as a layer of a non-woven polyurethane fabric material. In other examples, the housing 120 can comprise or consist of a fabric having a biocompatible surface treatment rendering the fabric water resistant and/or waterproof. For example, the fabric can be enhanced by dipping in a bath of fluorocarbon, such as Teflon or fluorinated-decyl polyhedral oligomeric silsesquioxane (F-POSS).

One or more vapor release valves or through holes can be formed into or disposed through the contoured pad 105, and/or therapy electrode 110, and/or housing for venting moisture due to perspiration as well as moisture evaporation from the patient's skin out of the housing 120, 820. As described previously, in implementations, one or more vapor release valves (e.g., vapor release valves 149*a-c* of the implementations of FIGS. 6 and 9A) can be formed into or disposed through the housing 120 for venting perspiration out of the housing 120, 820. As moisture vapor from the skin emanates through the breathable adhesive and vapor permeable contoured pad 105, vapor pressure inside the housing 120 can increase. In some implementations, the vapor release valves are pressure activated such that when moisture vapor increases within the housing 120, 820 and pressure within the housing increases to a threshold or trigger value, the one or more vapor release valves 149*a-c* open so that moisture evaporates. When moisture evaporates sufficiently to reduce the pressure within the housing below a threshold value, the vapor release valve closes. In implementations, the vapor release valve can be in communication with a processor of the device (e.g, processor 118 of FIG. 6) and electromechanically controlled.

In examples, the contoured pad 105, therapy electrode 110, and/or housing 120 can include perforations through which water vapor escapes. For example, the housing 120, 820 can include a non-woven laminate material with a plurality of microscopic punctures stippled throughout. The punctures form through holes small enough for moisture evaporation from the inside the housing to escape but too small to facilitate water ingress. For example, such through holes can range in diameter from 0.02 micrometers to 250 micrometers (e.g., approximately 0.001 mils to 10 mil). In implementations, the device 100, 800 can include moisture absorbing, vapor permeable, and/or wicking materials in the contoured pads 105, 109, 802, 809 to assist with moving moisture vapor from the skin of the patient through the housing 120, 820 for expulsion through evaporation.

In implementations, the device 10, 100, 800 can include one or more passive and/or one or more active heat management systems. For example, in implementations, the device can include one or more active heat management systems disposed within the at least one housing. In implementations, the active heat management system can include a thermoelectric cooling device (e.g. thermoelectric cooling device 143, 943 of FIGS. 8 and 9B) in communication with the processor 118. In implementations, the active heat management system can include a low-profile fan (e.g. fan 144 of FIG. 9A and fan 944 of 9B). Such a low profile fan can improve air circulation within the housing 120, 820, 920 of the device and assist with surface cooling at the device-skin interface. In implementations, the fan 144 assists with drawing moisture vapor from the skin, through the breathable adhesive and vapor permeable contoured pad 105 and through the vapor-permeable housing 120. In implementations, the fan 144 can be used in conjunction with one or more vapor transport features, such as the one or more vapor release valves 149*a-c* (collectively referred to as vapor release valves 149) described below with regard to implementations for releasing vapor emanating from the skin into the housing 120, 820. In some implementations, the device includes one or more vapor release valves without an accompanying fan 144.

Figure 9B:
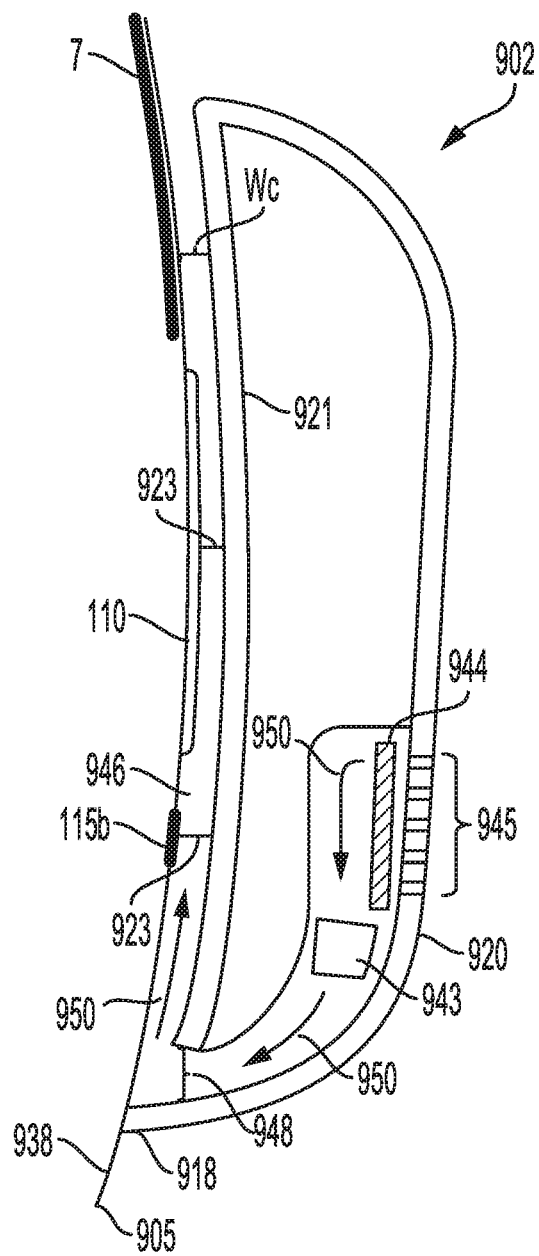
FIG. 9B depicts a side cross-section schematic of an example adhesive pad assembly of an example wearable cardiac monitoring and treatment device including an airflow channel.
Figure 10A:
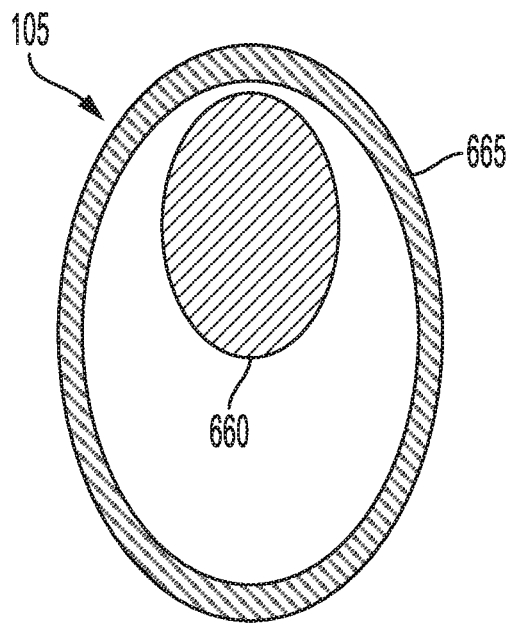
FIG. 10A depicts an example schematic of a skin-interface surface of an example wearable cardiac monitoring and treatment device including a continuous adhesive ring and an off-center conductive gel patch.
Figure 10B:
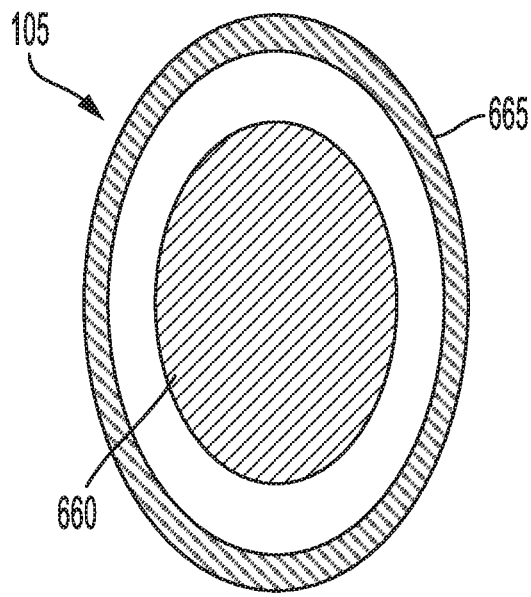
FIG. 10B depicts an example schematic of a skin-interface surface of an example wearable cardiac monitoring and treatment device including a continuous adhesive ring and an off-center conductive gel patch.
Figure 10C:
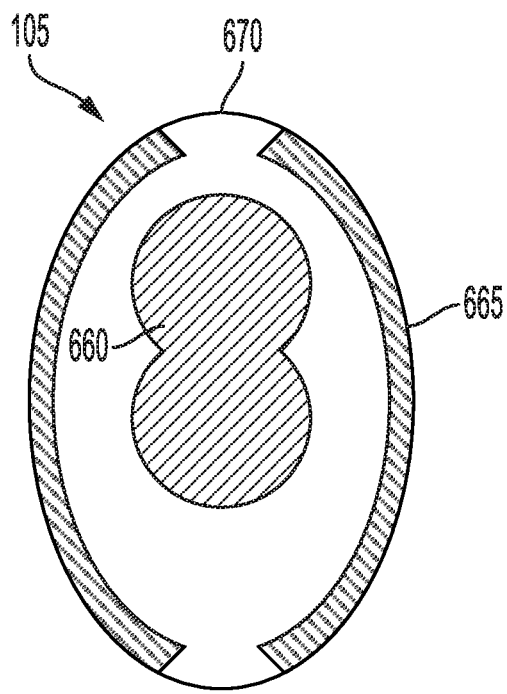
FIG. 10C depicts an example schematic of a skin-interface surface of an example wearable cardiac monitoring and treatment device including a broken adhesive ring and a conductive gel patch.
Figure 10D:
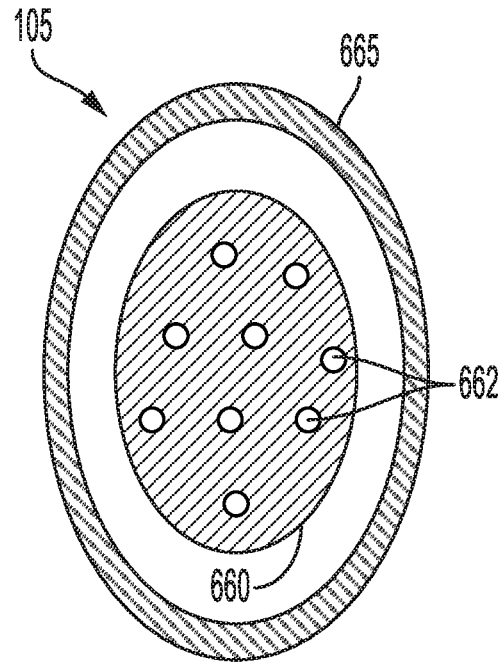
FIG. 10D depicts an example schematic of a skin-interface surface of an example wearable cardiac monitoring and treatment device including a continuous adhesive ring and a conductive gel patch including a plurality of perforations.

In implementations, such as that of FIG. 9B, a fan 944 may also draw air from an air inlet 945 of the housing 920 to create an airflow 950 within the housing. The air is then cooled down by the cooling device 943, such as a thermoelectric cooling device or cool pack, and blown across the breathable contoured pad 905 and the patient's skin 7 for added comfort via one or more air channels 946. (For simplicity, the skin 7 of the patient is shown only partially in FIG. 9B to represent the relative placement of the contoured pad 905 on the skin 7 as affixed by a breathable adhesive 938, such as a conductive breathable adhesive.) In implementations, the air inlet 945 is a channel or gap defined by the contoured pad 905 on one side and an inner housing wall 921 on the other. The inner housing wall 921 is shorter than the contoured pad 105 such that a gap 948 is defined between the end of the inner housing wall 921 and a connective portion 918 of the housing 120 anchored to the contoured pad 905. In implementations, the inner housing wall 921 includes one more supports 923 for anchoring the housing 920 to the contoured pad 905 at a distance defining the width of the channel Wc. In implementations, the one or more supports 923 can be conductive connectors configured to engage one or more therapy electrodes 110 or ECG electrodes 115.

In implementations, as shown in FIGS. 6, 8, and 9A-B, the first assembly 102, 802, 902 can include a passive heat management system disposed within the at least one housing. In implementations, the passive heat management system can include a cooling device 943 such as a removably inserted cool pack. In implementations, the passive heat management system can include a metallic heat sink layer 146 disposed within the housing, adjacent one or more of the plurality of ECG electrodes and/or the plurality of therapy electrodes. In some examples, the metallic heat sink layer 146 can be one or more pieces of light weight metal such as aluminum or stainless steel positioned within the housing and in contact with the contoured pad as depicted, for example in FIG. 9A. In implementations, the metallic heat layer can be formed as part of a printed circuit board, such as printed circuit board 145 of FIG. 6.

In implementations, the device can include a gel-based heat distribution system disposed within the at least one housing. Similar to a metallic heat sink layer 146 disposed within the housing, a gel-based heat distribution system is a layer of gel that conducts heat away from the one or more of the plurality of ECG electrodes and/or the plurality of therapy electrodes. As the layer of gel conducts heat from the skin 7 of the patient into the housing for active or passive expulsion by, for example, evaporation through one or more through holes and/or by fan-driven displacement through the housing 120.

As described previously, in implementations, the passive heat management system can include one or more through holes (e.g., through hole 148 of FIG. 6) extending between an interface between the contoured pad and the torso of the patient and an outer surface of the at least one housing 120. In implementations, one or more vapor release valves (e.g., vapor release valves 149*a-c* of the implementations of FIGS. 6 and 9A) can be formed into or disposed through the housing 120 for venting perspiration out of the housing 120, 820. As moisture vapor 903 from the skin 7 of the patient emanates through the breathable adhesive and vapor permeable contoured pad 105, vapor pressure inside the housing 120 can increase. In some implementations, the vapor release valves are pressure activated such that when moisture vapor increases within the housing 120, 820 and pressure within the housing increases to a threshold or trigger value, the one or more vapor release valves 149*a-c* open so that moisture evaporates. When moisture evaporates sufficiently to reduce the pressure within the housing below a threshold value, the vapor release valve closes. In implementations, the vapor release valve can be in communication with a processor of the device (e.g, processor 118 of FIG. 6) and electromechanically controlled.

In implementations, one or more vapor release valves 149 can be manually actuated by a patient or care giver providing an instruction to the device 100, 800 via a manual button press or finger tap on the device or on a remote device in communication with the processor 118. For example, a remote watch or smartphone running an application can provide a user with a user interface on which to tap to request valve actuation. In implementations, the device 100, 800 can include a moisture sensor within the housing 120, 820. The moisture sensor can be in communication with the processor 118 so that the processor automatically actuates the vapor release mechanism when a vapor level inside the housing reaches a threshold. In implementations, the threshold for automatically actuating the vapor release valve is pre-set on the device 100, 800. In implementations, the threshold for automatically actuating the vapor release valve can be configured by the patient, physician, or other care representative to customize the frequency of vapor release to a particular patient's perspiration rate and comfort level. For example, when a patient is exercising, he or she can set the frequency of opening the vapor release valve to once every 5 minutes, and when the patient is resting, he or she can set the frequency of opening the vapor release valve to once an hour.

As described above, the teachings of the present disclosure can be generally applied to external medical monitoring and/or treatment devices (e.g., devices that are not completely implanted within the patient's body). External medical devices can include, for example, ambulatory medical devices that are capable of and designed for moving with the patient as the patient goes about his or her daily routine. An example ambulatory medical device can be a wearable medical device such as a wearable cardioverter defibrillator (WCD), a wearable cardiac monitoring device, an in-hospital device such as an in-hospital wearable defibrillator, a short-term wearable cardiac monitoring and/or therapeutic device, and other similar wearable medical devices.

A wearable medical cardiac-monitoring device is capable of continuous use by the patient. Further, the wearable medical device can be configured as a long-term or extended use medical device. Such devices can be designed to be used by the patient for a long period of time, for example, a period of 24 hours or more, several days, weeks, months, or even years. Accordingly, the long period of use can be uninterrupted until a physician or other caregiver provides specific prescription to the patient to stop use of the wearable medical device. For example, the wearable medical device can be prescribed for use by a patient for a period of at least one week. In an example, the wearable medical device can be prescribed for use by a patient for a period of at least 30 days. In an example, the wearable medical device can be prescribed for use by a patient for a period of at least one month. In an example, the wearable medical device can be prescribed for use by a patient for a period of at least two months. In an example, the wearable medical device can be prescribed for use by a patient for a period of at least three months. In an example, the wearable medical device can be prescribed for use by a patient for a period of at least six months. In an example, the wearable medical device can be prescribed for use by a patient for a long period of at least one year. In some implementations, the extended use can be uninterrupted until a physician or other caregiver provides specific instruction to the patient to stop use of the wearable medical device.

Implementations of an adhesively coupled wearable device can include additional wearable supports and/or support garments for offsetting one or more forces such as peel forces, shear forces, cleavage forces, and tensile forces and retaining the wearable device in contact with the torso of the patient. In such implementations, the wearable supports and/or support garments assist with preventing the wearable device from pulling on the skin of the patient and therefore increase and/or ensure patient comfort throughout the duration of wear. Ensuring patient comfort removes an impediment to patient compliance with wearing the device throughout the prescribed durations. Such wearable supports and/or support garments can be especially beneficial during long-term durations of prescribed wear.

Regardless of the period of wear, the use of the wearable medical device can include continuous or nearly continuous wear by the patient as previously described. For example, the continuous use can include continuous wear or attachment of the wearable medical device to the patient. In implementations, the continuous attachment is through one or more of the electrodes as described herein during both periods of monitoring and periods when the device may not be monitoring the patient but is otherwise still worn by or otherwise attached to the patient. Continuous use can include continuously monitoring the patient while the patient is wearing the device for cardiac-related information (e.g., electrocardiogram (ECG) information, including arrhythmia information, cardiac vibrations, etc.) and/or non-cardiac information (e.g., blood oxygen, the patient's temperature, glucose levels, tissue fluid levels, and/or pulmonary vibrations). For example, the wearable medical device can carry out its continuous monitoring and/or recording in periodic or aperiodic time intervals or times (e.g., every few minutes, hours, once a day, once a week, or other interval set by a technician or prescribed by a caregiver). Alternatively or additionally, the monitoring and/or recording during intervals or times can be triggered by a user action or another event.

As noted above, the wearable medical device can be configured to monitor other physiologic parameters of the patient in addition to cardiac related parameters. For example, the wearable medical device can be configured to monitor, for example, pulmonary-vibrations (e.g., using microphones and/or accelerometers), breath vibrations, sleep related parameters (e.g., snoring, sleep apnea), tissue fluids (e.g., using radio-frequency transmitters and sensors), among others.

In implementations, the patient-worn arrhythmia monitoring and treatment device 100, 800 further includes a patient notification output. In response to detecting one or more treatable arrhythmia conditions, the processor 118 is configured to prompt the patient for a response by issuing the patient notification output, which may be an audible output, tactile output, visual output, or some combination of any and all of these types of notification outputs. In the absence of a response to the notification output from the patient, the processor is configured to cause the therapy delivery circuit 130 to deliver the one or more therapeutic pulses to the patient.

Figure 15:
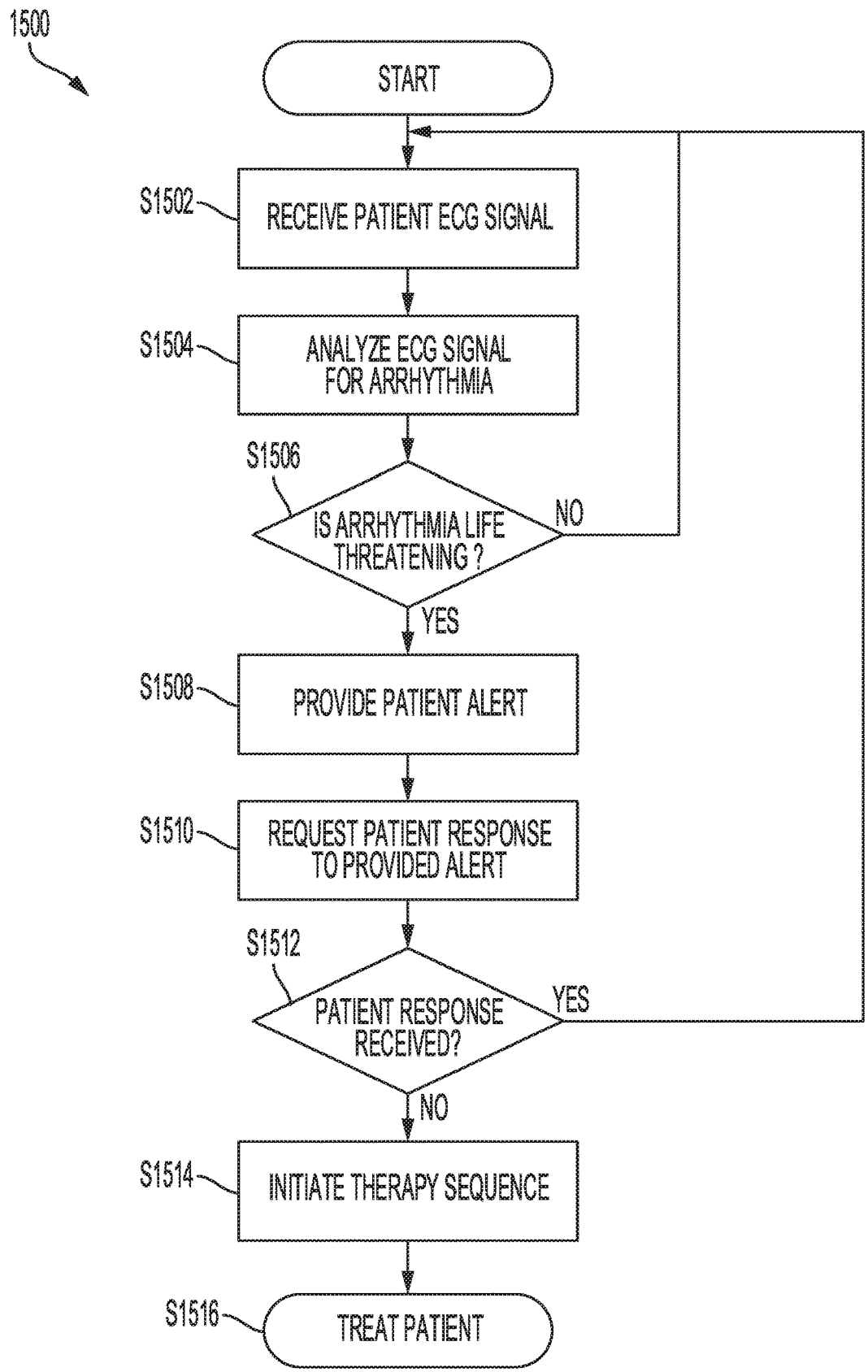
FIG. 15 is a schematic of an example method of using adhesively coupled wearable cardiac monitoring and treatment devices.

FIG. 15 depicts an example of a process 1500 for determining whether to initiate a therapy sequence and apply a therapeutic pulse to the body of a patient. In implementations, the processor 118, receives S1502 a patient ECG signal from the ECG electrodes 112 and analyzes S1504 the ECG signal for an arrhythmia condition. The processor 118 determines S1506 whether the arrhythmia is life threatening condition and requires treatment. If the arrhythmia is not life threatening, the processor 118 can cause a portion of the ECG signal to be stored in memory for later analysis and continue to monitor the patient ECG signal. If the arrhythmia is life threatening, the processor provides S1508 a patient notification output and requests S1510 a patient response to the provided notification output. In implementations, the patient responds to an alert by interacting with a user interface (e.g., the user interface 208 of FIG. 16), which includes, for example, one or more buttons (e.g. button 111 of FIG. 5C) or touch screen interface buttons with haptic feedback (e.g., touch screen buttons 811, 1011 of the user interface of the wrist and arm worn remote devices 810, 1010 of FIGS. 12A-B and 14 or like devices, such as smartphones running user-facing interactive applications). The response may be, for example, pressing one or more buttons in a particular sequence or for a particular duration. The processor 118 determines S1512 whether the patient response was received. If the patient responds to the notification output, the processor 118 is notified that the patient is conscious and returns to a monitoring mode. If the patient is unconscious and unable to respond to the provided alert, the processor 118 initiates S1514 the therapy sequence and treats S1516 the patient with the delivery of energy to the body of the patient.

In implementations, an example therapeutic medical device can include an in-hospital continuous monitoring defibrillator and/or pacing device, for example, an in-hospital wearable defibrillator. In such an example, the electrodes can be adhesively attached to the patient's skin. For example, the electrodes can include disposable adhesive electrodes. For example, the electrodes can include sensing and therapy components disposed on separate sensing and therapy electrode adhesive patches. In some implementations, both sensing and therapy components can be integrated and disposed on a same electrode adhesive patch that is then attached to the patient. In an example implementation, the electrodes can include a front adhesively attachable therapy electrode, a back adhesively attachable therapy electrode, and a plurality of adhesively attachable sensing electrodes. For example, the front adhesively attachable therapy electrode attaches to the front of the patient's torso to deliver pacing or defibrillating therapy. Similarly, the back adhesively attachable therapy electrode attaches to the back of the patient's torso. In an example scenario, at least three ECG adhesively attachable sensing electrodes can be attached to at least above the patient's chest near the right arm, above the patient's chest near the left arm, and towards the bottom of the patient's chest in a manner prescribed by a trained professional.

A patient being monitored by an in-hospital defibrillator and/or pacing device can be confined to a hospital bed or room for a significant amount of time (e.g., 90% or more of the patient's stay in the hospital). As a result, a user interface can be configured to interact with a user other than the patient, e.g., a nurse, for device-related functions such as initial device baselining, setting and adjusting patient parameters, and changing the device batteries.

In implementations, an example of a therapeutic medical device can include a short-term continuous monitoring defibrillator and/or pacing device, for example, a short-term outpatient wearable defibrillator. For example, such a short-term outpatient wearable defibrillator can be prescribed by a physician for patients presenting with syncope. A wearable defibrillator can be configured to monitor patients presenting with syncope by, e.g., analyzing the patient's cardiac activity for aberrant patterns that can indicate abnormal physiological function. For example, such aberrant patterns can occur prior to, during, or after the onset of symptoms. In such an example implementation of the short-term wearable defibrillator, the electrode assembly can be adhesively attached to the patient's skin and have a similar configuration as the in-hospital defibrillator described above.

FIGS. 1 through 5C, 9A-B, and 12A-13C illustrate example medical devices 10 (e.g. devices 10A-10G), 100, 800, 900 that are external, ambulatory, and wearable by a patient, and configured to implement one or more configurations described herein. For example, the medical device 10,100,800 can be a non-invasive medical device configured to be located substantially external to the patient. Such a medical device can be, for example, an ambulatory medical device that is capable of and designed for moving with the patient as the patient goes about his or her daily routine. The example medical devices as described herein can be bodily-attached to the patient via an adhesive pad and/or via a wearable support and/or support garment worn about the torso of the patient. For example, the medical device can be a wearable cardioverter defibrillator. Such wearable defibrillators typically are worn nearly continuously or substantially continuously for two to three months at a time. During the period of time in which they are worn by the patient, the wearable defibrillator can be configured to continuously or substantially continuously monitor the vital signs of the patient and, upon determination that treatment is required, can be configured to deliver one or more therapeutic electrical pulses to the patient. For example, such therapeutic shocks can be pacing, defibrillation, or transcutaneous electrical nerve stimulation (TENS) pulses. In some implementations, the medical devices 10, 100, 800, 900 may be prescribed for long-term duration of wear and include a wearable support and/or support garment. In some implementations of the medical devices 10, 100, 800, 900 may be prescribed for short-term durations of wear and rely only on adhesives without the need for one or more additional wearable supports and/or support garments to provide reliability and patient comfort throughout the duration of wear.

In examples, the medical device can include physiological sensors configured to detect one or more cardiac signals. Examples of such signals include ECG signals and/or other sensed cardiac physiological signals from the patient. In certain implementations, the physiological sensors can include additional components such as accelerometers, vibrational sensors, and other measuring devices for recording additional parameters. For example, the physiological sensors can also be configured to detect other types of patient physiological parameters and vibrational signals, such as tissue fluid levels, cardio-vibrations, pulmonary-vibrations, respiration-related vibrations of anatomical features in the airway path, patient movement, etc. Example physiological sensors can include ECG sensors including a metal electrode with an oxide coating such as tantalum pentoxide electrodes, as described in, for example, U.S. Pat. No. 6,253,099 entitled "Cardiac Monitoring Electrode Apparatus and Method," the content of which is incorporate herein by reference.

In examples, the physiological sensors can include a heart rate sensor for detecting heart beats and monitoring the heart rate of the patient. For instance, such heart rate sensors can include the ECG sensors and associated circuitry described above. In some examples, the heart rate sensors can include a radio frequency based pulse detection sensor or a pulse oximetry sensor worn adjacent an artery of the patient. In implementations, the heart rate sensor can be worn about the wrist of a patient, for example, incorporated on and/or within a watch or a bracelet. In some examples, the heart rate sensor can be integrated within a patch adhesively coupled to the skin of the patient over an artery.

In some examples, the therapy electrodes 110 can also be configured to include sensors configured to detect ECG signals as well as other physiological signals of the patient. The ECG data acquisition and conditioning circuitry 125 is configured to amplify, filter, and digitize these cardiac signals. One or more of the therapy electrodes 110 can be configured to deliver one or more therapeutic defibrillating shocks to the body of the patient when the medical device 100, 800 determines that such treatment is warranted based on the signals detected by the ECG sensors 115 and processed by the processor 118. Example therapy electrodes 110 can include conductive metal electrodes such as stainless steel electrodes that include, in certain implementations, one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a patient (e.g., not provide or perform any therapeutic functions). The therapeutic elements can be deactivated (e.g., by means or a physical or a software switch), essentially rendering the therapeutic medical device as a monitoring medical device for a specific physiologic purpose or a particular patient. As an example of a software switch, an authorized person can access a protected user interface of the medical device and select a preconfigured option or perform some other user action via the user interface to deactivate the therapeutic elements of the medical device.

Figure 16:
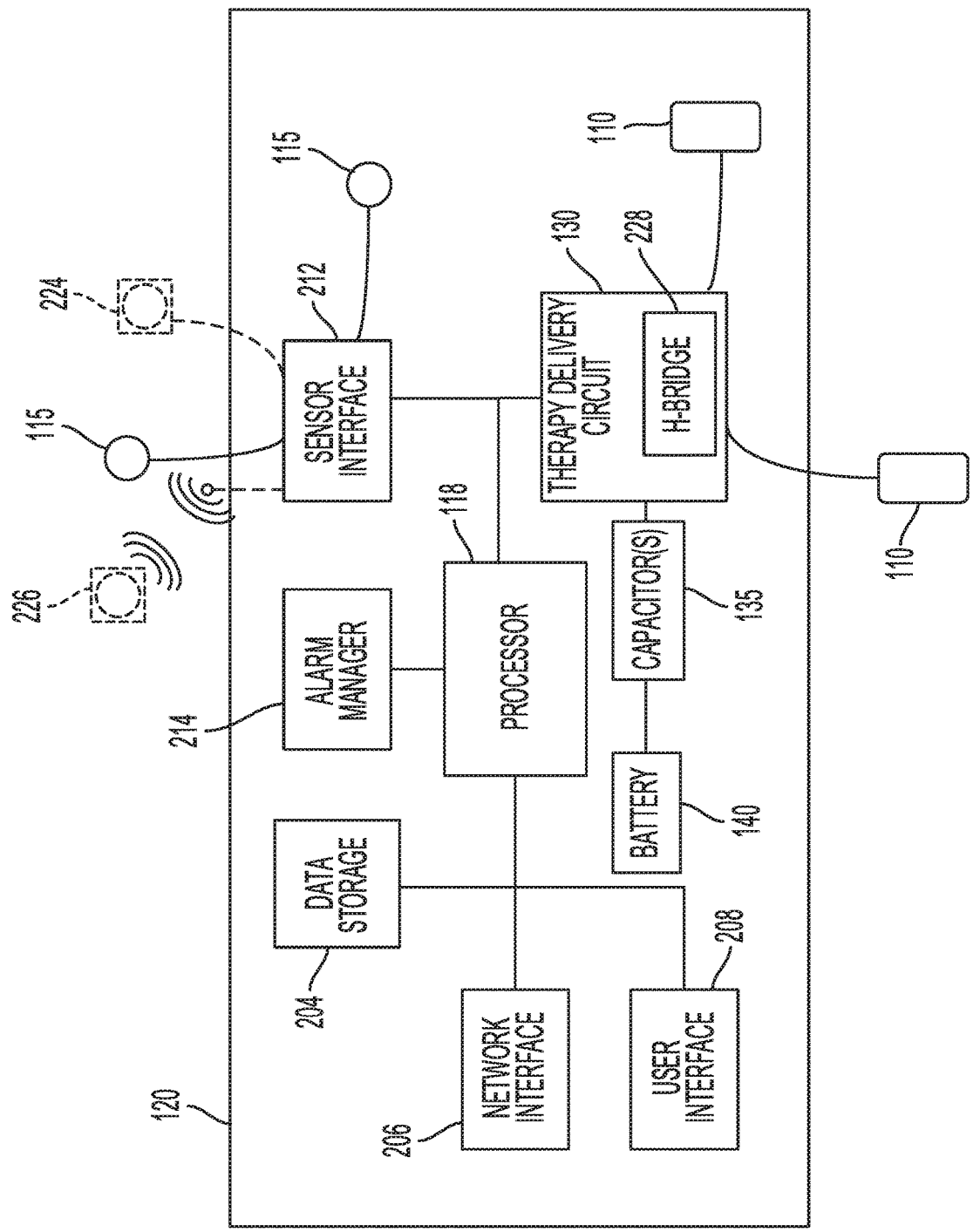
FIG. 16 depicts a schematic diagram of an embodiment of an adhesively coupled wearable cardiac monitoring and treatment device.

FIG. 16 illustrates an example component-level view of the medical device. As shown in FIG. 16, the medical device housing 120 can include a therapy delivery circuit 130 including a polarity switching component such as an H-bridge 228, a data storage 204, a network interface 206, a user interface 208 at least one battery 140, a sensor interface 212 that includes, for example, an ECG data acquisition and conditioning circuit 125, an alarm manager 214, least one processor 118, and one or more capacitors 135. A patient monitoring medical device can include components like those described with regard to FIG. 16, but does not include the therapy delivery circuit 130. Alternatively, a patient monitoring medical device can include components like those described with regard to FIG. 16, but includes a switching mechanism for rendering the therapy delivery circuit 130 inoperative.

The therapy delivery circuit 130 is coupled to two or more therapy electrodes 110 configured to provide therapy to the patient. As indicated in FIG. 16, in examples, at least one of the two or more therapy electrodes 110 is within the housing 120 and another of the two or more therapy electrodes 110 is remote from the housing 120. For example, the therapy delivery circuit 130 includes, or is operably connected to, circuitry components that are configured to generate and provide the therapeutic shock. The circuitry components include, for example, resistors, one or more capacitors, relays and/or switches, an electrical bridge such as an H-bridge 228 (e.g., an H-bridge including a plurality of insulated gate bipolar transistors or IGBTs that deliver and truncate a therapy pulse), voltage and/or current measuring components, and other similar circuitry arranged and connected such that the circuitry work in concert with the therapy delivery circuit and under control of one or more processors (e.g., processor 118) to provide, for example, one or more pacing or defibrillation therapeutic pulses.

Pacing pulses can be used to treat cardiac arrhythmias such as bradycardia (e.g., in some implementations, less than 30 beats per minute) and tachycardia (e.g., in some implementations, more than 150 beats per minute) using, for example, fixed rate pacing, demand pacing, anti-tachycardia pacing, and the like. Defibrillation pulses can be used to treat ventricular tachycardia and/or ventricular fibrillation.

In implementations, each of the therapy electrodes 110 has a conductive surface adapted for placement adjacent the patient's skin and has an impedance reducing means contained therein or thereon for reducing the impedance between a therapy electrode and the patient's skin. As previously described with regard to implementations, each of the therapy electrodes can include a conductive impedance reducing adhesive layer, such as a breathable anisotropic conductive hydrogel disposed between the therapy electrodes and the torso of the patient. In implementations, the adhesively coupled patient-worn arrhythmia monitoring and treatment device 100, 800 may include gel deployment circuitry configured to cause the delivery of conductive gel substantially proximate to a treatment site (e.g., a surface of the patient's skin in contact with the therapy electrode 110) prior to delivering therapeutic shocks to the treatment site. As described in U.S. Pat. No. 9,008,801, titled "WEAR- ABLE THERAPEUTIC DEVICE," issued on Apr. 14, 2015 (hereinafter the "'801 Patent"), which is incorporated herein by reference in its entirety, the gel deployment circuitry can be configured to cause the delivery of conductive gel immediately before delivery of the therapeutic shocks to the treatment site, or within a short time interval, for example, within about 1 second, 5 seconds, 10 seconds, 30 seconds, or one minute before delivery of the therapeutic shocks to the treatment site. Such gel deployment circuitry can be coupled to or integrated within a first assembly 102, 802, a second assembly 107, 807 and/or a third assembly of the device.

When a treatable cardiac condition is detected and no patient response is received after device prompting, the gel deployment circuitry can be signaled to deploy the conductive gel. In some examples, the gel deployment circuitry can be constructed as one or more separate and independent gel deployment modules. Such modules can be configured to receive removable and/or replaceable gel cartridges (e.g., cartridges that contain one or more conductive gel reservoirs). As such, the gel deployment circuitry can be permanently disposed in the device as part of the therapy delivery systems, while the cartridges can be removable and/or replaceable.

In some implementations, the gel deployment modules can be implemented as gel deployment packs and include at least a portion of the gel deployment circuitry along with one or more gel reservoirs within the gel deployment pack. In such implementations, the gel deployment pack, including the one or more gel reservoirs and associated gel deployment circuitry can be removable and/or replaceable. In some examples, the gel deployment pack, including the one or more gel reservoirs and associated gel deployment circuitry, and the therapy electrode can be integrated into a therapy electrode assembly that can be removed and replaced as a single unit either after use, or if damaged or broken.

Figure 17:
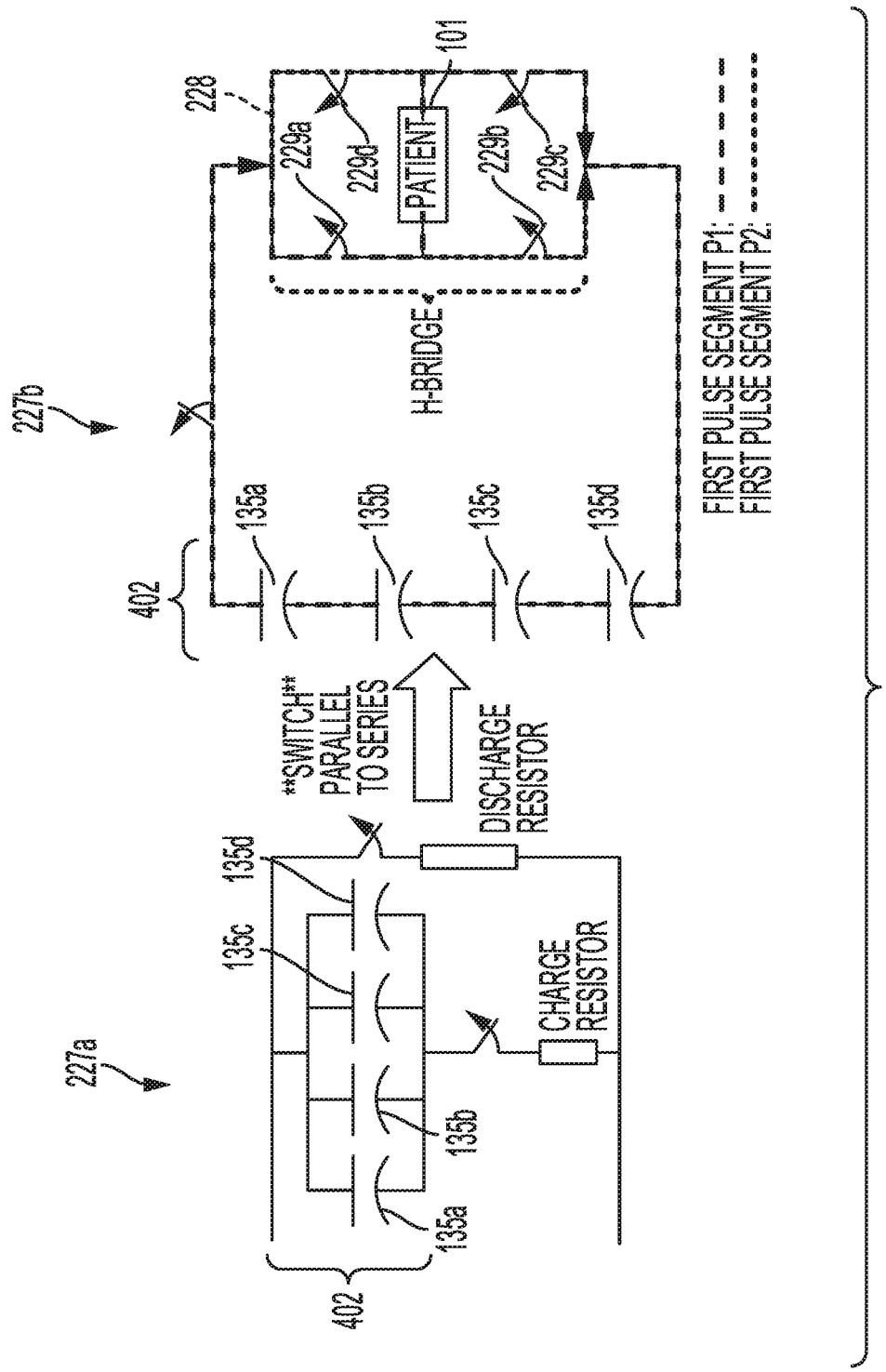
FIG. 17 depicts a schematic diagram of an embodiment of electrical components of an adhesively coupled wearable cardiac monitoring and treatment device.

Continuing with the description of the example medical device of FIG. 16, in implementations, the one or more capacitors 135 is a plurality of capacitors (e.g., two, three, four or more capacitors) comprising a capacitor bank 402, as shown in FIG. 17. These capacitors 135 can be switched into a series connection during discharge for a defibrillation pulse. For example, four capacitors of approximately 650 g can be used. In one implementation, the capacitors can have between 200 to 2500 volt surge rating and can be charged in approximately 5 to 30 seconds from a battery 140 depending on the amount of energy to be delivered to the patient. Additional implementations of capacitor properties and arrangements on a patient-worn medical device are provided herein in subsequent sections.

For example, each defibrillation pulse can deliver between 60 to 400 joules (J) of energy. In some implementations, the defibrillating pulse can be a biphasic truncated exponential waveform, whereby the signal can switch between a positive and a negative portion (e.g., charge directions). An amplitude and a width of the two phases of the energy waveform can be automatically adjusted to deliver a predetermined energy amount.

The data storage 204 can include one or more of non-transitory computer readable media, such as flash memory, solid state memory, magnetic memory, optical memory, cache memory, combinations thereof, and others. The data storage 204 can be configured to store executable instructions and data used for operation of the medical device. In certain implementations, the data storage 204 can include executable instructions that, when executed, are configured to cause the processor 118 to perform one or more functions.

In some examples, the network interface 206 can facilitate the communication of information between the medical device and one or more other devices or entities over a communications network. For example, the network interface 206 can be configured to communicate with a remote computing device such as a remote server or other similar computing device. The network interface 206 can include communications circuitry for transmitting data in accordance with a BLUETOOTH wireless standard for exchanging such data over short distances to an intermediary device(s) (e.g., a base station, a "hotspot" device, a smartphone, a tablet, a portable computing device, and/or other devices in proximity of the wearable medical device 100). The intermediary device(s) may in turn communicate the data to a remote server over a broadband cellular network communications link, The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a WI-FI communications link based on the IEEE 802.11 standard.

In certain implementations, the user interface 208 can include one or more physical interface devices such as input devices, output devices, and combination input/output devices and a software stack configured to drive operation of the devices. These user interface elements may render visual, audio, and/or tactile content. Thus, the user interface 208 may receive input or provide output, thereby enabling a user to interact with the medical device. In some implementations, the user interface 208 can be implanted as a handheld user interface device. (See, for example, the patient interface pod 40 of FIG. 1 and the wrist and arm worn remote devices 810, 1010 of FIGS. 12 and 14.) For instance, the hand-held user interface device can be a smartphone or other portable device configured to communicate with the processor 118 via the network interface 206. In an implementation, the hand-held user interface device may also be the intermediary device for facilitating the transfer of information from the device to a remote server.

As described, the medical device can also include at least one battery 140 configured to provide power to one or more components, such as the one or more capacitors 135. The battery 140 can include a rechargeable multi-cell battery pack. In one example implementation, the battery 140 can include three or more 2200 mAh lithium ion cells that provide electrical power to the other device components. For example, the battery 140 can provide its power output in a range of between 20 mA to 1000 mA (e.g., 40 mA) output and can support 24 hours, 48 hours, 72 hours, or more, of runtime between charges. As previously descried in detail, in certain implementations, the battery capacity, runtime, and type (e.g., lithium ion, nickel-cadmium, or nickel-metal hydride) can be changed to best fit the specific application of the medical device.

The sensor interface 212 can be coupled to one or more sensors configured to monitor one or more physiological parameters of the patient. As shown in FIG. 16, the sensors can be coupled to the medical device controller (e.g., processor 118) via a wired or wireless connection. The sensors can include one or more sensing electrodes (e.g., ECG sensors 115), vibrations sensors 224, and tissue fluid monitors 226 (e.g., based on ultra-wide band radiofrequency devices). For example, the sensor interface 212 can include ECG circuitry (such as ECG acquisition and conditioning circuitry 125 of FIGS. 6 and 8) and/or accelerometer circuitry, which are each configured to receive and condition the respective sensor signals.

The sensing electrodes can monitor, for example, a patient's ECG information. For example, the sensing electrodes of FIG. 16 can be ECG sensors 115 and can include conductive electrodes with stored gel deployment (e.g., metallic electrodes with stored conductive gel configured to be dispersed in the electrode-skin interface when needed), conductive electrodes with a conductive adhesive layer, or dry electrodes (e.g., a metallic substrate with an oxide layer in direct contact with the patient's skin). The sensing electrodes can be configured to measure the patient's ECG signals. The sensing electrodes can transmit information descriptive of the ECG signals to the sensor interface 212 for subsequent analysis.

The vibrational sensors 224 can detect a patient's cardiac or pulmonary (cardiopulmonary) vibration information. For example, the cardiopulmonary vibrations sensors 224 can be configured to detect cardio-vibrational biomarkers in a cardio-vibrational signal, including any one or all of S1, S2, S3, and S4 cardio-vibrational biomarkers. From these cardio-vibrational biomarkers, certain electromechanical metrics can be calculated, including any one or more of electromechanical activation time (EMAT), percentage of EMAT (% EMAT), systolic dysfunction index (SDI), left ventricular diastolic perfusion time (LDPT), and left ventricular systolic time (LVST). The cardiopulmonary vibrations sensors 224 may also be configured to detect hear wall motion, for example, by placement of the sensor 224 in the region of the apical beat.

The vibrations sensors 224 can include an acoustic sensor configured to detect vibrations from a subject's cardiac or pulmonary (cardiopulmonary) system and provide an output signal responsive to the detected vibrations of the targeted organ. For instance, in some implementations, the vibrations sensors 224 are able to detect vibrations generated in the trachea or lungs due to the flow of air during breathing. The vibrations sensors 224 can also include a multi-channel accelerometer, for example, a three channel accelerometer configured to sense movement in each of three orthogonal axes such that patient movement/body position can be detected. The vibrations sensors 224 can transmit information descriptive of the cardiopulmonary vibrations information or patient position/movement to the sensor interface 212 for subsequent analysis.

The tissue fluid monitors 226 can use radio frequency (RF) based techniques to assess changes of accumulated fluid levels over time. For example, the tissue fluid monitors 226 can be configured to measure fluid content in the lungs (e.g., time-varying changes and absolute levels), for diagnosis and follow-up of pulmonary edema or lung congestion in heart failure patients. The tissue fluid monitors 226 can include one or more antennas configured to direct RF waves through a patient's tissue and measure output RF signals in response to the waves that have passed through the tissue. In certain implementations, the output RF signals include parameters indicative of a fluid level in the patient's tissue. The tissue fluid monitors 226 can transmit information descriptive of the tissue fluid levels to the sensor interface 212 for subsequent analysis.

The sensor interface 212 can be coupled to any one or combination of sensing electrodes/other sensors to receive other patient data indicative of patient parameters. Once data from the sensors has been received by the sensor interface 212, the data can be directed by the processor 118 to an appropriate component within the medical device. For example, if cardiac data is collected by the cardiopulmonary vibrations sensor 224 and transmitted to the sensor interface 212, the sensor interface 212 can transmit the data to the processor 118 which, in turn, relays the data to a cardiac event detector. The cardiac event data can also be stored on the data storage 204.

An alarm manager 214 can be configured to manage alarm profiles and notify one or more intended recipients of events specified within the alarm profiles as being of interest to the intended recipients. These intended recipients can include external entities such as users (e.g., patients, physicians, other caregivers, patient care representatives, and other authorized monitoring personnel) as well as computer systems (e.g., monitoring systems or emergency response systems). The alarm manager 214 can be implemented using hardware or a combination of hardware and software. For instance, in some examples, the alarm manager 214 can be implemented as a software component that is stored within the data storage 204 and executed by the processor 118. In this example, the instructions included in the alarm manager 214 can cause the processor 118 to configure alarm profiles and notify intended recipients according to the configured alarm profiles. In some examples, alarm manager 214 can be an application-specific integrated circuit (ASIC) that is coupled to the processor 118 and configured to manage alarm profiles and notify intended recipients using alarms specified within the alarm profiles. Thus, examples of alarm manager 214 are not limited to a particular hardware or software implementation.

In some implementations, the processor 118 includes one or more processors (or one or more processor cores) that each are configured to perform a series of instructions that result in manipulated data and/or control the operation of the other components of the medical device. In some implementations, when executing a specific process (e.g., cardiac monitoring), the processor 118 can be configured to make specific logic-based determinations based on input data received, and be further configured to provide one or more outputs that can be used to control or otherwise inform subsequent processing to be carried out by the processor 118 and/or other processors or circuitry with which processor 118 is communicatively coupled. Thus, the processor 118 reacts to a specific input stimulus in a specific way and generates a corresponding output based on that input stimulus. In some example cases, the processor 118 can proceed through a sequence of logical transitions in which various internal register states and/or other bit cell states internal or external to the processor 118 can be set to logic high or logic low. The processor 118 can be configured to execute a function stored in software. For example, such software can be stored in a data store coupled to the processor 118 and configured to cause the processor 118 to proceed through a sequence of various logic decisions that result in the function being executed. The various components that are described herein as being executable by the processor 118 can be implemented in various forms of specialized hardware, software, or a combination thereof. For example, the processor can be a digital signal processor (DSP) such as a 24-bit DSP processor. The processor 118 can be a multi-core processor, e.g., a processor having two or more processing cores. The processor can be an Advanced RISC Machine (ARM) processor such as a 32-bit ARM processor or a 64-bit ARM processor. The processor can execute an embedded operating system and include services provided by the operating system that can be used for file system manipulation, display & audio generation, basic networking, firewalling, data encryption and communications.

In implementations, the therapy delivery circuit 130 includes, or is operably connected to, circuitry components that are configured to generate and provide the therapeutic shock. As described previously, the circuitry components include, for example, resistors, one or more capacitors 135, relays and/or switches, an electrical bridge such as an H-bridge 228 (e.g., an H-bridge circuit including a plurality of switches, (e.g. insulated gate bipolar transistors or IGBTs, silicon carbide field effect transistors (SiC FETs), metal-oxide semiconductor field effect transistors (MOSFETS), silicon-controlled rectifiers (SCRs), or other high current switching devices)), voltage and/or current measuring components, and other similar circuitry components arranged and connected such that the circuitry components work in concert with the therapy delivery circuit 130 and under control of one or more processors (e.g., processor 118) to provide, for example, one or more pacing or defibrillation therapeutic pulses.

In implementations, the device 100, 800 further includes a source of electrical energy, for example, the one or more capacitors 135, that stores and provides energy to the therapy delivery circuit 130. The one or more therapeutic pulses are defibrillation pulses of electrical energy, and the one or more treatable arrhythmias include ventricular fibrillation and ventricular tachycardia. In implementations, the one or more therapeutic pulses are biphasic exponential pulses. Such therapeutic pulses can be generated by charging the one or more capacitors 135 and discharging the energy stored in the one or more capacitors 135 into the patient. For example, the therapy delivery circuit 130 can include one or more power converters for controlling the charging and discharging of the one or more capacitors 135. In some implementations, the discharge of energy from the one or more capacitors 135 can be controlled by, for example, an H-bridge that controls the discharge of energy into the body of the patient, like the H-bridge circuit described in U.S. Pat. No. 6,280,461, titled "PATIENT-WORN ENERGY DELIVERY APPARATUS," issued on Aug. 28, 2001, and U.S. Pat. No. 8,909,335, titled "METHOD AND APPARATUS FOR APPLYING A RECTILINEAR BIPHASIC POWER WAVEFORM TO A LOAD," issued on Dec. 9, 2014, each of which is hereby incorporated herein by reference in its entirety.

As shown in the embodiment to FIG. 17, the H-bridge 228 is electrically coupled to a capacitor bank 402 including four capacitors 135*a-d* that are charged in parallel at a preparation phase 227*a* and discharged in series at a treatment phase 227*b*. In some implementations, the capacitor bank 402 can include more or fewer than four capacitors 135. During the treatment phase 227*b*, the H-bridge 228 applies a therapeutic pulse that causes current to flow through the torso 5 of the patient in desired directions for desired durations. The H-bridge 228 includes H-bridge switches 229*a-d* that are opened and closed selectively by a switching transistor such as insulated gate bipolar transistors (IGBTs), silicon carbide field effect transistors (SiC FETs), metal-oxide semiconductor field effect transistors (MOSFETS), silicon-controlled rectifiers (SCRs), or other high current switching devices. Switching a pair of transistors to a closed position, for example switches 229*a* and 229*c*, enables current to flow in a first direction for first pulse segment P1. Opening switches 229*a* and 229*c* and closing switches 229*b* and 229*d* enables current to flow through the torso 5 of the patient in a second pulse segment P2 directionally opposite the flow of the first pulse segment P1.

Although the subject matter contained herein has been described in detail for the purpose of illustration, it is to be understood that such detail is solely for that purpose and that the present disclosure is not limited to the disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:

1. A patient-worn arrhythmia monitoring and treatment device, comprising:
   at least one contoured pad configured to be adhesively coupled to a torso of a patient;
   a plurality of therapy electrodes, at least one of which is integrated with the at least one contoured pad;
   a plurality of ECG sensing electrodes, at least one of which is integrated with the at least one contoured pad;
   at least one housing configured to form a watertight seal with the at least one contoured pad, the at least one housing extending no more than 5 cm from a surface of the at least one contoured pad;
   an ECG acquisition and conditioning circuit disposed within the at least one housing and electrically coupled to the plurality of ECG sensing electrodes to provide at least one ECG signal of the patient;
   a therapy delivery circuit disposed within the at least one housing and configured to deliver one or more therapeutic pulses to the patient through the plurality of therapy electrodes; and
   a processor disposed within the at least one housing and coupled to the therapy delivery circuit and configured to
      analyze the at least one ECG signal of the patient and detect one or more treatable arrhythmias based on the at least one ECG signal; and
      cause the therapy delivery circuit to deliver at least one defibrillation pulse to the patient on detecting the one or more treatable arrhythmias,
   wherein the patient-worn arrhythmia monitoring and treatment device has a weight between 250 grams and 2,500 grams,
   wherein an assembly comprises the at least one housing, the ECG acquisition and conditioning circuit disposed within the at least one housing, the therapy delivery circuit disposed within the at least one housing, and the processor disposed within the at least one housing, and
   wherein the assembly is configured such that a center of mass of the assembly is below a volumetric center of the assembly with respect to a vertical axis of the assembly when the device is mounted on the patient as the patient is standing or sitting.

2. The device of claim 1, wherein the delivery of the at least one defibrillation pulse comprises a delivery of no more than one defibrillation pulse.

3. The device of claim 1, wherein the weight of the patient-worn arrhythmia monitoring and treatment device is between at least one of 250 grams and 1,250 grams, 500 grams and 1,000 grams, or 750 grams and 900 grams.

4. The device of claim 1, further comprising electronics disposed within the at least one housing comprising one or more of the therapy delivery circuit, the ECG acquisition and conditioning circuit, the processor, at least one capacitor, or at least one power source.

5. The device of claim 4, wherein the one or more of the therapy delivery circuit, the ECG acquisition and conditioning circuit, the processor, the at least one capacitor, or the at least one power source are each within a separate enclosure.

6. The device of claim 1, wherein a ratio of a distance between the center of mass and an inferior margin line of the at least one housing divided by a distance between the volumetric center and the inferior margin line is in a range of between at least one of 1% to 90%, 5% to 80%, or 10% to 70%.

7. The device of claim 1, wherein a ratio of a lateral distance between the center of mass and a patient-facing surface of the at least one contoured pad divided by a lateral distance between the volumetric center and the patient-facing surface of the at least one contoured pad is in a range of between at least one of 1% to 90%, 5% to 80%, or 10% to 70%.

8. The device of claim 4, wherein the at least one power source comprises one or more batteries having a combined envelope volume not to exceed one quarter of a volume of the at least one housing and having a capacity of 1200 mAh to 8000 mAh.

9. The device of claim 1, further comprising a breathable anisotropic conductive gel disposed between the at least one contoured pad and the torso and configured for placement along at least one of the plurality of therapy electrodes.

10. The device of claim 9, wherein a first ratio of an area footprint of the breathable anisotropic conductive gel to an area footprint of the at least one contoured pad ranges from about 0.30-0.75.

11. The device of claim 10, further comprising a breathable adhesive disposed between the at least one contoured pad and the torso, wherein a second ratio of the area footprint of the breathable adhesive to the area footprint of the at least one contoured pad ranges from about 0.05-0.25.

12. The device of claim 1, wherein the at least one contoured pad comprises one or more receptacles for receiving the at least one housing in a watertight mating.

13. The device of claim 12, wherein the one or more receptacles comprise a sealing lip.

14. The device of claim 13, wherein the sealing lip comprises an elastomeric waterproof material.

15. The device of claim 13, wherein the sealing lip engages a top surface of the at least one housing.

16. The device of claim 1, wherein the at least one housing is configured to extend between 1 cm and 5 cm from the surface of the at least one contoured pad.

17. The device of claim 1, wherein the at least one housing is configured to extend between 1 cm and 4 cm from the surface of the at least one contoured pad.

18. The device of claim 1, wherein the at least one housing is configured to extend between 1 cm and 3 cm from the surface of the at least one contoured pad.

19. The device of claim 13, wherein the at least one housing further comprises a peripheral flange and the sealing lip receives the peripheral flange.

* * * * *

UNITED STATES PATENT AND TRADEMARK OFFICE
CERTIFICATE OF CORRECTION

| | | |
|---|---|---|
| PATENT NO. | : 11,890,461 B2 | Page 1 of 1 |
| APPLICATION NO. | : 16/585344 | |
| DATED | : February 6, 2024 | |
| INVENTOR(S) | : Gary A. Freeman and James A. Patterson, III | |

It is certified that error appears in the above-identified patent and that said Letters Patent is hereby corrected as shown below:

On the Title Page

In References Cited item (56):
Page 2, Column 1, Line 9 (U.S. Patent Documents) - delete "Born et al.", insert -- Bornn et al. --
Page 3, Column 1, Line 4 (U.S. Patent Documents) - delete "Ibbus et al.", insert -- Libbus et al. --
Page 3, Column 1, Line 11 (U.S. Patent Documents) - delete "Narren et al.", insert -- Warren et al. --

In the Specification

Column 6, Line 8 - delete "in", insert -- In --
Column 8, Line 19 - delete "configure", insert -- configured --
Column 8, Line 63 - delete "the an", insert -- the --
Column 8, Line 64 - deleted "couple", insert -- coupled --
Column 23, Line 9 - delete "be be", insert -- be --
Column 23, Line 19 - delete "650 g", insert -- 650 µF --
Column 27, Line 51 - delete "the a", insert -- a --
Column 29, Line 43 - delete "EGC", insert -- ECG --
Column 30, Line 51 - delete "70%", insert -- 70%. --
Column 35, Line 51 - delete "can be in the of a", insert -- can be a --
Column 38, Line 37 - delete "dioxitiophene),", insert -- dioxythiophene), --
Column 38, Line 39 - delete "(PANT)", insert -- (PANI) --
Column 38, Line 39 - delete "poly(thiopene)s,", insert -- poly(thiophene)s, --
Column 38, Line 39-40 - delete "co-bithiophen)", insert -- co-bithiophene) --
Column 40, Line 52 - delete "806", insert -- 807 --
Column 42, Line 21 - delete "802", insert -- 806 --
Column 46, Line 64 - delete "e.g,", insert -- e.g., --
Column 48, Line 45 - delete "e.g.", insert -- e.g., --
Column 54, Line 43 - delete "650 g", insert -- 650 µF --

Signed and Sealed this
Twenty-first Day of May, 2024

Katherine Kelly Vidal
*Director of the United States Patent and Trademark Office*